US007794962B2

(12) United States Patent
Emalfarb et al.

(10) Patent No.: US 7,794,962 B2
(45) Date of Patent: *Sep. 14, 2010

(54) HIGH-THROUGHPUT SCREENING OF EXPRESSED DNA LIBRARIES IN FILAMENTOUS FUNGI

(75) Inventors: Mark A. Emalfarb, Jupiter, FL (US); Peter J. Punt, Houten (NL); Cornelia van Zeijl, Vleuten-de-Meern (NL); Cornelius van den Hondel, Gouda (NL)

(73) Assignee: Dyadic International (USA), Inc., Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/490,761

(22) Filed: Jul. 21, 2006

(65) Prior Publication Data

US 2006/0257923 A1 Nov. 16, 2006

Related U.S. Application Data

(63) Continuation of application No. 09/834,434, filed on Apr. 13, 2001, now Pat. No. 7,122,330.

(51) Int. Cl.
*G01N 33/569* (2006.01)
*G01N 33/53* (2006.01)
*C07K 4/00* (2006.01)

(52) U.S. Cl. .................. 435/7.31; 435/7.2; 435/7.1; 435/6; 435/69.1; 435/471; 435/254.11; 536/23.1; 530/350

(58) Field of Classification Search .................. 435/6, 435/7, 69.1, 471, 254.11, 7.31, 7.2, 7.1; 536/23.1; 530/350
See application file for complete search history.

(56) References Cited

U.S. PATENT DOCUMENTS

| | | | |
|---|---|---|---|
| 4,816,405 A | 3/1989 | Yelton et al. | |
| 5,536,661 A | 7/1996 | Boel et al. | |
| 5,578,463 A | 11/1996 | Berka et al. | |
| 5,695,985 A | 12/1997 | Jensen et al. | |
| 5,783,431 A | 7/1998 | Peterson et al. | |
| 5,811,381 A * | 9/1998 | Emalfarb et al. | ............ 510/320 |
| 5,824,485 A | 10/1998 | Thompson et al. | |
| 5,830,696 A | 11/1998 | Short | |
| 5,939,250 A | 8/1999 | Short | |
| 5,958,672 A | 9/1999 | Short | |
| 5,989,814 A | 11/1999 | Frankel et al. | |
| 6,030,779 A | 2/2000 | Short | |
| 6,054,267 A | 4/2000 | Short | |
| 6,057,103 A | 5/2000 | Short | |
| 6,060,305 A | 5/2000 | Royer et al. | |
| 6,066,493 A | 5/2000 | Shuster et al. | |
| 6,184,026 B1 | 2/2001 | Shuster et al. | |
| 6,518,042 B1 | 2/2003 | Borchert et al. | |
| 6,573,086 B1 | 6/2003 | Emalfrab et al. | |

FOREIGN PATENT DOCUMENTS

| | | |
|---|---|---|
| EP | 1 022 335 | 7/2000 |
| WO | WO 93/11249 | 6/1993 |
| WO | WO 97/26330 | 7/1997 |
| WO | WO 99/32617 | 7/1999 |
| WO | WO 00/20555 | 4/2000 |
| WO | WO 00/50567 | 8/2000 |
| WO | WO 00/56893 | 9/2000 |
| WO | WO 01/09352 | 2/2001 |

OTHER PUBLICATIONS

Bergès, T. et al., "Cloning of an *Aspergillus niger* invertase gene by expression in *Trichoderma reesei*", Springer-verlag, vol. 24., pp. 53-59, 1993.
Clark, D.S., "Submerged Citric Acid Fermentation of Ferrocyanide-Treated Beet Molasses: Morphology of Pellets of *Aspergillus niger*," *Canadian Journal of Microbiology*, vol. 8, 1962, pp. 133-136.
Dai, Ziyu et al., "Identification of Genes Associated with Morphology in *Aspergillus niger* by Using Suppression Subtractive Hybridization," *Applied and Environmental Microbiology*, Apr. 2004, pp. 2474-2485.
Gu, B.J. et al., "A Glue-496 to Ala Polymorphism Leads to Loss of Function of the Human P2X$_7$ Receptor*," *J. Bio Chem.*, vol. 276, No. 14, pp. 11135-11142, Apr. 6, 2001.
Konig et al., "Strategies for Penicillin Fermentation in Tower-Loop Reactors," *Biotechnology and Bioengineering*, 1982, vol. XXIV, pp. 259-280.
PCT International Search Report (Jul. 2, 2001) from corresponding International PCT application No. PCT/US01/12335.
Short, Jay M. "Recombinant Approaches For Accessing Biodiversity", *Nature Biotechnology*, 1997, vol. 15 pp. 1322-1323.
Unkles, Shiela E. et al., "The development of a homologous transformation system for *Aspergillus oryzae* based on the nitrate assimilation pathway: A convenient and general selection system for filamentous fungal transformation," *Mol. Gen. Genet.*, 1989, vol. 218, pp. 99-104.
Wiebe, Marilyn G., "Characterization of morphological mutants generated spontaneously in glucose-limited, continuous flow cultures of *Fusarium graminearum* A3/5," *Mycol. Res.* 1992, vol. 96, No. 7, pp. 555-562.
Xu, Jiangfeng, et al. "Increased Heterologous Protein Production in *Aspergillus niger* Fermentation through Extracellular Proteases Inhibition by Pelleted Growth," *Biotechnol. Prog.* 2000, vol. 16, pp. 222-227.
Agency Response Letter GRAS Notice No. GRN 000292 (Sep. 29, 2009) from Mitchell A. Cheeseman, Acting Director; hyper text transfer protocol://www.fda.gov.

* cited by examiner

*Primary Examiner*—T. D. Wessendorf
(74) *Attorney, Agent, or Firm*—McDermott, Will & Emery, LLP

(57) ABSTRACT

The invention provides a method for the expression of exogenous DNA libraries in filamentous fungi. The fungi are capable of processing intron-containing eukaryotic genes, and also can carry out post-translational processing steps such as glycosylation and protein folding. The invention provides for the use of fungi with altered morphology, which permits high-throughput screening and directed molecular evolution of expressed proteins. The same transformed fungi may be used to produce larger quantities of protein for isolation, characterization, and application testing, and may be suitable for commercial production of the protein as well.

7 Claims, 20 Drawing Sheets pyrE gene sequence

SEQ ID NO:1
Pyre/niger   Length: 1578   March 9, 2001 09:28   Type: N   Check: 2282

```
   1 GGGTTAATGT GAAGGCGTTA GTGGTAATGT ATATTAATGG TGAGATGGGC
  51 TTTGATTGGG TTTAATTGGA ATCTGTATAT TTTCAGATGG AGTCAACTTT
 101 TGAATGGCCA ATATATCCTC GGCGATACCG TCGGAGATAA GATAAGAATA
 151 ATCGCACACT ATTCCCAAAG CATACTGGTA CATACTGCAT TCGGCTAGTG
 201 CGGGGTGCTT ACCTCATCCA CCCGAATGAG CCCAACTTTT TTGTCTCAAT
 251 CAATAATTGC ATCCAAATTC CCCCGCAACT TCCCCCTCCA ACCCCGTGTC
 301 TATACCACTC CCTCCACACC CACACAATCA CAATGGCTCT CCCTGCCTAC
 351 AAGACCGCCT TCCTGGAGTC TCTCGTCGGC CAACGTGCTG ACTTTCGGCA
 401 CCTTCACCCT GAAGTCGGGT CGCCGTGCGT CACCCCTCCA ACACCGGCAT
 451 TATCGCAATC GGAAGACTTA CCACTGTATA CAGACTCCCC CTACTTCTTC
 501 AACGCCGGCA TCTTCAACAC CGCCTCTCTC CTCTCCGCCC TCTCCACCAT
 551 GGCCCACACC ATCATCACCT TCCTCGCTGA GAACCCTTCC ATCCCCAAGC
 601 CCGACGTCAT GCTTCGGGTA AAAAACCCCC TCTTTCCCCA ATACCCCACT
 651 TCCACTCAAC AACCCATAAA TAACTAACAA AAACCCCCTA AACAGCCCCG
 701 CATACAAAGG CATCCCCCTC GCGTGCGCCA CCCTCCTTGA ACTCAACCGC
 751 ATCGACCCCG CCACCTGGGG CAGCGTGTCC TACAGCTACA ACCGCAAAGA
 801 AGCCAAGGAT CACGGCGAAG GCGGCAACAT TGTCGGCGCC GCTCTGAAGG
 851 GCAAGACCGT GCTTGTGATC GACGATGTCA TCACGGCCGG TACCGCCATG
 901 CGTGAGACCC TCAACCTGGT CGCCAAGGAG GGCGGCAAGG TCGTCGGATT
 951 CACTGTTGCT CTGGACCGCT GGAGAAGAT GCCCGGACCC AAGGACGAGA
1001 ACGGTGTCGA GGACGATAAG CCCAGAATGA GTGCTATGGG TCAGATCCGT
1051 AAGGAGTATG GTGTGCCCAC GACGAGTATT GTTACTCTGG ATGATTTGAT
1101 CAAGTTGATG CAGGCGAAGG GCAATGAGGC CGATATGAAG CGGTTGGAGG
1151 AGTATAGGGC TAAGTATCAG GCTAGTGATT AGTCGGTTTC ATTGACCGAT
```

FIG. 15A

```
1201   TGTTTGGGTG  GGTGTGAGAG  GTTAGGTTAG  GTTGTGGGCG  TAGGAATGAA

1251   AAGCTGTATA  CATAGGGGCC  TGAAGAGGTG  CGTAGAGACG  GTCGTGAGAT

1301   GTTTTATGTC  AAAATCTTGA  ACAAATGACA  CCTTAAAAAA  GACCCCTTGG

1351   TTTCAGCTGA  ATTAGCCCGG  AAAGATGCTC  GGCACGCCAT  GAGTCTAGCC

1401   CACTCAGTGG  GCACCCGTTT  CCCACATTTG  AAGTGGCCGA  CGCTTATTTG

1451   GCTGAGGCTG  TGGCCTGGAA  AGGCACTATG  GCGTGCTGCG  GTACAAGGCC

1501   GGGGCTGGCG  TACGAACCAC  GACGCCCGAA  GGGAACTCTT  CGGTCTTACT

1551   ACTACTATGT  CCCCAGTTGA  CCCCCCGA

SEQ ID NO:2

Translation of pyrE(1-1578)
Universal code

1      GGGTTAATGTGAAGGCGTTAGTGGTAATGTATATTAATGGTGAGATGGGCTTTGATTGGG
       CCCAATTACACTTCCGCAATCACCATTACATATAATTACCACTCTACCCGAAACTAACCC

1        G  L  M  *  R  R  *  W  *  C  I  L  M  V  R  W  A  L  I  G
1         G  *  C  E  G  V  S  G  N  V  Y  *  W  *  D  G  L  *  L  G
1          V  N  V  K  A  L  V  V  M  Y  I  N  G  E  M  G  F  D  W  V

61     TTTAATTGGAATCTGTATATTTTCAGATGGAGTCAACTTTTGAATGGCCAATATATCCTC
       AAATTAACCTTAGACATATAAAAGTCTACCTCAGTTGAAAACTTACCGGTTATATAGGAG

21       F  N  W  N  L  Y  I  F  R  W  S  Q  L  L  N  G  Q  Y  I  L
21        L  I  G  I  C  I  F  S  D  G  V  N  F  *  M  A  N  I  S  S
21         *  L  E  S  V  Y  F  Q  M  E  S  T  F  E  W  P  I  Y  P  R

121    GGCGATACCGTCGGAGATAAGATAAGAATAATCGCACACTATTCCCAAAGCATACTGGTA
       CCGCTATGGCAGCCTCTATTCTATTCTTATTAGCGTGTGATAAGGGTTTCGTATGACCAT

41       G  D  T  V  G  D  K  I  R  I  I  A  H  Y  S  Q  S  I  L  V
41        A  I  P  S  E  I  R  *  E  *  S  H  T  I  P  K  A  Y  W  Y
41         R  Y  R  R  R  *  D  K  N  N  R  T  L  F  P  K  H  T  G  T

181    CATACTGCATTCGGCTAGTGCGGGGTGCTTACCTCATCCACCCGAATGAGCCCAACTTTT
       GTATGACGTAAGCCGATCACGCCCCACGAATGGAGTAGGTGGGCTTACTCGGGTTGAAAA

```
241   TTGTCTCAATCAATAATTGCATCCAAATTCCCCCGCAACTTCCCCCTCCAACCCCGTGTC
      AACAGAGTTAGTTATTAACGTAGGTTTAAGGGGGCGTTGAAGGGGGAGGTTGGGGCACAG

81    L  S  Q  S  I  I  A  S  K  F  P  R  N  F  P  L  Q  P  R  V
 81     C  L  N  Q  *  L  H  P  N  S  P  A  T  S  P  S  N  P  V  S
 81      V  S  I  N  N  C  I  Q  I  P  P  Q  L  P  P  P  T  P  C  L
                        ?????????

301   TATACCACTCCCTCCACACCCACACAATCACAATGGCTCTCCCTGCCTACAAGACCGCCT
      ATATGGTGAGGGAGGTGTGGGTGTGTTAGTGTTACCGAGAGGGACGGATGTTCTGGCGGA

101    Y  T  T  P  S  T  P  T  Q  S  Q  W  L  S  L  P  T  R  P  P
101     I  P  L  P  P  H  P  H  N  H  N  G  S  P  C  L  Q  D  R  L
101      Y  H  S  L  H  T  H  T  I  T  M  A  L  P  A  Y  K  T  A  F
                                    ─  ─  ─  ─  ─  ─

361   TCCTGGAGTCTCTCGTCGGCCAACGTGCTGACTTTCGGCACCTTCACCCTGAAGTCGGGT
      AGGACCTCAGAGAGCAGCCGGTTGCACGACTGAAAGCCGTGGAAGTGGGACTTCAGCCCA
      ??????????????????????????
121    S  W  S  L  S  S  A  N  V  L  T  F  G  T  F  T  L  K  S  G
121     P  G  V  S  R  R  P  T  C  *  L  S  A  P  S  P  *  S  R  V
121      L  E  S  L  V  G  Q  R  A  D  F  R  H  L  H  P  E  V  G  S
                                  INTRON I
421   CGCCGTGCGTCACCCCTCCAACACCGGCATTATCGCAATCGGAAGACTTACCACTGTATA
      GCGGCACGCAGTGGGGAGGTTGTGGCCGTAATAGCGTTAGCCTTCTGAATGGTGACATAT

141    R  R  A  S  P  L  Q  H  R  H  Y  R  N  R  K  T  Y  H  C  I
       ─
141     A  V  R  H  P  S  N  T  G  I  I  A  I  G  R  L  T  T  V  Y
141      P  C  V  T  P  P  T  P  A  L  S  Q  S  E  D  L  P  L  Y  T

481   CAGACTCCCCCTACTTCTTCAACGCCGGCATCTTCAACACCGCCTCTCTCCTCTCCGCCC
      GTCTGAGGGGATGAAGAAGTTGCGGCCGTAGAAGTTGTGGCGGAGAGAGGAGAGGCGGG

161    Q  T  P  P  T  S  S  T  P  A  S  S  T  P  P  L  S  S  P  P
161     R  L  P  L  L  Q  R  R  H  L  Q  H  R  L  S  P  L  R  P
161      D  S  P  Y  F  F  N  A  G  I  F  N  T  A  S  L  L  S  A  L
            ─  ─  ─  ─  ─  ─  ─  ─  ─  ─  ─  ─  ─  ─  ─  ─  ─  ─

*NcoI*
541   TCTCCA*CCATGG*CCCACACCATCATCACCTTCCTCGCTGAGAACCCTTCCATCCCCAAGC
      AGAGGT*GGTACC*GGGTGTGGTAGTAGTGGAAGGAGCGACTCTTGGGAAGGTAGGGGTTCG

181    S  P  P  W  P  T  P  S  S  P  S  S  L  R  T  L  P  S  P  S
181     L  H  H  G  P  H  H  H  H  L  P  R  *  E  P  F  H  P  Q  A
181      S  T  M  A  H  T  I  I  T  F  L  A  E  N  P  S  I  P  K  P
         ─  ─  ─  ─  ─
      ???????????            INTRON II

601   CCGACGTCATGCTTCGGTAAAAAACCCCCTCTTTCCCCAATACCCCACTTCCACTCAAC
      GGCTGCAGTACGAAGCCCATTTTTTGGGGGAGAAAGGGGTTATGGGGTGAAGGTGAGTTG

```
661   AACCCATAAATAACTAACAAAAACCCCCTAAACAGCCCCGCATACAAAGGCATCCCCCTC
      TTGGGTATTTATTGATTGTTTTTGGGGGATTTGTCGGGGCGTATGTTTCCGTAGGGGGAG

221     N  P  *  I  T  N  K  N  P  L  N  S  P  A  Y  K  G  I  P  L
221       T  H  K  *  L  T  K  T  P  *  T  A  P  H  T  K  A  S  P  S
221         P  I  N  N  *  Q  K  P  P  K  Q  P  R  I  Q  R  H  P  P  R

721   GCGTGCGCCACCCTCCTTGAACTCAACCGCATCGACCCCGCCACCTGGGGCAGCGTGTCC
      CGCACGCGGTGGGAGGAACTTGAGTTGGCGTAGCTGGGGCGGTGGACCCCGTCGCACAGG

241     A  C  A  T  L  L  E  L  N  R  I  D  P  A  T  W  G  S  V  S
241       R  A  P  P  S  L  N  S  T  A  S  T  P  P  P  G  A  A  C  P
241         V  R  H  P  P  *  T  Q  P  H  R  P  R  H  L  G  Q  R  V  L

781   TACAGCTACAACCGCAAAGAAGCCAAGGATCACGGCGAAGGCGGCAACATTGTCGGCGCC
      ATGTCGATGTTGGCGTTTCTTCGGTTCCTAGTGCCGCTTCCGCCGTTGTAACAGCCGCGG

261     Y  S  Y  N  R  K  E  A  K  D  H  G  E  G  G  N  I  V  G  A
261       T  A  T  T  A  K  K  P  R  I  T  A  K  A  A  T  L  S  A  P
261         Q  L  Q  P  Q  R  S  Q  G  S  R  R  R  R  Q  H  C  R  R  R

KpnI
841   GCTCTGAAGGGCAAGACCGTGCTTGTGATCGACGATGTCATCACGGCCGGTACCGCCATG
      CGAGACTTCCCGTTCTGGCACGAACACTAGCTGCTACAGTAGTGCCGGCCATGGCGGTAC

281     A  L  K  G  K  T  V  L  V  I  D  D  V  I  T  A  G  T  A  M
281       L  *  R  A  R  P  C  L  *  S  T  M  S  S  R  P  V  P  P  C
281         S  E  G  Q  D  R  A  C  D  R  R  C  H  H  G  R  Y  R  H  A

901   CGTGAGACCCTCAACCTGGTCGCCAAGGAGGGCGGCAAGGTCGTCGGATTCACTGTTGCT
      GCACTCTGGGAGTTGGACCAGCGGTTCCTCCCGCCGTTCCAGCAGCCTAAGTGACAACGA

301     R  E  T  L  N  L  V  A  K  E  G  G  K  V  V  G  F  T  V  A
301       V  R  P  S  T  W  S  P  R  R  A  A  R  S  S  D  S  L  L  L
301         *  D  P  Q  P  G  R  Q  G  G  R  Q  G  R  R  I  H  C  C  S

961   CTGGACCGCTTGGAGAAGATGCCCGGACCCAAGGACGAGAACGGTGTCGAGGACGATAAG
      GACCTGGCGAACCTCTTCTACGGGCCTGGGTTCCTGCTCTTGCCACAGCTCCTGCTATTC

321     L  D  R  L  E  K  M  P  G  P  K  D  E  N  G  V  E  D  D  K
321       W  T  A  W  R  R  C  P  D  P  R  T  R  T  V  S  R  T  I  S
321         G  P  L  G  E  D  A  R  T  Q  G  R  E  R  C  R  G  R  *  A

1021  CCCAGAATGAGTGCTATGGGTCAGATCCGTAAGGAGTATGGTGTGCCCACGACGAGTATT
      GGGTCTTACTCACGATACCCAGTCTAGGCATTCCTCATACCACACGGGTGCTGCTCATAA

```
1081   GTTACTCTGGATGATTTGATCAAGTTGATGCAGGCGAAGGGCAATGAGGCCGATATGAAG
       CAATGAGACCTACTAAACTAGTTCAACTACGTCCGCTTCCCGTTACTCCGGCTATACTTC

361      V  T  L  D  D  L  I  K  L  M  Q  A  K  G  N  E  A  D  M  K
361       L  L  W  M  I  *  S  S  *  C  R  R  R  A  M  R  P  I  *  S
361         Y  S  G  *  F  D  Q  V  D  A  G  E  G  Q  *  G  R  Y  E  A

1141   CGGTTGGAGGAGTATAGGGCTAAGTATCAGGCTAGTGATTAGTCGGTTTCATTGACCGAT
       GCCAACCTCCTCATATCCCGATTCATAGTCCGATCACTAATCAGCCAAAGTAACTGGCTA

381      R  L  E  E  Y  R  A  K  Y  Q  A  S  D  *  S  V  S  L  T  D
381       G  W  R  S  I  G  L  S  I  R  L  V  I  S  R  F  H  *  P  I
381         V  G  G  V  *  G  *  V  S  G  *  *  L  V  G  F  I  D  R  L

1201   TGTTTGGGTGGGTGTGAGAGGTTAGGTTAGGTTGTGGGCGTAGGAATGAAAAGCTGTATA
       ACAAACCCACCCACACTCTCCAATCCAATCCAACACCCGCATCCTTACTTTTCGACATAT

401      C  L  G  G  C  E  R  L  G  *  V  V  G  V  G  M  K  S  C  I
401       V  W  V  G  V  R  G  *  V  R  L  W  A  *  E  *  K  A  V  Y
401         F  G  W  V  *  E  V  R  L  G  C  G  R  R  N  E  K  L  Y  T

1261   CATAGGGGCCTGAAGAGGTGCGTAGAGACGGTCGTGAGATGTTTTATGTCAAAATCTTGA
       GTATCCCCGGACTTCTCCACGCATCTCTGCCAGCACTCTACAAAATACAGTTTTAGAACT

421      H  R  G  L  K  R  C  V  E  T  V  V  R  C  F  M  S  K  S  *
421       I  G  A  *  R  G  A  *  R  R  S  *  D  V  L  C  Q  N  L  E
421         *  G  P  E  E  V  R  R  D  G  R  E  M  F  Y  V  K  I  L  N

1321   ACAAATGACACCTTAAAAAAGACCCCTTGGTTTCAGCTGAATTAGCCCGGAAAGATGCTC
       TGTTTACTGTGGAATTTTTTCTGGGGAACCAAAGTCGACTTAATCGGGCCTTTCTACGAG

441      T  N  D  T  L  K  K  T  P  W  F  Q  L  N  *  P  G  K  M  L
441       Q  M  T  P  *  K  R  P  L  G  F  S  *  I  S  P  E  R  C  S
441         K  *  H  L  K  K  D  P  L  V  S  A  E  L  A  R  K  D  A  R

1381   GGCACGCCATGAGTCTAGCCCACTCAGTGGGCACCCGTTTCCCACATTTGAAGTGGCCGA
       CCGTGCGGTACTCAGATCGGGTGAGTCACCCGTGGGCAAAGGGTGTAAACTTCACCGGCT

461      G  T  P  *  V  *  P  T  Q  W  A  P  V  S  H  I  *  S  G  R
461       A  R  H  E  S  S  P  L  S  G  H  P  F  P  T  F  E  V  A  D
461         H  A  M  S  L  A  H  S  V  G  T  R  F  P  H  L  K  W  P  T

1441   CGCTTATTTGGCTGAGGCTGTGGCCTGGAAAGGCACTATGGCGTGCTGCGGTACAAGGCC
       GCGAATAAACCGACTCCGACACCGGACCTTTCCGTGATACCGCACGACGCCATGTTCCGG

```
1501    GGGGCTGGCGTACGAACCACGACGCCCGAAGGGAACTCTTCGGTCTTACTACTACTATGT
        CCCCGACCGCATGCTTGGTGCTGCGGGCTTCCCTTGAGAAGCCAGAATGATGATGATACA

501      G  A  G  V  R  T  T  T  P  E  G  N  S  S  V  L  L  L  C
501       G  L  A  Y  E  P  R  R  P  K  G  T  L  R  S  Y  Y  Y  V
501        G  W  R  T  N  H  D  A  R  R  E  L  F  G  L  T  T  T  M  S

1561    CCCCAGTTGACCCCCCGA
        GGGGTCAACTGGGGGGCT

HIGH-THROUGHPUT SCREENING OF EXPRESSED DNA LIBRARIES IN FILAMENTOUS FUNGI

This is a continuation application of prior application Ser. No. 09/834,434, filed Apr. 13, 2001, now U.S. Pat. No. 7,122,330 to which priority under 35 U.S.C. §120 is claimed, which claims the benefit of International Application No. PCT/US00/10199 filed on Apr. 13, 2000 under 35 U.S.C. §371, entitled, "High-Throughput Screening Of Expressed DNA Libraries In Filamentous Fungi" all of which is incorporated in its entirety.

SUMMARY OF THE INVENTION

The invention provides a method for the expression and subsequent screening of DNA libraries, particularly synthetic, genomic, and cDNA libraries, in filamentous fungal hosts. The system employs transformed or transfected filamentous fungal strains which generate transferable reproductive elements, for example by efficient sporulation, in submerged culture. The fungi preferably exhibit a morphology that minimizes or eliminates the formation of entangled mycelia. Particularly preferred fungal strains are also capable of expressing isolatable quantities of exogenous proteins for evaluation. The mutant fungal strains of the invention are particularly well-suited for high-throughput screening techniques, due to their production of transferable reproductive elements, high levels of expression, and very low culture viscosity.

BACKGROUND OF THE INVENTION

Naturally-occurring populations of microorganisms exhibit a wide array of biochemical and metabolic diversity. Due in part to difficulties in isolating and culturing many microorganisms, a vast number of potentially valuable proteins and polypeptides present in these populations have escaped identification. Indeed, it has been estimated that less than one percent of the world's microorganisms have been cultured to date. There remains a pressing need for new approaches to the characterization of proteins, polypeptides and metabolites from as-yet uncultivated, unidentified microorganisms, and also from known microorganisms. (The term "protein" as used hereinafter should be understood to encompass peptides and polypeptides as well.) There also remains a need for new approaches to the identification and isolation of the genes encoding these proteins, so as to enable the modification and/or production of the proteins.

One approach to this problem has been described by Short in U.S. Pat. Nos. 5,958,672; 6,001,574; 6,030,779, and 6,057,103 (the contents of which are incorporated herein by reference). In this approach, a genomic DNA library is prepared directly from an environmental sample (e.g. a soil sample), with or without making an attempt to isolate or culture any organisms that might be present. The DNA library is expressed in *E. coli*, and the expressed proteins are screened for a property or activity of interest. Short alludes to, but does not describe or enable, the use of fungal host cells in this method.

The approach as described suffers from several serious disadvantages, one of which is that *E. coli* does not effectively express genes having introns. Roughly 90% of the species of microorganisms in soil are eukaryotes (principally fungi), which generally do have introns in their genomic DNA. Given that there are already about 100,000 species of eumycotan fungi known, with an estimated 1,000,000 yet to be discovered (B. Kendrick, *The Fifth Kingdom*, Mycologue Publications 1999), the potential for protein and metabolite diversity is far higher among the fungal genomes, but the presence of introns puts most of the fungal protein and metabolite repertoire out of the reach of bacterial expression systems. Not only are many classes of enzymes (e.g., secretory fungal lignin peroxidases and manganese-dependent peroxidases) unique to fungi, but there are many fungal proteins, including enzymes (e.g. lignin peroxidases, *A. niger* invertase), that are glycosylated, and such proteins would not be glycosylated if expressed by *E. coli*. The much higher number and greater size and complexity of fungal genomes, the uniqueness of many fungal proteins, and the glycosylation of many fungal proteins, all indicate that the fraction of microbial protein and metabolite diversity in a given environmental sample that could be actually detected by bacterial expression of genomic DNA is considerably less than 10%.

Due in part to the spread of AIDS and the rising population of organ transplant recipients, there is a growing population of immune-compromised or immuno-supressed individuals, and the number and variety of fungal infections has grown apace (*Infect. Med.* 16:380-382, 385-386 (1999)). There is a need to identify and characterize proteins from pathogenic fungi in the ongoing search for new targets for anti-fungal drugs, which requires the capability to screen DNA libraries derived from fungal genomes. Again, the presence of introns in fungal genomes makes expression of genomic DNA libraries difficult in most currently available bacterial hosts. There has also been a rise in the prevalence of antibiotic-resistant bacterial infections, creating a need for high-throughput screening for new fungal metabolites having antibiotic activity.

Eukaryotic genomes of higher organisms are also too complex for comprehensive expression of DNA libraries in bacteria. When all eukaryotic species are considered, bacteria represent only about 0.3% of all known species (E. O. Wilson, "The Current State of Biological Diversity", in *Biodiversity*, National Academy Press, Washington D.C., 1988, Chapter 1); thus the fraction of the world's genetic diversity accessible to bacterial expression systems is extremely limited.

To avoid problems with introns, it is possible to prepare a cDNA library and express it in bacteria. However, this approach relies upon the presence of RNA transcripts, and any genes not actively being transcribed will not be represented in the library. Many desirable proteins are expressed only under specific conditions (e.g., virulence factors in pathogenic fungi) and these conditions may not exist at the time the mRNA is harvested. Furthermore, in order to obtain sufficient RNA to prepare a cDNA library, it is necessary to culture a fair amount of the organism. For organisms in environmental samples that do not grow well in culture, or novel microorganisms for which appropriate culture conditions are unknown, sufficient RNA will not be readily or reliably obtained. In contrast, sufficient genomic DNA can be obtained from a very small number of individual cells by PCR amplification, using either random primers or primers designed to favor certain classes of genes. Finally, genes that are highly expressed in an organism will tend to be over-represented in the mRNA, and thus over-represented at the expense of minimally-expressed genes in a cDNA library. In order to have a high level of coverage of the mRNA species present, a much larger number of clones must be screened if a cDNA library is employed instead of a genomic library, since the latter will have a more nearly equal representation of the variety of genes present. Clearly it is more desirable to screen a genomic DNA library if at all possible.

Also, *E. coli* is incapable of secretion of many proteins, and thus is undesirable as a host cell for screening purposes where the screening relies upon secretion of the gene product. An additional disadvantage for *E. coli*, and for bacterial hosts in general, is that prokaryotes cannot provide many of the post-translational modifications required for the activity of numerous eukaryotic proteins. In addition to glycosylation, subunit cleavage, disulfide bond formation, and proper folding of proteins are examples of the post-translational processing often required to produce an active protein.

To ensure such processing one can sometimes use mammalian cells, but mammalian cells are difficult to maintain, require expensive media, and are not generally transformed with high efficiency. Such transformation systems are therefore not convenient for high-throughput screening of proteins, although efforts have been made to employ mammalian cells as hosts for cDNA library screening (Schouten et al., WO 99/64582). An approach involving fusion of transformed protoplasts with mammalian cells prior to library screening has been described (U.S. Pat. No. 5,989,814), but expression of the protein library occurs in bacteria or yeast prior to cell fusion. There have been efforts to modify glycosylation patterns enzymatically after expression in host cells (Meynial-Salles and Combes, *J. Biotechnol.*, 46:1-14 (1996)), but such methods must be tailored for specific products and are not suitable for expression of proteins from a DNA library. More recently, Maras et al., *Eur. J. Biochem.*, 249:701-707 (1997) (see also U.S. Pat. No. 5,834,251) have described a strain of *Trichoderma reesei* engineered to express human GlcNAc transferase I. The enzyme transfers N-acetylglucosamine to mannose residues on other expressed exogenous proteins, a first step toward more closely approximating natural mammalian products.

The use of yeast as host cells solves some of the above problems, but introduces others. Yeast tend to hyper-glycosylate exogenous proteins (Bretthauer and Castellino, 1999, *Biotechnol. Appl. Biochem.* 30:193-200), and the altered glycosylation patterns often render expressed mammalian proteins highly antigenic (C. Ballou, in *Molecular Biology of the Yeast Sacccharomyces*, J. Strathern et al., eds., Cold Spring Harbor Laboratory Press, NY, 1982, 335-360). Although yeast are capable of coping with a limited number of introns, they are not generally capable of handling complex genes from higher species such as vertebrates. Even genes from filamentous fungi are usually too complex for yeast to transcribe efficiently, and this problem is compounded by differences in expression and splicing sequences between yeast and filamentous fungi (see e.g., M. Innis et al., *Science* 1985 228:21-26). Despite these drawbacks, transformation and expression systems for yeast have been extensively developed, generally for use with cDNA libraries. Yeast expression systems have been developed which are used to screen for naturally secreted and membrane proteins of mammalian origin (Klein, et al., *Proc. Natl. Acad. Sci. USA* 1996 93:7108-7113; Treco, U.S. Pat. No. 5,783,385), and for heterologous fungal proteins (Dalboge and Heldt-Hansen, *Mol. Gen. Genet.* 243:253-260 (1994)) and mammalian proteins (Tekamp-Olson and Meryweather, U.S. Pat. No. 6,017,731).

The term "yeast" as used in the context of yeast expression systems generally refers to organisms of the order *Saccharomycetales*, such as *S. cerevisiae* and *Pichia pastoris*. For the purposes of this disclosure, the terms "fungi" and "fungal" should be understood to refer to *Basidiomycetes, Zygomycetes, Oomycetes*, and *Chythridiomycetes*, and *Ascomycetes* of the class *Euascomycetes*, which are not of the order *Saccharomycetales*. Filamentous fungi may be distinguished from yeast by their hyphal elongation during vegetative growth, and obligately aerobic carbon catabolism (vegetative growth in yeast is accomplished by budding from a unicellular thallus, and yeast may employ fermentative catabolism.)

Proper intron splicing, and glycosylation, folding, and other post-translational modifications of fungal gene products would be most efficiently handled by a fungal host species, making filamentous fungi superior hosts for screening genomic DNA from soil samples. It also makes them excellent hosts for the production of fungal enzymes of commercial interest, such as proteases, cellulases, and amylases. It has also been found that filamentous fungi are capable of transcribing, translating, processing, and secreting the products of other eukaryotic genes, including mammalian genes. The latter property makes filamentous fungi attractive hosts for the production of proteins of biomedical interest. Glycosylation patterns introduced by filamentous fungi more closely resemble those of mammalian proteins than do the patterns introduced by yeast. For these reasons, a great deal of effort has been expended on the development of fungal host systems for expression of heterologous proteins, and a number of fungal expression systems have been developed. For reviews of work in this area, see Maras et al., *Glycoconjugate J.*, 16:99-107 (1999); Peberdy, *Acta Microbiol. Immunol. Hung.* 46:165-174 (1999); Kruszewsa, *Acta Biochim. Pol.* 46:181-195 (1999); Archer et al., *Crit. Rev. Biotechnol.* 17:273-306 (1997); and Jeenes et al., *Biotech. Genet. Eng. Rev.* 9:327-367 (1991).

High-throughput expression and assaying of DNA libraries derived from fungal genomes would also be of use in assigning functions to the many mammalian genes that are currently of unknown function. For example, once a fungal protein having a property of activity of interest is identified, the sequence of the encoding gene may be compared to the human genome sequence to look for homologous genes.

Yelton et al., U.S. Pat. No. 4,816,405, discloses the modification of filamentous Ascomycetes to produce and secrete heterologous proteins. Buxton et al., in U.S. Pat. No. 4,885,249, and in Buxton and Radford, *Mol. Gen. Genet.* 196:339-344 (1984), discloses the transformation of *Aspergillus niger* by a DNA vector that contains a selectable marker capable of being incorporated into the host cells. McKnight et al., U.S. Pat. No. 4,935,349, and Boel, in U.S. Pat. No. 5,536,661, disclose methods for expressing eukaryotic genes in *Aspergillus* involving promoters capable of directing the expression of heterologous genes in *Aspergillus* and other filamentous fungi. Royer et al., in U.S. Pat. No. 5,837,847, and Berka et al., in WO 00/56900, disclose expression systems for use in *Fusarium venenatum* employing natural and mutant *Fusarium* spp. promoters. Conneely et al., in U.S. Pat. No. 5,955,316, disclose plasmid constructs suitable for the expression and production of lactoferrin in *Aspergillus*. *Cladosporium* glucose oxidase had been expressed in *Aspergillus* (U.S. Pat. No. 5,879,921).

Similar techniques have been used in *Neurospora*. Lambowitz, in U.S. Pat. No. 4,486,533, discloses an autonomously replicating DNA vector for filamentous fungi and its use for the introduction and expression of heterologous genes in *Neurospora*. Stuart et al. describe co-transformation of *Neurospora crassa* spheroplasts with mammalian genes and endogenous transcriptional regulatory elements in U.S. Pat. No. 5,695,965, and an improved strain of *Neurospora* having reduced levels of extracellular protease in U.S. Pat. No. 5,776,730. Vectors for transformation of *Neurospora* are disclosed in U.S. Pat. No. 5,834,191. Takagi et al. describe a transformation system for *Rhizopus* in U.S. Pat. No. 5,436,158. Sisniega-Barroso et al. describe a transformation system for filamentous fungi in WO 99/51756, which employs promoters of the glutamate dehydrogenase genes from *Aspergillus awamori*. Dantas-Barbosa et al., *FEMS Microbiol. Lett.* 1998 169:185-190, describe transformation of *Humicola grisea* var. *thermoidea* to hygromycin B resistance, using either the lithium acetate method or electroporation.

Among the more successful fungal expression systems are those of *Aspergillus* and *Trichoderma*, for example as disclosed by Berka et al. in U.S. Pat. No. 5,578,463; see also Devchand and Gwynne, *J. Biotechnol.* 17:3-9 (1991) and Gouka et al., *Appl. Microbiol. Biotechnol.* 47:1-11 (1997). Examples of transformed strains of *Myceliophthora thermophila, Acremonium alabamense, Thielavia terrestris* and *Sporotrichum cellulophilum* are presented in WO 96/02563 and U.S. Pat. Nos. 5,602,004, 5,604,129 and 5,695,985, which describe certain drawbacks of the *Aspergillus* and *Trichoderma* systems and suggest that other fungi may be more suited to large scale protein production. Methods for the transformation of phyla other than Ascomycetes are known in the art; see for example Munoz-Rivas et al., *Mol. Gen. Genet.* 1986 205:103-106 (*Schizophyllum commune*); van de Rhee et al., *Mol. Gen. Genet.* 1996 250:252-258 (*Agaricus bisporus*); Amau et al., *Mol. Gen. Genet.* 1991 225:193-198 (*Mucor circinelloides*); Liou et al., *Biosci. Biotechnol. Biochem.* 1992 56:1503-1504 (*Rhizopus niveus*); Judelson et al., *Mol. Plant Microbe Interact.* 1991 4:602-607 (*Phytophthora infestans*); and de Groot et al., *Nature Biotechnol.* 1998 16:839-842 (*Agaricus bisporus*).

In addition to the usual methods of transformation of filamentous fungi, such as for example protoplast fusion, Chakraborty and Kapoor, *Nucleic Acids Res.* 18:6737 (1990) describe the transformation of filamentous fungi by electroporation. De Groot et al., in *Nature Biotechnol.* 16: 839-842 (1998), describe *Agrobacterium tumefaciens*-mediated transformation of several filamentous fungi. Biolistic introduction of DNA into fungi has been carried out; see for example Christiansen et al., Curr. Genet. 29:100-102 (1995); Durand et al., *Curr. Genet.* 31:158-161 (1997); and Barcellos et al., *Can. J. Microbiol.* 44:1137-1141 (1998). The use of magnetic particles for "magneto-biolistic" transfection of cells is described in U.S. Pat. Nos. 5,516,670 and 5,753,477, and is expected to be applicable to filamentous fungi.

It is evident that much work has been done to develop expression systems using fungi as hosts. However, the common fungal hosts are all filamentous fungi, which tend to form entangled mats of mycelia in unstirred cultures, and highly viscous suspension (submerged) cultures in stirred tank bioreactors. These properties of filamentous fungi also cause some problems in the industrial production of enzymes in fungal host cells. For example, high viscosity and/or the local formation of dense aggregates of mycelium, leads to difficulties in agitation, aeration, and nutrient diffusion. In general, filamentous fungi are not amenable to micropipetting of suspension cultures into microtiter plates, due to the viscosity of the cultures. Furthermore, due to the entangled mycelia, a culture of a typical filamentous fungus expressing a DNA library is not easily separated into separate clones on a large scale, which prevents evaluation of the individual genotypes as would be required in a high-throughput assay system.

Typical filamentous fungi, in the absence of constant agitation, tend to grow in the form of mats on the surface of a liquid culture medium, where they produce aerial spores. They do not generally sporulate when in submerged culture. Both of these properties present substantial obstacles to the culture of filamentous fungal clones in mircotiter plates, and to the efficient manipulation and use of such cultures for high-throughput screening. Suspended spores or other reproductively competent elements would suitable for separation and distribution into individual microtiter wells, whereas the production of aerial spores will lead to cross-contamination of microtiter wells if surface mats are allowed to form. Agitation of the medium in microtiter wells, to the extent needed to prevent mat formation, is not feasible. In addition to the problem of difficult-to-control aerial spores, surface mats interfere with light transmission, making many assays (in particular spectrophotometric absorbance assays) diffcult or impossible. Surface mats also interfere with processes such as oxygenation, reagent and nutrient addition, and pipetting.

The influence of fungal morphology on the physical properties of the culture has been recognized, and naturally-occurring strains having more favorable morphology have been identified, as described for example by Jensen and Boominathan in U.S. Pat. No. 5,695,985. Homogeneous distribution of loose mycelium, with pronounced branching, was described as a particularly desirable morphology. Schuster and Royer, in international patent application WO 97/26330 and U.S. Pat. No. 6,184,026, suggest a similar method of identifying fungal cells having more suitable morphology for industrial production of heterologous proteins. The method comprises screening mutants of a parent fungal cell line, rather than wild-type strains, to find a specific altered morphology, transforming the mutant, and assessing whether a culture of the transformed mutant produces more heterologous protein than the parent cell line. Mutants with at least 10% greater hyphal branching are particulary claimed. The method is illustrated for strains of *Trichoderma, Fusarium* and *Aspergillus*, and is suggested to be applicable to numerous other genera.

The effect of branching frequency on culture viscosity of *Aspergillus oryzae* mutants was examined by Bocking et al., *Biotechnol. Bioeng.* 65:638-648 (1999); more highly branched strains exhibited lower viscosity in this study. Van Wezel et al., in PCT application WO 00/00613, describe methods for reducing the branching and/or enhancing the fragmentation of filamentous microorganisms, whereby the viscosity of the culture is reduced. The method involves transforming the microorganisms with the SsgA gene of *Streptomyces griseus*. The method is demonstrated in filamentous bacteria of the order Actinomycetales, but is stated to be applicable to filamentous fungi. Dunn-Coleman et al., in WO 00/56893, describe an HbrA2 mutant *A. nidulans*, which exhibits a hyperbranched phenotype when grown above 42° C., and noted a linear relationship between the degree of hyphal branching and culture viscosity.

Most prior efforts in the field of filamentous fungal expression systems have been directed to the identification of strains suitable for industrial production of enzymes, and therefore attention has been focused on culture viscosity, stability of transformation, yield of heterologous protein per unit volume, and yield as a percentage of biomass. DNA libraries have been expressed in fungi; see for example Gems and Clutterbuck, *Curr. Genet.* 1993 24:520-524, where an *Aspergillus nidulans* library was expressed in *A nidulans* and Gems et al., *Mol. Gen. Genet.* 1994 242:467-471 where a genomic library from *Penicillium* was expressed in *Aspergillus*. Neither of these reports disclosed or suggested screening the expressed proteins; it was through complementation of mutant alleles in the host that the expression of genes from the DNA library was demonstrated. The complementation method requires a specific mutant host for each exogenous protein activity one wishes to detect, and does not provide a tool for general library screening.

The cloning of an *Aspergillus niger* invertase gene by expression in *Trichoderma reesei* was described by Berges et al., *Curr. Genet.* 1993 24:53-59. Using an *A. niger* genomic library constructed in a cosmid vector containing a selectable marker, and using as the host *T reesei* (which is incapable of utilizing sucrose), an *A. niger* invertase gene was cloned by a sib selection procedure. Here, again, a very specific characteristic of the host was required to detect the presence of a single expressed exogenous protein, and screening of the genomic library was not disclosed or enabled.

The characteristics of a fungal host cell suitable for expression of a DNA library are different in many respects from the characteristics of hosts suitable for industrial protein manufacture. In general terms, a suitable fungal host for high-throughput screening should meet numerous criteria; among them are the following:

The host must be transformed with high efficiency.

The host must process intron-containing genes and carry out any necessary splicing.

The host must post-translationally process the expressed protein so that it is produced in an active form.

Where the library is to be assayed for a protein, the host must produce the protein in high enough yield for detection by the assay.

The host should accept a variety of expression regulatory elements, for ease of use and versatility.

The host should permit the use of easily-selectable markers.

The host cell cultures should be of low viscosity.

The host should be deficient in proteases and/or be amenable to suppression of protease expression.

The host must permit screens for a wide variety of exogenous protein activities or properties.

The hyphae in a culture of the host fungus should not be so entangled as to prevent the isolation of single clones, and should not be so entangled as to raise the viscosity to the point of preventing efficient transfer and replication in a miniaturized high throughput screening format (e.g. by micropipeting).

The host should not form surface mats, but should preferentially grow as a submerged culture.

The host should allow the efficient production of submerged spores or other propagules under the growth conditions provided in the high throughput screen.

In cases where metabolites are being screened for, it would be advantageous if the host cells secreted the metabolites into the medium, where they could be readily detected and/or assayed. Ideally, the host should secrete only the exogenous protein.

In cases where a protein is being assayed for, it would be particularly advantageous if the host also expressed enough heterologous protein to enable isolation and purification of the protein. A host cell with this characteristic would make it possible to further characterize all heterologous proteins of interest merely by culturing the host cells, without the time-consuming molecular biological manipulations need to transfer the gene to another organism. Preferably, the host should be capable of secretion of the protein, as this would permit more reliable and more varied assays.

It would also be advantageous if the host cell were amenable to ready isolation of the heterologous DNA, so that further studies and modifications of the gene itself may be carried out.

In addition to these qualities of the host, the transformation system should also exhibit certain characteristics. The transformation frequency should be sufficiently high to generate the numbers of transformants required for meaningful screens. Ideally, expression of the exogenous protein will be induced by a single inducer, by a single pathway, acting on a single promoter.

To date, no combination of host cells and transformation system has been developed that meets all, or even most, of these criteria. A need therefore remains for fungal host cell and transformation systems that are capable of efficiently expressing the gene products of a DNA library, especially genomic and/or eukaryotic genomic DNA libraries.

BRIEF DESCRIPTION OF THE INVENTION

The present invention employs filamentous fungi which produce "transferable reproductive elements" when grown in submerged culture. By "transferable reproductive element" is meant a spore, propagule, hyphal fragment, protoplast, micropellet, or other fungal element that is (1) readily separated from other such elements in the culture medium, and (2) capable of reproducing itself into a monoclonal culture. The fungi preferably also exhibit a less pronounced filamentous phenotype and/or a compact growth morphology, and produce low-viscosity cultures that are suitable for the physical manipulations involved in high-throughput DNA library screening. Particularly preferred are filamentous fungi which, even in the absence of agitation, tend to grow as submerged cultures rather than as surface mats.

The present invention takes advantage of the properties of the transformation system disclosed in international patent applications PCT/NL99/00618 and PCT/EP99/2025 16. These applications describe an efficient transformation system for filamentous fungal hosts such as *Chrysosporium lucknowense* and *Aspergillus sojae*. These applications also disclose that mutant strains are readily prepared which retain all the advantages of the wild-type host cells, but which have partially lost their filamentous phenotype and thus provide low-viscosity cultures.

The fungi preferred for use in the invention express and secrete large amounts of exogenous protein, producing a high protein/biomass ratio relative to previously known filamentous fungal hosts. The invention provides a transformation system that exhibits high yields of transformants. The invention also provides libraries of transformant fungi which efficiently express the protein products of heterologous cDNA inserts, and especially genomic DNA inserts. In another aspect of the invention, the libraries of transformed fungi may be used in screening for activities or properties of the heterologous proteins, or in screening for metabolites produced by the transformed fungi as a consequence of exogenous protein activities, or in screening for the heterologous DNA or for RNA transcripts derived therefrom. It will be appreciated that the present invention also enables high-throughput screening for metabolites of non-transformed strains having the phenotypic characteristics described above.

The term "mutant filamentous fungus" as used herein refers simply to fungi not found in nature. The "mutations" that lead to desirable phenotypic characteristics, such as a compact growth form, low viscosity, reduced protease levels, submerged growth, etc., may be introduced randomly by either classical means, such as UV irradiation and chemical mutagenesis, or by molecular biological methods such as cassette mutagenesis, or may be deliberately introduced by genetic engineering methods. Should a naturally-occurring fungus be found to possess the necessary properties, it will of course be usable in the methods of the invention.

In yet another aspect of the invention, the libraries of transformed fungi may be screened for useful properties of the fungi themselves, such as for example high levels of production of a particular expressed protein or metabolite. This aspect of the invention is illustrated by a quantitative assay for the expressed protein of interest, where the particular transformant having the most favorable combination of protein production, protein processing, and protein secretion would be detected.

In another aspect of the invention, the libraries of transformed fungi may be screened for the presence of DNA sequences capable of hybridizing to a nucleic acid probe of interest.

DESCRIPTION OF THE FIGURES

FIGS. 15A-F present sequencing results of the pyrE gene. Underlining indicates amino acid sequence; it is not continuous due to some sequence uncertainties. The indicated amino acids are the most probable. Bold type indicates putative/probable introns.

DETAILED DESCRIPTION OF THE INVENTION

Figure 1:
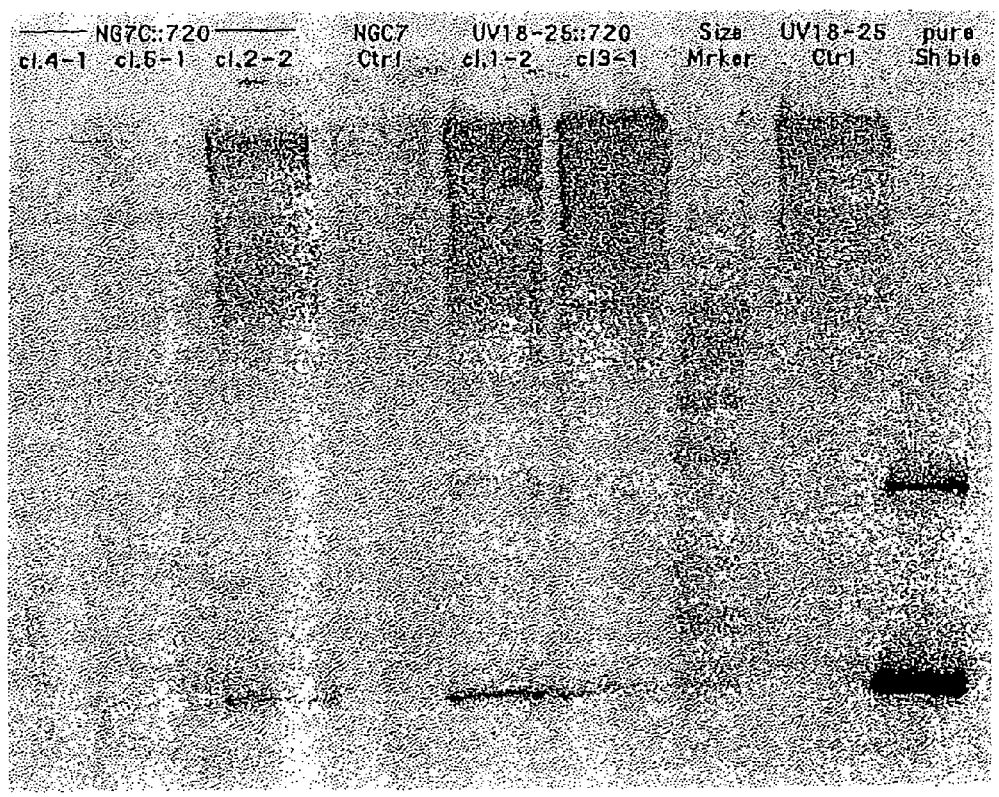
FIG. 1 is a Western blot as described in the Examples.

In its broadest aspect, the invention is directed to transformed filamentous fungi that generate transferable reproductive elements in suspension, to libraries of such fungi, and to methods of screening such libraries for biological properties of interest, such as biochemical or biological activity associated with expressed exogenous proteins or associated with metabolites, i.e. small molecule products produced by endgoenous and/or exogenous enzymes.

The library of low-viscosity filamentous fungi comprises fungi containing nucleic acid sequences, each nucleic acid sequence encoding a heterologous protein, each of said nucleic acid sequences being operably linked to an expression regulating region and optionally a secretion signal encoding sequence and/or a carrier protein encoding sequence. Preferably a transformed strain according to the invention will secrete the heterologous protein.

The expression and screening methods of the invention, and the fungi employed therein, are useful for producing fungi, proteins, metabolites, and DNA molecules having utility in a variety of applications. The methods of the invention are also useful for producing nucleic acid and protein sequence information, and this information itself is regarded as a valuable product of the claimed methods.

Preferred filamentous fungi of the invention are characterized by the low viscosity of the culture medium. Whereas a typical industrial-grade filamentous fungus will produce cultures with viscosities well over 200 centipoise (cP) and usually over 1,000 cP, and can reach 10,000 cP, the fungi of this invention exhibit a culture viscosity of less than 200 cP, preferably less than 100 cP, more preferably less than 60 cP, and most preferably less than 10 cP after 48 or more hours of culturing in the presence of adequate nutrients under optimal or near-optimal growth conditions. The filamentous fungi of the invention usually exhibit a morphology characterized by short, discrete, non-entangled hyphae, or micropellets. Micropellets are slightly- or non-entangled collections of hyphae arising from a single clone, as distinct from pellets which are much larger and are derived from multiple entangled clones. For example, the mutant UV18-25 *Chrysosporium lucknowense* strain (viscosity <10 cP) and the morphologically similar mutant *Trichoderma longibrachiatum* X-252 strain (viscosity <60 cP) are characterised by the presence of short, distinct, non-entangled hyphae between 100 and 200 microns in length, and the low viscosity engineered mutant *Aspergillus sojae* pclA is characterized by a compact form with considerable branching and short hyphae (see FIG. 14). Whereas the low-viscosity fungi described in WO97/26330 are described as having "more extensive hyphal branching," some fungi of the present invention have equivalent or even slightly reduced hyphal branching when compared to the non-mutant strains. It appears that hyphal length plays the dominant role in controlling the viscosity of the culture.

Particularly preferred fungal strains are characterized by having a high exogenous secreted protein/biomass ratio. This ratio is preferably greater than 1:1, more preferably greater than 2:1, and even more preferably 6:1 or greater. Most preferably, the ratio is 8:1 or higher. Such high ratios are advantageous in a high-throughput screening environment, because they result in a higher concentration of exogenous protein, allowing more sensitive and/or more rapid screening assays. This is of particular benefit as the volume of the assay solution decreases, for example upon going from 96-well plates to 384-well plates, and thence to 1536-well plates. The methods of the present invention are suitable for any of these microtiter plate formats, and for most other HTS formats employing liquid samples.

It is contemplated that any filamentous fungus can be converted, by the processes of mutation described herein, into mutant strains suitable for use in the present invention. Among the preferred genera of filamentous fungi are the *Chrysosporium, Thielavia, Neurospora, Aureobasidium, Filibasidium, Piromyces, Cryplococcus, Acremonium, Tolypocladium, Scytalidium, Schizophyllum, Sporotrichum, Penicillium, Gibberella, Myceliophthora, Mucor, Aspergillus, Fusarium, Humicola,* and *Trichoderma,* and anamorphs and teleomorphs thereof. More preferred are *Chrysosporium, Trichoderma, Aspergillus,* and *Fusarium.* Most preferred is *Chrysosporium.* The genus and species of fungi can be defined by morphology consistent with that disclosed in Barnett and Hunter, *Illustrated Genera of Imperfect Fungi,* 3rd Edition, 1972, Burgess Publishing Company. A source providing details concerning classification of fungi of the genus *Chrysosporium* is Van Oorschot, C.A.N. (1980) "A revision of *Chrysosporium* and allied genera" in Studies in Mycology No. 20, Centraal Bureau voor Schimmelcultures (CBS), Baarn, The Netherlands, pp. 1-36. According to these teachings the genus *Chrysosporium* falls within the family *Moniliaceae* which belongs to the order *Hyphomycetales.*

Another ready source providing information on fungal nomenclature are the Budapest Treaty depositories, especially those providing online databases (the following internet addresses employ the http protocol). ATCC (US) provides information which may be accessed on the World Wide Web (HTTP protocol) at atcc.org. CBS (NE) also has a website located on the World Wide Web (HTTP protocol) at cbs.knaw.nl providing relevant information. -VKM (RU) in Moscow is also a reliable source of information located on the World Wide Web (HTTP protocol) at bdt.org.br.bdt.msdn.vkm/general. Another source is the United States Department of Agriculture Research Service website (located on an NT webserver rather than the World Wide Web at ars-grin.gov/fungaldatabases. All these institutions can provide teaching on the distinguishing characteristics of fungal species. An alternate taxonomy of the *Ascomycota* may be found on the World Wide Web (HTTP protocol) at ncbi.nlm.nih.gov/htbin-post/Taxonomy/wgetorg?mode=Undef&id=4890. According to this alternate taxonomy, the genus *Chrysosporium* belongs to family Onygenaceae, order Onygenales, phylum Ascomycota.

The definition of *Chrysosporium* includes but is not limited to these strains: *C. botryoides*, *C. carmichaelii*, *C. crassitunicatum*, *C. europae*, *C. evolceannui*, *C. farinicola*, *C. fastidium*, *C. filiforme, C. georgiae, C. globiferum, C. globiferum* var. *articulatum, C. globiferum* var. *niveum, C. hirundo, C. hispanicum, C. holmii, C. indicum, C. inops, C. keratinophilum, C. kreiselii, C. kuzurovianum, C. lignorum, C. lobatum, C. lucknowense, C. lucknowense* Garg 27K, *C. medium, C. medium* var. *spissescens, C. mephiticum, C. merdarium, C. merdarium* var. *roseum, C. minor, C. pannicola, C. parvum, C. parvum* var. *crescens, C. pilosum, C. pseudomerdarium, C. pyriformis, C. queenslandicum, C. sigleri, C. sulfureum, C. synchronum, C. tropicum, C. undulatum, C. vallenarense, C. vespertilium, C. zonatum.*

*C. lucknowense* is a species of *Chrysosporium* that is of particular interest as it has provided a natural high producer of cellulase proteins (international applications WO 98/15633, PCT/NL99/00618, and U.S. Pat. Nos. 5,811,381 and 6,015,707). Strains with international depository accession numbers ATCC 44006, CBS 251.72, CBS 143.77, CBS 272.77, and VKM F-3500D are examples of *Chrysosporium lucknowense* strains. Also included within the definition of *Chrysosporium* are strains derived from *Chrysosporium* predecessors including those that have mutated either naturally or by induced mutagenesis. The methods of the invention, in one embodiment, employ mutants of *Chrysosporium*, obtained by a combination of irradiation and chemically-induced mutagenesis, that tend to produce transferable reproductive elements in suspension, and that exhibit a morphology characterized by short, discrete, non entangled hyphae ("compact growth"), and a phenotype characterized by submerged growth and reduced viscosity of the fermentation medium when cultured in suspension. In another embodiment, the invention employs phenotypically similar mutants of *Trichoderma*. In yet other embodiments the invention employs phenotypically similar mutants of *Aspergillus sojae* or *Aspergillis niger.*

For example, VKM F-3500D (strain "C1") was mutagenised by subjecting it to ultraviolet light to generate strain UV13-6. This strain was subsequently further mutated with N-methyl-N'-nitro-N-nitrosoguanidine to generate strain NG7C-19. The latter strain in turn was subjected to mutation by ultraviolet light resulting in strain UV18-25 (VKM F-3631D). During this mutation process the morphological characteristics varied somewhat in culture in liquid or on plates as well as under the microscope. With each successive mutagenesis the cultures showed less of the fluffy and felty appearance on plates that are described as being characteristic of *Chrysosporium*, until the colonies attained a flat and matted appearance. A brown pigment observed with the wild type strain in some media was less prevalent in mutant strains. In liquid culture the mutant UV18-25 was noticeably less viscous than the wild type strain C1 and the mutants UV13-6 and NG7C-19. While all strains maintained the gross microscopic characteristics of *Chrysosporium*, the mycelia became narrower with each successive mutation and with UV18-25 distinct fragmentation of the mycelia could be observed. This mycelial fragmentation is likely to be a cause of the lower viscosity associated with cultures of UV18-25. The capacity of the strains for aerial sporulation decreased with each mutagenic step. These results demonstrate that a strain may belong genetically to the genus *Chrysosporium* while exhibiting deviations from the traditional taxonomic (morphological) definitions.

In particular the anamorph form of *Chrysosporium* has been found to be suited for the screening application according to the invention. The metabolism of the anamorph renders it particularly suitable for a high degree of expression. A teleomorph should also be suitable as the genetic make-up of the anamorphs and teleomorphs is identical. The difference between anamorph and teleomorph is that one is the asexual state and the other is the sexual state; the two states exhibit different morphology under certain conditions.

Another example embodies genetically engineered mutant strains of *Aspergillus sojae*. In one of these mutants a specific endoprotease encoding gene was disrupted. This resulted in a compact growth phenotype exhibiting enhanced branching and short hyphae, and the formation of micropellets in submerged cultivation. Moreover, the *Aspergillus sojae* referred to in this application may be induced to exhibit efficient sporulation under specific submerged cultivation conditions, which renders it especially suitable for use in a high-throughput screening system. In this case, the conditions conducive to formation of the transferable reproductive elements simply consisted of a synthetic medium containing 0.6 g/ml EDTA. The conducive conditions will vary from one host to another, but it is evident that the conditions will already be known if a host has been found to be suitable.

It is preferable to use non-toxigenic and non-pathogenic fungal strains, of which a number are known in the art, as this will reduce risks to the practitioner and will simplify the overall screening process. In a preferred embodiment the fungi will also be protease deficient, so as to minimize degradation of the exogenous proteins, and/or amenable to suppression of protease production. The use of protease deficient strains as expression hosts is well known; see for example PCT application WO 96/29391. Protease deficient strains may be produced by screening of mutants, or the protease gene(s) may be "knocked out" or otherwise inactivated by methods known in the art, as described for example by Christensen and Hynes in U.S. Pat. No. 6,025,185 (*Aspergillus oryzae* with non-functional areA gene).

It has been found that *Chrysosporium* mutants can be made that have reduced expression of protease, thus making them even more suitable for the production of proteinaceous products, especially if the proteinaceous product is sensitive to protease activity. Thus the invention my also employ a mutant *Chrysosporium* strain which produces less protease than non-mutant *Chrysosporium* strain, for example less than *C. lucknowense* strain C1 (VKM F-3500 D). In particular the protease acitivity (other than any selective protease intended to cleave a secreted fusion protein) of such strains is less than half the amount, more preferably less than 30% of the amount, and most preferably less than about 10% the amount produced by the C1 strain. The decreased protease activity can be measured by known methods, such as by measuring the halo formed on skim milk plates or by bovine serum albumin (BSA) degradation.

It may be desirable to inactivate other genes in the host filamentous fungus, such as for example those encoding cellulases and other heavily secreted proteins, in order to minimize interference in the assay by host proteins. The genes encoding secreted proteins may be deleted or mutated, or alternatively genes controlling the induction system or other pathways involved in the expession of unwanted proteins may be modified in such a way as to reduce such expression. Where an endogenous promoter is employed in the vectors of the invention (see below), it may be especially desirable to inactivate genes for other proteins under control of the same inducer. Fungi amenable to suppression of protease secretion are those where protease expression is under the control of a regulatory element that responds to environmental conditions, such that these conditions (e.g., amino acid concentration) can be manipulated to minimize protease production.

Preferably a homologous expression-regulating region enabling high expression in the selected host is employed in the transforming vector. High expression-regulating regions derived from a heterologous host, such as from *Trichoderma* or *Aspergillus*, are well known in the art and can also be used. By way of example, and not limitation, examples of proteins known to be expressed in large quantities and thus providing suitable expression regulating sequences for use in the present invention are hydrophobin, protease, amylase, xylanase, pectinase, esterase, beta-galactosidase, cellulase (e.g. endo-glucanase, cellobiohydrolase) and polygalacturonase.

An expression-regulating region comprises a promoter sequence operably linked to a nucleic acid sequence encoding the protein to be expressed. The promoter is linked such that the positioning vis-à-vis the initiation codon of the sequence to be expressed allows expression. The promoter sequence can be constitutive but preferably is inducible. Use of an inducible promoter and appropriate induction media favors expression of genes operably linked to the promoter. Any expression regulating sequence from a homologous species, or from a heterologous strain capable of permitting expression of a protein, is envisaged. The expression regulating sequence is suitably a fungal expression-regulating region, e.g. an ascomycete regulating region. Suitably the ascomycete expression regulating region is a regulating region from any of the following genera: *Aspergillus, Trichoderma, Chrysosporium, Humicola, Neurospora, Tolypocladium, Fusarium, Penicillium, Talaromyces*, or alternative sexual forms thereof such as *Emericela* and *Hypocrea*. The cellobiohydrolase promoter from *Trichoderma*; alcohol dehydrogenase A, alcohol dehydrogenase R, glutamate dehydrogenase, TAKA amylase, glucoamylase, and glyceraldehyde phosphate dehydrogenase promoters from *Aspergillus*; phosphoglycerate and cross-pathway control promoters of *Neurospora*; lipase and aspartic proteinase promoter of *Rhizomucor miehei*; beta-galactosidase promoter of *Penicillium canescens*; and cellobiohydrolase, endoglucanase, xylanase, glyceraldehyde-3-phosphate dehydrogenase A, and protease promoters from *Chrysosporium* are representative examples. An expression regulating sequence from the same genus as the host strain is preferable, as it is more likely to be specifically adapted to the host.

Natural expression-regulating sequences from strains of *Chrysosporium* which express proteins in extremely large amounts, are particularly preferred. Examples of such strains have been deposited in accordance with the Budapest Treaty with the All Russian Collection (VKM) depository institute in Moscow. Wild type C1 strain has the number VKM F-3500 D, deposit date 29 Aug. 1996, C1 UV13-6 mutant was deposited with number VKM F-3632 D, and deposit date 2 Sep. 1998, C1 NG7C-19 mutant was deposited with number VKM F-3633 D and deposit date 2 Sep. 1998 and C1 UV18-25 mutant was deposited with number VKM F-3631 D and deposit date 2 Sep. 1998. These strains are also preferred as sources for the generation of low-viscosity mutants; indeed the VKM F-3631 D strain already exhibits the necessary low viscosity phenotype. A low-viscosity mutant *Trichoderma* strain, designated X-252, was obtained after two rounds of irradiation of *Trichoderma longibrachiatum* 18.2KK, which in turn was derived by mutation of the QM 9414 strain of *T. longibrachiatum* (ATCC 26921). In other embodiments the invention employs phenotypically similar mutants of *Aspergillus sojae* and *Aspergillus niger*.

Preferably, where the host is a *Chrysosporium*, a *Chrysosporium* promoter sequence is employed to ensure good recognition thereof by the host. Certain heterologous expression-regulating sequences also work as efficiently in *Chrysosporium* as native *Chrysosporium* sequences. This allows well-known constructs and vectors to be used in transformation of *Chrysosporium*, and offers numerous other possibilities for constructing vectors enabling good rates of transformation and expression in this host. For example, standard *Aspergillus* transformation techniques can be used as described for example by Christiansen et al. in *Bio/Technology* 1988 6:1419-1422. Other documents providing details of *Aspergillus* transformation vectors, e.g. U.S. Pat. Nos. 4,816,405, 5,198,345, 5,503,991, 5,364,770, 5,705,358, 5,728,547, and 5,578,463, EP-B-215.594 (also for *Trichoderma*) and their contents are incorporated by reference. As extremely high expression rates for cellulase have been observed in *Chrysosporium* strains, the expression regulating regions of cellulase genes are particularly preferred.

The vectors of the invention can comprise a promoter sequence derived from a gene encoding an enzyme, preferably a secreted enzyme. Examples of suitable enzymes from which promoter sequences may be taken are the carbohydrate-degrading enzymes (e.g., cellulases, xylanases, mannanases, mannosidases, pectinases, amylases, e.g. glucoamylases, α-amylases, α- and β-galactosidases, α- and β-glucosidases, α-glucanases, chitinases, chitanases), proteases (endoproteases, amino-proteases, amino-and carboxypeptidases), other hydrolases (lipases, esterases, phytases), oxidoreductases (catalases, glucose-oxidases) and transferases (transglycosylases, transglutaminases, isomerases and invertases). Several examples from *Chrysosporium lucknowense* are presented in Table A.

A nucleic acid construct will preferably comprise a nucleic acid expression regulatory region from *Chrysosporium*, more preferably from *Chrysosporium lucknowense* or a derivative thereof, operably linked to a nucleic acid sequence encoding a protein to be expressed. Particularly preferred nucleic acid constructs will comprise an expression regulatory region from *Chrysosporium* associated with cellulase or xylanase expression, preferably cellobiohydrolase expression, most preferably expression of the 55 kDa cellobiohydrolase (CBH1) described in Table A. As additional examples, the *Chrysosporium* promoter sequences of hydrophobin, protease, amylase, xylanase, esterase, pectinase, beta-galactosidase, cellulase (e.g. endoglucanase, cellobiohydrolase) and polygalacturonase are also considered to fall within the scope of the invention.

TABLE A

Characteristics of selected enzymes from *Chrysosporium lucknowense*

| Sample | No. of amino acids | Highest pH at which >50% activity is retained | | | Highest pH at which >70% activity is retained | | | Stability 20 h, 50° C. pH 7.5/8 % of max activity remaining |
|---|---|---|---|---|---|---|---|---|
| | | CMCase | RBB CMCase | Other substrates | CMCase | RBB CMCase | Other substrates | |
| 30 Kd alkaline protease | | — | — | 12.5 | — | — | 12.0 | — |
| 30 kD Xyl (alkaline) | 333 | — | — | 10.0 | — | — | 8.5 | 80 |
| 51 kD Xyl | | — | — | 8.0 | — | — | 7.5 | — |
| 60 kD Xyl | | — | — | 9.5 | — | — | 9.0 | 85 |
| 30 kD endo (EG3) | 247 | | | | | | | |
| 45 kD endo | | 7.0 | 8.0 | — | 6.5 | 7.0 | — | 75 |
| 55 kD endo | 247 | 8.0 | 8.0 | — | 7.0 | 7.0 | — | 55 |
| 25 kD (21.8 kD)endo (EG5) | 225 | 7.5 | 10.0 | — | 6.5 | 9.0 | — | 80 |
| 43 kD (39.6 kD*)endo (EG6) | 395 | 8.0 | 8.0 | — | 7.2 | 7.2 | — | — |
| 45 kD α,β-Gal/β-Gluc | | — | — | 6.8 | — | — | 5.7 | — |
| 48 kD CBH | | 5.2 | 7.5 | 8.0 | 5.0 | 6.8 | — | — |
| 55 kD CBHI | 526 | 8.0 | 9.0 | — | 7.4 | 8.5 | — | 70 |
| 65 kD PGU | | — | — | 8.0 | — | — | 7.3 | — |
| 90 kD protease | | — | — | 9.0 | — | — | 9.0 | — |
| 100 kD esterase | | — | — | 9.0 | — | — | 9.0 | — |

Notes:
*molecular weights by MALDI; all others by SDS PAGE
xyl = xylanase
endo = endoglucanase
gal = galactosidase
gluc = glucosidase
CBN = cellbiohydrolase
PGU = polygalacturonase Any of the promoters or regulatory regions of expression of enzymes disclosed in Table A, for example, can be suitably employed. The nucleic acid sequences of these promoters and regulatory regions can readily be obtained from a *Chrysosporium* strain. Methods by which promoter sequences can be determined are numerous and well known in the art. Promoter sequences are generally found immediately preceding the ATG start codon at the beginning of the relevant gene. For example, promoter sequences can be identified by deleting sequences upstream of the relevant gene, using recombinant DNA techniques, and examining the effects of these deletions on expression of the gene. Also, for example, promoter sequences can often be inferred by comparing the sequence of regions upstream of the relevant gene with concensus promoter sequences.

For example, the promoter sequences of C1 endoglucanases were identified in this manner (see PCT/NL99/00618) by cloning the corresponding genes. Preferred promoters according to the invention are the 55 kDa cellobiohydrolase (CBH1), glyceraldehyde-3-phosphate dehydrogenase A, and the 30 kDa xylanase (XY1F) promoters from *Chrysosporium*, as these enzymes are expressed at high level by their own promoters. The promoters of the carbohydrate-degrading enzymes of *Chrysosporium lucknowense* in particular, especially *C. lucknowense* GARG 27K, can advantageously be used for expressing libraries of proteins in other fungal host organisms.

Particular embodiments of nucleic acid sequences according to the invention are known for *Chrysosporium, Aspergillus* and *Trichoderma*. Promoters for *Chrysosporium* are described in PCT/NL99/00618. The prior art provides a number of expression regulating regions for use in *Aspergillus*, e.g. U.S. Pat. Nos. 4,935,349; 5,198,345; 5,252,726; 5,705,358; and 5,965,384; and PCT application WO 93/07277. Expression in *Trichoderma* is disclosed in U.S. Pat. No. 6,022,725. The contents of these patents are hereby incorporated by reference in their entirety.

The hydrophobin gene is a fungal gene that is highly expressed. It is thus suggested that the promoter sequence of a hydrophobin gene, preferably from *Chrysosporium*, may be suitably applied as expression regulating sequence in a suitable embodiment of the invention. *Trichoderma reesei* and *Trichoderma harzianum* gene sequences for hydrophobin have been disclosed for example in the prior art as well as a gene sequence for *Aspergillus fumigatus* and *Aspergillus nidulans* and the relevant sequence information is hereby incorporated by reference (Nakari-Setala et al., *Eur. J. Biochem.* 1996, 235:248-255; Parta et al., *Infect. Immun.* 1994 62:4389-4395; Munoz et al., *Curr. Genet.* 1997, 32:225-230; and Stringer et al., *Mol. Microbiol.* 1995 16:3344). Using this sequence information a person skilled in the art can obtain the expression regulating sequences of *Chrysosporium* hydrophobin genes without undue experimentation following standard techniques such as those suggested above. A recombinant *Chrysosporium* strain according to the invention can comprise a hydrophobin-regulating region operably linked to the sequence encoding the heterologous protein.

An expression regulating sequence can also additionally comprise an enhancer or silencer. These are also well known in the prior art and are usually located some distance away from the promoter. The expression regulating sequences can also comprise promoters with activator binding sites and repressor binding sites. In some cases such sites may also be modified to eliminate this type of regulation. For example, filamentous fungal promoters in which creA sites are present have been described. The creA sites can be mutated to ensure that the glucose repression normally resulting from the presence of creA is eliminated. Use of such a promoter enables production of the library of proteins encoded by the nucleic acid sequences regulated by the promoter in the presence of glucose. The method is exemplified in WO 94/13820 and WO 97/09438. These promoters can be used either with or without their creA sites. Mutants in which the creA sites have been mutated can be used as expression regulating sequences in a recombinant strain according to the invention and the library of nucleic acid sequences it regulates can then be expressed in the presence of glucose. Such *Chrysosporium* promoters ensure derepression in an analogous manner to that illustrated in WO 97/09438. The identity of creA sites is known from the prior art. Alternatively, it is possible to apply a promoter with CreA binding sites that have not been mutated in a host strain with a mutation elsewhere in the repression system e.g. in the creA gene itself, so that the strain can, notwithstanding the presence of creA binding sites, produce the library of proteins in the presence of glucose.

Terminator sequences are also expression-regulating sequences and these are operably linked to the 3' termini of the sequences to be expressed. A variety of known fungal terminators are likely to be functional in the host strains of the invention. Examples are the *A. nidulans* trpC terminator, *A. niger* alpha-glucosidase terminator, *A. niger* glucoamylase terminator, *Mucor miehei* carboxyl protease terminator (see U.S. Pat. No. 5,578,463), and the *Trichoderma reesei* cellobiohydrolase terminator. *Chrysosporium* terminator sequences, e.g. the EG6 terminator, will of course function well in *Chrysosporium*.

A suitable transformation vector for use according to the invention may optionally have the exogenous nucleic acid sequences to be expressed operably linked to a sequence encoding a signal sequence. A signal sequence is an amino acid sequence which, when operably linked to the amino acid sequence of an expressed protein, enables secretion of the protein from the host organism. Such a signal sequence may be one associated with a heterologous protein or it may be one native to the host. The nucleic acid sequence encoding the signal sequence must be positioned in frame to permit translation of the signal sequence and the heterologous proteins. Signal sequences will be particularly preferred where the invention is being used in conjunction with directed molecular evolution, and a single, secreted exogenous protein is being evolved.

It will be understood that it is less advanatageous to incorporate a signal sequence in a vector that is to be used to express a library, as this will decrease the probability of expressing the protein of interest. In a genomic library prepared by randomly shearing the DNA and cloning into a vector, the probability that one would obtain an in frame fusion of a gene in the library to the signal sequence is low. Also, even where an in-frame fusion has been obtained, the chosen signal sequence may not work with all genes. For these reasons it may be preferable not to employ a signal sequence when screening a genomic DNA library, but rather to screen for the activity or presence of intracelllular exogenous protein. Analysis of the activity or presence of intracellular proteins may be accomplished by pretreating the transformant library with enzymes that convert the fungal cells to protoplasts, followed by lysis. The procedure has been described by van Zeyl et al., *J. Biotechnol.* 59:221-224 (1997). This procedure has been applied to *Chrysosporium* to allow colony PCR from *Chrysosporium* transformants grown in microtiter plates.

Any signal sequence capable of permitting secretion of a protein from a *Chrysosporium* strain is envisaged. Such a signal sequence is preferably a fungal signal sequence, more preferably an Ascomycete signal sequence. Suitable signal sequences can be derived from eukaryotes generally, preferably from yeasts or from any of the following genera of fungi: *Aspergillus, Trichoderma, Chrysosporium, Pichia, Neurospora, Rhizomucor, Hansenula, Humicola, Mucor, Tolypocladium, Fusarium, Penicillium, Saccharomyces, Talaromyces* or alternative sexual forms thereof such as *Emericella* and *Hypocrea*. Signal sequences that are particularly useful are those natively associated with cellobiohydrolase, endoglucanase, beta-galactosidase, xylanase, pectinase, esterase, hydrophobin, protease or amylase. Examples include amylase or glucoamylase of *Aspergillus* or *Humicola*, TAKA amylase of *Aspergillus oryzae*, α-amylase of *Aspergillus niger*, carboxyl peptidase of *Mucor* (U.S. Pat. No. 5,578,463), a lipase or proteinase from *Rhizomucor miehei*, cellobiohydrolase of *Trichoderma*, beta-galactosidase of *Penicillium canescens* CBH1 from *Chrysosporium*, and the alpha mating factor of *Saccharomyces*.

Alternatively the signal sequence can be from an amylase or subtilisin gene of a strain of *Bacillus*. A signal sequence from the same genus as the host strain is extremely suitable as it is most likely to be specifically adapted to the specific host; thus when *Chrysosporium lucknowense* is the host, the signal sequence is preferably a signal sequence of *Chrysosporium*. *Chrysosporium* strains C1, UV13-6, NG7C-19 and UV18-25 secrete proteins in extremely large amounts, and signal sequences from these strains are of particular interest. Signal sequences from filamentous fungi and yeast may be useful, as well as signal sequences of non-fungal origin.

A transformed recombinant host fungus according to any of the embodiments of the invention can further comprise a selectable marker. Such a selectable marker permits selection of transformed or transfected cells. A selectable marker often encodes a gene product providing a specific type of resistance foreign to the non-transformed strain. This can be resistance to heavy metals, antibiotics or biocides in general. Prototrophy is also a useful selectable marker of the non-antibiotic variety. Auxotrophic markers generate nutritional deficiencies in the host cells, and genes correcting those deficiencies can be used for selection. Examples of commonly used resistance and auxotrophic selection markers are amdS (acetamidase), hph (hygromycin phosphotransferase), pyrG (orotidine-5'-phosphate decarboxylase), and pyrE (orotate P-ribosyl transferase, trpC (anthranilate synthase), argB (ornithine carbamoyltransferase), sC (sulphate adenyltransferase), bar (phosphinothricin acetyltransferase), niaD (nitrate reductase), Sh-ble (bleomycin-phleomycin resistance), mutant acetolactate synthase (sulfonylurea resistance), and neomycin phosphotransferase (aminoglycoside resistance). A preferred selection marker in *Chrysosporium* is orotate P-ribosyl transferase. Selection can be carried out by cotransformation where the selection marker is on a separate vector or where the selection marker is on the same nucleic acid fragment as the protein-encoding sequence for the heterologous protein.

A further improvement of the transformation frequency may be obtained by the use of the AMA1 replicator sequence, which is useful for example in *Aspergillus niger* (Verdoes et al., *Gene* 146:159-165 (1994)). This sequence results in a 10- to 100-fold increase in the transformation frequency in a number of different filamentous fungi. Furthermore, the introduced DNA is retained autonomously in the fungal cells, in a multiple-copy fashion, without integration into the fungal genome. This is expected to be beneficial for the high throughput screening method of the present invention, as the non-integrative state reduces variations in the level of gene expression between different transformants. Moreover, as the introduced DNA is not recombined into the host DNA, no unwanted mutations in the host genome will occur. Uniform levels of exogenous gene expression may be obtained by use of autonomously replicating vectors such as AMA1, or alternatively, autonomous replication in fungi can be promoted by telomeric sequences (see e.g. A. Aleksenko and L. Ivanova, *Mol. Gen. Genet.* 1998 260:159-164.)

As used herein the term "heterologous protein" is a protein or polypeptide not normally expressed or secreted by the host strain used for expression according to the invention. A heterologous protein may be of prokayotic origin, or it may be derived from a fungus, plant, insect, or higher animal such as a mammal. For pharmaceutical screening purposes quite often a preference will exist for human proteins, thus a preferred embodiment will be a host wherein the DNA library is of human origin. Such embodiments are therefore also considered suitable examples of the invention.

Expression of a library of human genes, derived from a genomic human DNA library, in the filamentous fungi of the invention is expected to be efficient for several reasons. It is now known that the average size of human genes is 3,000-5,000 bp, and that human introns average about 75 to about 150 bp (total range 40->50,000). Filamentous fungi have introns of 40-75 bp, but they can deal with introns up to 500 bp in length. On average, human genes carry 3-5 introns per gene (M. Deutsch, M. Long, *Nucl. Acids Res.* 1999 27:3219-3228; Table B). Human signal sequences are also known to function in filamentous fungi. For these reasons, it is likely that a large number of human genes can be expressed and secreted at high levels by the methods of this invention.

TABLE B

| Organism | Introns per gene | Average intron size (nt) (range) | Intron structure |
|---|---|---|---|
| Animal/ Plant | 3-5 | 75-150 (40->50000) 80% under 150 nt | GTnnGt ... CtxAC ... yAG |
| Fungi | 3 | 40-75 (40-500) | GTAnGy ... CtxAC ... yAG |
| Yeast | 0.01 | 50-60 (?-?) | GTATGT ... TACTAAC ... yAG |

The methods of the invention are thus expected to be useful for expression of DNA libraries derived from both prokaryotic and eukaryotic genomes. As described above, the methods are capable of expression and discovery of both secreted and intracellular proteins, giving ready access to an extemely large number of genes and proteins.

A further aspect of the invention includes the construction and screening of fungal mutant libraries, and fungal mutant libraries prepared by the methods disclosed herein. The libraries may be obtained by transformation of the fungal hosts according to this invention with any means of integrative or non-integrative transformation, using methods known to those skilled in the art. This library of fungi based on the preferred host strains may be handled and screened for desired properties or activities of exogenous proteins in miniaturized and/or high-throughput format screening methods. By property or activity of interest is meant any physical, physicochemical, chemical, biological, or catalytic property, or any improvement, increase, or decrease in such a property, associated with an exogenous protein of a library member. The library may also be screened for metabolites, or for a property or activity associated with a metabolite, produced as a result of the presence of exogenous and/or endogenous proteins. The library may also be screened for fungi producing increased or decreased quantities of such protein or metabolites.

In another aspect of this invention, the library of transformed fungi may be screened for the presence of fungal metabolites having desirable properties. Examples of such metabolites include polyketides, alkaloids, and terpenoid natural products. It is anticipated that multiple genes or gene clusters (operons) may be transferred to the host cells of the invention, and that non-protein products generated by the action of the encoded enzymes will then be generated in the host cells. For example, it has been shown that DNA encoding the proteins necessary for production of lovastatin can be transferred to *Aspergillus oryzae* (U.S. Pat. No. 5,362,638; see also U.S. Pat. No. 5,849,541).

In another embodiment of the invention, the library of transformed fungi may be screened for the presence of DNA that hybridizes to a nucleic acid probe of interest. In this embodiment, expression and/or secretion of exogenous proteins is not essential, although it will often still be desirable. Where protein expressing is not needed, it will be appreciated that regulatory sequences are not needed in the vector.

In yet another embodiment of the invention, the library of transformed fungi may be screened for some desirable property of the fungi themselves, such as for example tolerance to a physically or chemically extreme environment, or the ability to produce, modify, degrade or metabolize a substance of interest. Such desirable properties may or may not be ascribable to the presence of a single exogenous protein. This embodiment will be of particular utility when employed as part of a process of directed evolution.

The heterologous DNA may be genomic DNA or cDNA, prepared from biological specimens by methods well known in the art. The biological specimen may be an environmental sample (for example, soil, compost, forest litter, seawater, or fresh water), or an extracted, filtered, or centrifuged or otherwise concentrated sample therefrom. Mixed cultures of microorganisms derived from environmental samples may be employed as well. The biological sample may also be derived from any single species of organism, such as a cultured microorganism, or plant, insect, or other animal such as a mammal. In addition, the heterologous DNA may be synthetic or semi-synthetic, for example random DNA sequences or DNA comprising naturally-occurring segments which have been shuffled, mutated, or otherwise altered. An example of a semi-synthetic nucleic library is found in Wagner et al., WO 00/0632. DNA from environmental samples (or mixed cultures derived therefrom) will be advantageous for the discovery of novel proteins, while the use of DNA from a single species will be advantageous in that (1) an appropriate vector may be more judiciously chosen, and (2) the practitioner will be directed to related or similar species for further screening if a protein of interest is identified.

Compared to traditional fungal hosts, transformation, expression and secretion rates are exceedingly high when using a *Chrysosporium* strain exhibiting the compact mycelial morphology of strain UV 18-25. Thus a recombinant strain according to the invention will preferably exhibit such morphology. The invention however also covers non-recombinant strains or otherwise engineered strains of fungi exhibiting this characteristic. An attractive embodiment of the invention would employ a recombinant *Chrysosporium* strain exhibiting a viscosity below that of strain NG7C-19, preferably below that of UV18-25 under corresponding or identical culture conditions. We have determined that the viscosity of a culture of UV18-25 is below 10 cP as opposed to that of previously known *Trichoderma reesei* being of the order 200-

600 cP, and with that of traditional *Aspergillus niger* being of the order 1500-2000 cP under optimal culture conditions during the middle to late stages of fermentation. Accordingly the invention may employ any engineered or mutant filamentous fungus exhibiting this low-viscosity characteristic, such as the *Chrysosporium* UV 18-25 (VKM F-3631 D) strain, the *Trichoderma* X 252 strain, or *A. sojae* pclA (derived from ATCC 11906) or *A. niger* pclA.

The fluidity of filamentous fungal cultures can vary over a wide range, from nearly solid to a free-flowing liquid. Viscosity can readily be quantitated by Brookfield rotational viscometry, use of kinematic viscosity tubes, falling ball viscometer or cup type viscometer. Fermentation broths are non-Newtonian fluids, and the apparent viscosity will be dependent to some extent upon the shear rate (Goudar et al., *Appl. Microbiol. Biotechnol.* 1999 51:310-315). This effect is however much less pronounced for the low-viscosity cultures employed in the present invention.

The use of such low viscosity cultures in the screening of an expression library according to the method of the invention is highly advantageous. The screening of DNA libraries expressed in filamentous fungi has heretofore been limited to relatively slow and laborious methods. In general, once fungi have been transformed (and the transformants optionally selected for), it has been necessary to prepare spores or conidia, or to mechanically disrupt the mycelia, in order to disperse the library of transformed fungi into individual organisms or reproductive elements. This dispersal is necessary so that the separated organisms can be cultured into clonal colonies or cultures. The spores, conidia, or mycelial fragments are then diluted and "plated out" in standard culture dishes, and the individual colonies are inspected for color, alterations to the substrate, or other detectable indication of the presence of the protein activity or property being sought. In another approach, secreted proteins are blotted from the colonies onto a membrane, and the membrane is probed or examined for an indication of the presence of the protein activity or property of interest. Use of membranes has proved useful where proteolytic degradation of exogenous protein is a problem (Asgeirsdottir et al., *Appl. Environ. Microbiol.* 1999, 65:2250-2252). Such procedures are labor-intensive and have not proven amenable to automation, and as a result high-throughput screening of fungally-expressed proteins has not heretofore been accomplished with conventional filamentous fungi. For purposes of this disclosure, high-throughput screening refers to any partially- or fully-automated screening method that is capable of evaluating the proteins expressed by about 1,000 or more transformants per day, and particularly to those methods capable of evaluating 5,000 or more transformants per day, and most particularly to methods capable of evaluating 10,000 or more transformants per day.

The automated high-throughput screening of a library of transformed fungi according to the present invention, accordingly, may be carried out in a number of known ways. Methods that are known to be applicable to bacteria or yeast may in general be applied to the low-viscosity fungi of the present invention. This is made possible by the presence of transferable reproductive elements in combination with the low-viscosity phenotype, a consequence of the relatively non-entangled morphology of the hyphae of the mutant fungi employed. In essence, the mutant fungi, and/or their transferable reproductive elements, behave very much like individual bacteria or yeast during the mechanical manipulations involved in automated high-throughput screening. This is in contrast to wild-type fungi, and most industrially-adapted fungi as well, which produce highly entangled mycelia which do not permit the ready separation of the individual organisms from one another.

For example, a dilute suspension of transformed fungi according to the present invention may be aliquotted out through a mechanical micropipette into the wells of a 96-well microplate. It is anticipated that liquid-handling apparatus capable of pipetting into 384- or 1536-well microplates can also be adapted to the task of automated dispersal of the organisms into microplates. The concentration of the suspended organisms can be adjusted as desired to control the average number of organisms (or other transferable reproductive elements) per well. It will be appreciated that where multiple individual organisms are aliquotted into wells, the identification of the desired protein activity or property in that well will be followed by dilution of the contents of the well and culturing the organisms present into individual clonal colonies or cultures. In this manner the throughput of the system may be increased, at the cost of the need for subsequent resolution of the contents of each well that presents a "hit".

In an alternative embodiment, a cell sorter may be interposed in the fluid path, which is capable of directing the flow of the culture to the wells of the microplate upon the detection of an organism or other transferable reproductive element in the detector cell. This embodiment permits the reasonably accurate dispensation of one organism per well. The use of an optically-detectable marker, such as green fluorescent protein, to identify transformats is particularly useful in this embodiment, as it permits the automated selection of transformants by a fluorescence-activated cell sorter.

In yet another embodiment, colonies growing on solid media can be picked by a robotic colony picker, and the organisms transferred by the robot to the wells of a microtiter plate. Well-separated colonies will give rise to single clones in each well.

The dispersed organisms are then permitted to grow into clonal cultures in the microplate wells. Inducers, nutrients, etc. may be added as desired by the automated fluid dispensing system. The system may also be used to add any reagents required to enable the detection of the protein activity or property of interest. For example, colorogenic or fluorogenic substrates can be added so as to permit the spectroscopic or fluorometric detection of an enzyme activity. The low viscosity and submerged growth habit of the cultures in the wells of a microtiter plate permit the rapid diffusion of such reagents into the culture, greatly enhancing the sensitivity and reliability of the assay. Diffusion of oxygen and nutrients is also greatly enhanced, facilitating rapid growth and maximal expression and secretion of exogenous peptides. Certain assays, such as the scintillation proximity assay, rely on the diffusion of soluble components so as to arrive at an equilibrium state; again the low viscosity of the fungal cultures of the present invention makes this high throughput assay possible. Finally, in a highly automated system it will be desirable to automatically pick, aspirate, or pipette clonal cultures of interest from their wells in the microtiter plate, and the low viscosity and submerged growth habit of the cultures will make this possible. All of the above operations would be difficult or impossible given the viscosity of traditional filamenous fungal cultures, especially cultures growing as surface mats in the unstirred, shear-free conditions of a microtiter plate well.

In another embodiment, single cells are passed through a microfluidic apparatus, and the property or activity of interest is detected optically (Wada et al., WO 99/67639). Low viscosity is essential to the operation of a microfluidics device, and cultures of the low-viscosity mutant fungi of the present invention are expected to be amenable to microfluidic manipulation. Short et al., in U.S. Pat. No. 6,174,673, have described how fluorogenic substrates may be employed to detect an enzyme activity of interest, and how host cells expressing such an activity may be isolated with a fluorescence-activated cell sorter. The methods of the present invention are compatible with this method of identification of expressed proteins.

In one embodiment, where transformants carry a fluorescent protein as a marker, the fluorescence may be quantitated and employed as a measure of the amount of gene expression and/or expressed protein present in a given culture. In this embodiment, it is possible not only to detect an exogenous protein of interest, but to estimate the specific activity of the protein, as described by Blyna et al. in WO 00/78997. This embodiment will be particularly preferred where the screening method of the invention is employed as part of a process of directed evolution.

In those cases where a greater viscosity is acceptable, a gel-forming matrix may provide certain advantages when culturing fungi, and conducting biochemical assays, in a microplate format, as described by Bochner in U.S. Pat. No. 6,046,021.

Another class of high-thoughput screens is by photometric analysis, by digital imaging spectroscopy, of large numbers of individual colonies growing on a solid substrate. See for example Youvan et al., 1994, *Meth. Enzymol.* 246:732-748. In this method, changes in the overall absorption or emission spectra of specialized reagents are indicative of the presence of a heterologous protein activity or property of interest. The ready dispersal of individual organisms attendant upon the use of low-viscosity mutants also enables the use of filamentous fungi in this method. The tendency for colonies of the mutant fungi of the invention to exhibit less lateral growth, and to produce smooth, compact, and well-defined colonies on solid media, is also advantageous in such a screening system. Furthermore, the superior expression and secretion characteristics of fungi as compared to bacteria provide greater quantities of protein for spectral analysis.

An automated microorganism handling tool is described in Japanese patent application publication number 11-304666. This device is capable of the transfer of microdroplets containing individual cells, and it is anticipated that the fungal strains of the present invention, by virtue of their morphology, will be amenable to micromanipulation of individual clones with this device.

An automated microbiological high-throughput screening system is described in Beydon et al., *J. Biomol. Screening* 5:13-21 (2000). The robotic system is capable of transferring droplets with a volume of 400 nl to agar plates, and processing 10,000 screening points per hour, and has been used to conduct yeast two-hybrid screens. It is anticipated that the fungal hosts of the present invention will be as amenable as yeast to high-throughput screening with systems of this type.

As an alternative to microtiter plates, transformants can be grown on plates and, in the form of microcolonies, assayed optically as described in WO 00/78997.

The development of high throughput screens in general is discussed by Jayawickreme and Kost, *Curr. Opin. Biotechnol.* 8:629-634 (1997). A high throughput screen for rarely transcribed differentially expressed genes is described in von Stein et al., *Nucleic Acids Res.* 35: 2598-2602 (1997).

The *Chrysosporium* strain UV18-25 and the *Trichoderma* strain X 252 illustrate various aspects of the invention exceedingly well. The invention however may employ other mutant or otherwise engineered strains of filamentous fungi that produce transferable reproductive elements in suspension and exhibit low viscocity in culture. The specific morphology of the fungi may not be critical; the present inventors have observed short, non-entangled mycelia in these two strains but other morphologies, such as close and extensive hyphal branching, may also lead to reduced viscosity. Fungal strains according to the invention are preferred if they exhibit optimal growth conditions at neutral pH and temperatures of 25-43° C. Such screening conditions are advantageous for maintaining the activity of exogenous proteins, in particular those susceptible to degradation or inactivation at acidic pH. Most mammalian proteins, and human proteins in particular, have evolved to function at physiological pH and temperature, and screening for the normal activity of a human enzyme is best carried out under those conditions. Proteins intended for therapeutic use will have to function under such conditions, which also makes these the preferred screening conditions. *Chrysosporium* strains exhibit precisely this characteristic, growing well at neutral pH and 35-40° C., while other commonly employed fungal host species (e.g. *Aspergillus* and *Trichoderma*) grow best at acidic pH and may be less suitable for this reason.

Another application of the method of the present invention is in the process of "directed evolution," wherein novel protein-encoding DNA sequences are generated, the encoded proteins are expressed in a host cell, and those seqences encoding proteins exhibiting a desired characteristic are selected, mutated, and expressed again. The process is repeated for a number of cycles until a protein with the desired characteristics is obtained. Gene shuffling, protein engineering, error-prone PCR, site-directed mutagenesis, and combinatorial and random mutagenesis are examples of processes through which novel DNA sequences encoding exogenous proteins can be generated. U.S. Pat. Nos. 5,223,409, 5,780,279 and 5,770,356 provide teaching of directed evolution. See also Kuchner and Arnold, *Trends in Biotechnology*, 15:523-530 (1997); Schmidt-Dannert and Arnold, *Trends in Biotech.*, 17:135-136 (1999); Arnold and Volkov, *Curr. Opin. Chem. Biol.*, 3:54-59 (1999); Zhao et al., *Manual of Industrial Microbiology and Biotechnology*, $2^{nd}$ Ed., (Demain and Davies, eds.) pp. 597-604, ASM Press, Washington D.C., 1999; Arnold and Wintrode, *Encyclopedia of Bioprocess Technology: Fermentation, Biocatalysis, and Bioseparation*, (Flickinger and Drew, eds.) pp. 971-987, John Wiley & Sons, New York, 1999; and Minshull and Stemmer, *Curr. Opin. Chem. Biol.* 3:284-290.

An application of combinatorial mutagenesis is disclosed in Hu et al., *Biochemistry.* 1998 37:10006-10015. U.S. Pat. No. 5,763,192 describes a process for obtaining novel protein-encoding DNA sequences by stochastically generating synthetic sequences, introducing them into a host, and selecting host cells with the desired characteristic. Methods for effecting artificial gene recombination (DNA shuffling) include random priming recombination (Z. Shao, et al., *Nucleic Acids Res.*, 26:681-683 (1998)), the staggered extension process (H. Zhao et al., *Nature Biotech.*, 16:258-262 (1998)), and heteroduplex recombination (A. Volkov et al., *Nucleic Acids Res.*, 27:e18 (1999)). Error-prone PCR is yet another approach (Song and Rhee, *Appl. Environ. Microbiol.* 66:890-894 (2000)).

There are two widely-practiced methods of carrying out the selection step in a directed evolution process. In one method, the protein activity of interest is somehow made essential to the survival of the host cells. For example, if the activity desired is a cellulase active at pH 8, a cellulase gene could be mutated and introduced into the host cells. The transformants are grown with cellulose as the sole carbon source, and the pH raised gradually until only a few survivors remain. The mutated cellulase gene from the survivors, which presumably encodes a cellulase active at relatively high pH, is subjected to another round of mutation, and the process is repeated until transformants that can grow well on cellulose at pH 8 are obtained. Thermostable variants of enzymes can likewise be evolved, by cycles of gene mutation and high-temperature culturing of host cells (Liao et al., *Proc. Natl. Acad. Sci. USA* 1986 83:576-580; Giveret al., *Proc. Natl. Acad. Sci. USA*. 1998 95:12809-12813. For purposes of this application, mutation of DNA sequences encoding exogenous proteins may be accomplished by any of several methods employed for directed evolution, for example by gene shuffling, in vivo recombination, or cassette mutagenesis.

The chief advantage of this method is the massively parallel nature of the "survival of the fittest" selection step. Millions, or billions, of unsuccessful mutations are simultaneously eliminated from consideration without the need to evaluate them individually. However, it is not always possible to link an enzyme activity of interest to the survival of the host. For example where the desired protein property is selective binding to a target of interest, making the binding property essential to survival is likely to be difficult. Also, survival under forced conditions such as high temperature or extreme pH is likely to be dependent upon multiple factors, and a desirable mutation will not be selected for and will be lost if the host cell is unable to survive for reasons unrelated to the properties of the mutant protein.

An alternative to the massively parallel "survival of the fittest" approach is serial screening. In this approach, individual transformants are screened by traditional methods, such as observation of cleared or colored zones around colonies growing on indicator media, calorimetric or fluorometric enzyme assays, immunoassays, binding assays, etc. See for example Joo et al., *Nature* 399:670-673 (1999), where a cytochrome P450 monooxygenase not requiring NADH as a cofactor was evolved by cycles of mutation and screening; May et al., *Nature Biotech.* 18:317-320 (2000), where a hydantoinase of reversed stereoselectivity was evolved in a similar fashion; and Miyazaki et al., *J. Mol. Biol.* 297:1015-1026 (2000), where a thermostable subtilisin was evolved.

The screening approach has clear advantages over a simple "survival screen," especially if it can be carried out in a high-throughput manner that approaches the throughput of the massively parallel "survival screen" technique. For example, a degree of parallelism has been introduced by employing such measures as digital imaging of the transformed organisms (Joo et al., *Chemistry & Biology*, 6:699-706 (1999)) or digital spectroscopic evaluation of colonies (Youvan et al., 1994, *Meth. Enzymol.* 246:732-748). Serial assays can be automated by the use of cell sorting (Fu et al., *Nature Biotech.*, 17:1109-1111 (1999)). A well-established approach to high-throughput screening involves the automated evaluation of expressed proteins in microtiter plates, using commercially available plate readers, and the method of the present invention is well-suited to the application of this mode of high-throughput screening to directed evolution.

In this embodiment of the invention, a gene encoding a protein of interest is mutated by any known method of generating a plurality of mutants, the mutant protein-encoding DNA is introduced by means of a suitable expression vector into a low-viscosity filamentous fungal host according to the present invention, and the transformants are optionally selected for and cultured. The host cells are then dispersed as described previously into the wells of a microtiter plate, or otherwise spatially separated into resolvable locations, so as to provide individual monoclonal cultures (or poly-clonal cultures having fewer than about 100 different clones). The cells are preferably dispersed into the wells of a micro-titer plate. The protein encoded by the mutant DNA is preferably secreted into the medium in the wells of the microtiter plates. Each of the dispersed cultures is screened for the protein activity of interest, and those most strongly exhibiting the desired property are selected. The gene encoding the protein of interest in the selected cultures is mutated again, the mutant DNA is again introduced into the low-viscosity fungal host, and the transformants are re-screened. The mutating and re-screening process is repeated until the value of the property of interest reaches a desired level.

In an alternative embodiment, directed evolution is carried out by mutation and reproduction of the gene of interest in another organism, such as *E. coli*, followed by transfer of the mutant genes to a filamentous fungus according to the present invention for screening.

It will be readily appreciated by those skilled in the art that a protein that appears to be of interest based upon the screening assay will not necessarily have all the other properties required for commercial utility. For example, the possession of enzymatic activity, however high the specific activity, will not indicate that the mutant enzyme has the requisite thermal or pH stability, or detergent or protease resistance, or non-immunogenicity, or other property that might be desirable or necessary in a commercially viable product. There is a need for methods of readily determining whether an identified protein has commercially useful properties.

The prior art approaches to screening have not provided a solution to this need, because the host organisms (bacteria and yeast) were not adapted to the production of isolable quantities of protein. It has heretofore been necessary to transfer potentially useful genes from one organism to another, as one proceeded through DNA library preparation, gene expression, screening, expression of research quantities of gene products, and over-expression in industrially suitable production strains. The mutant filamentous fungi of the present invention, on the other hand, are excellent overproducers and secretors of exogenous proteins, especially when employed with the vectors disclosed herein. Sufficient protein may be isolated not only for purposes of characterization, but for evaluation in application trials. Indeed, the strains used in the screening method of the invention are suitable for industrial production as well, since they possess desirable production properties such as low viscosity, high expression rates, and very high protein/biomass ratios.

Accordingly, in a preferred embodiment of the present invention, the method further comprises culturing a clonal colony or culture identified according to the method of the invention, under conditions permitting expression and secretion of the exogenous library protein (or a precursor thereof), and recovering the subsequently produced protein to obtain the protein of interest. Expression and secretion of a library protein may be facilitated by creating an in-frame fusion of the cloned gene with the gene for a heterologous protein (or a fragment thereof) with its corresponding signal sequence, or with the signal sequence from a third protein, all operably linked to an expression regulating sequence. By this approach a fusion protein is created that contains heterologous amino acid sequences upstream of the library protein. Subsequently, this fusion precursor protein may be isolated and recovered using purifacation techniques known in the art. The method may optionally comprise subjecting the secreted fusion protein precursor to a cleavage step to generate the library protein of interest. The cleavage step can be carried out with Kex-2, a Kex-2 like protease, or another selective protease, when the vector is engineered so that a protease cleavage site links a well-secreted protein carrier and the protein of interest.

The ready availability of mutant protein, directly from the screening host organism, has not previously been possible with prior art screening hosts. The present invention thus provides an advantage, in that the mutant proteins deemed of interest based upon the high-throughput screen can be isolated in sufficient quantities (milligrams) for further characterization and even larger quantities (grams to kilograms) for application trials. This particular embodiment of the invention thus permits the practitioner to select mutant proteins for the next round of directed evolution based upon any number of desirable properties, and not merely upon the one property detected in the high-throughput screen. The more stringent selection criteria made possible by the present invention should lead to a more efficient and cost-effective directed evolution process.

The method of production of a recombinant mutant filamentous fungal strain according to the invention comprises introducing a library of DNA sequences comprising nucleic acid sequences encoding heterologous proteins into a low-viscosity mutant filamentous fungus according to the invention, the nucleic acid sequences being operably linked to an expression regulating region. The introduction of the DNA sequences may be carried out in any manner known per se for transforming filamentous fungi. Those skilled in the art will appreciate that there are several well-established methods, such as $CaCl_2$-polyethylene glycol stimulated DNA uptake by fungal protoplasts (Johnstone et al., *EMBO J.*, 1985, 4:1307-1311). A protoplast transformation method is described in the examples. Alternative protoplast or spheroplast transformation methods are known and can be used as have been described in the prior art for other filamentous fungi. Vectors suitable for multicopy integration of heterologous DNA into the fungal genome are well-known; see for example Giuseppin et al., WO 91/00920. The use of autonomously replicating plasmids has long been known as an efficient transformation tool for fungi (Gems et al., *Gene* 1991 98:61-67; Verdoes et al., *Gene* 1994 146:159-165; Aleksenko and Clutterbuck, *Fungal Genetics Biol.* 1997 21:373-387; Aleksenko et al., *Mol. Gen. Genet.* 1996 253:242-246). Details of such methods can be found in many of the cited references, and they are thus incorporated by reference.

Exemplary methods according to the invention, comprising using a low-viscosity mutant strain of *Chrysosporium* or *A. sojae* as starting material for introduction of vectors carrying heterologous DNA, are presented below.

EXAMPLES

A. Development of Compact Growth Morphology Mutants

Various patent applications teach that morphological mutants can be isolated by various ways of screening. WO 96/02653 and WO 97/26330 describe non-defined mutants exhibiting compact morphology. It was found that a proprotein processing mutant of *A. sojae* had an unexpected aberrant growth phenotype (hyper-branching) while no detrimental effect on protein production were observed. Culture experiments with this strain revealed a very compact growth phenotype with micropellets. The observed characteristics were not only present in *A. sojae* but other mutated fungi as well, e.g. *A. niger*.

(1) Construction of an *A. niger* Proprotein Processing Mutant

To clone the proprotein convertase encoding gene from *A. niger*, PCR was used. Based on the comparison of various proprotein convertase genes from various yeast species and higher eukaryotes, different PCR primers were designed which are degenerated, respectively, 4, 2, 2, 512, 1152, 4608, 2048 and 49152 times. From the amplification using primers PE4 and PE6, two individual clones were obtained of which the encoded protein sequence did show significant homology to the *S. cerevisiae* KEX2 sequence. These clones were used for further experiments.

Based on the observed homology to other proprotein convertase genes of the cloned PCR fragment, the corresponding *A. niger* gene was designated pclA (from proprotein-convertase-like). Southern analysis of genomic digests of *A. niger* revealed that the pclA gene was a single copy gene with no closely related genes in the *A. niger* genome, as even at heterologous hybridisation conditions (50° C.; washes at 6×SSC) no additional hybridisation signals were evident. A first screening of an EMBL3 genomic library of *A. niger* N401 (van Hartingsveldt et al, *Mol. Gen. Genet.* 1987 206: 71-75) did not result in any positively hybridising plaques although about 10-20 genome equivalents were screened. In a second screening a full length genomic copy of the pclA gene was isolated from an *A. niger* N400 genomic library in EMBL4 (Goosen et al., *Curr. Genet.* 11:499-503 (1987)).

Of the 8 hybridising plaques which were obtained after screening 5-10 genome equivalents, 6 were still positive after a first rescreening. All these 6 clones most likely carried a full copy of the pclA gene, as in all clones (as was observed for the genomic DNA) with the PCR fragment two hybridising EcoRV fragments of 3 and 4 kb were present (the PCR fragment contained an EcoRV restriction site). Based on comparison of the size of other proprotein convertases, together these fragments will contain the complete pclA gene with 5' and 3' flanking sequences. The two EcoRV fragments and an overlapping 5 kb EcoRI fragment were subcloned for further characterisation.

Based on the restriction map the complete DNA sequence of the pclA gene was determined from the EcoRI and EcoRV subclones. Analysis of the obtained sequence revealed an open reading frame with considerable similarity to that of the *S. cerevisiae* KEX2 gene and other proprotein convertases. Based on further comparison two putative intron sequences were identified in the coding region. Subsequent PCR analysis with primers flanking the putative introns, on a pEMBLyex based *A. niger* cDNA library revealed that only the most 5' of these two sequences represented an actual intron. The general structure of the encoded PclA protein was clearly similar to that of other proprotein convertases. The overall similarity of the PclA protein with the other proprotein convertases was about 50%.

To demonstrate that the cloned pclA gene is a functional gene encoding a functional protein, the construction of strains devoid of the pclA gene was attempted. Therefore, pPCL1A, a pclA deletion vector, in which a large part of the pclA coding region was replaced for the *A. oryzae* pyrG selection marker, was generated. Subsequently, from this vector the 5 kb EcoRI insert fragment was used for transformation of various *A. niger* strains.

Figure 13B:
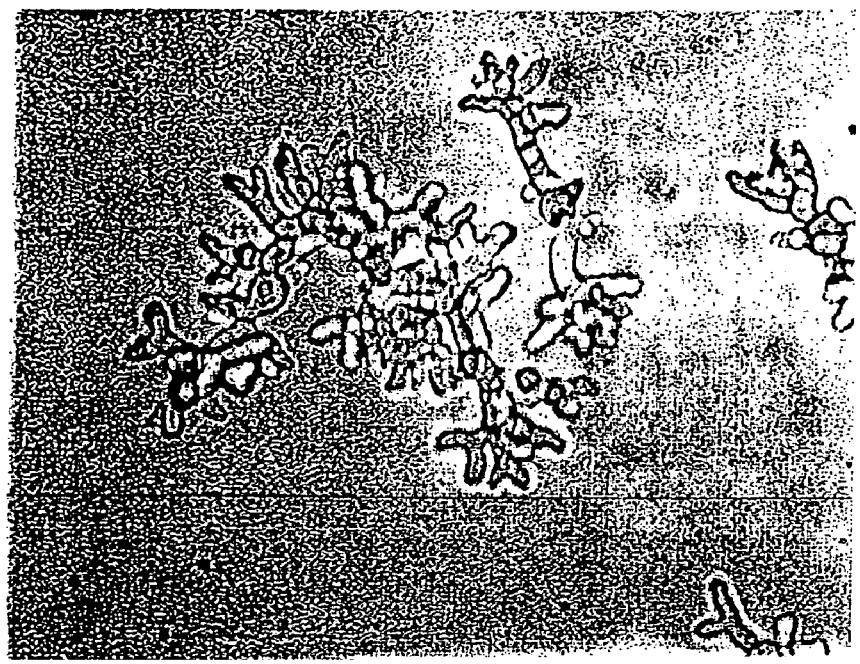
FIG. 13B is a photomicrobraph of an *Aspergillus niger* pclA mutant.
Figure 13A:
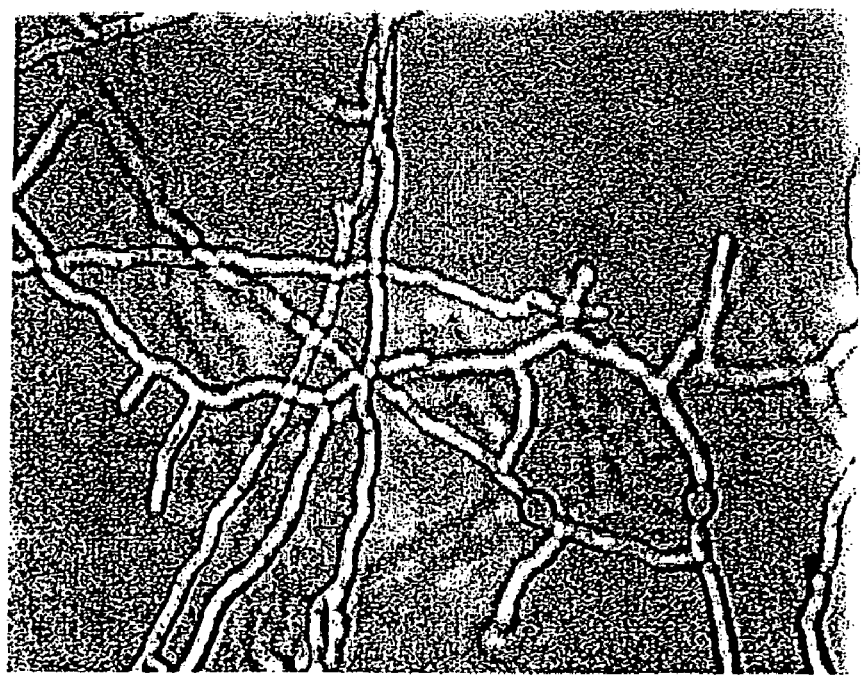
FIG. 13A is a photomicrograph of wildtype *Aspergillus niger*.

From these transformations (based on pyrG selection) numerous transformants were obtained. Interestingly, a fraction of the transformants (varying from 1-50%) displayed a very distinct aberrant phenotype (FIG. 13). Southern analysis of several wildtype and aberrant transformants revealed that these aberrant transformants which displayed a severely restricted (compact) growth phenotype, had lost the pclA gene. All strains displaying wild-type growth were shown to carry a copy of the replacement fragment integrated adjacent to the wild-type pclA gene or at a non-homologous position.

(2) Construction of an *A. sojae* Proprotein Processing Mutant

To construct the corresponding mutant in *A. sojae*, functional complementation of the low-viscosity mutant of *A. niger* was carried out by transformation of an *A. niger* pclA mutant with the *A. sojae* ATCC 11906 cosmid library. From the resulting complemented *A. niger* transformants, genomic cosmid clones were isolated, which comprised the *A. sojae* protein processing protease pclA. Partial sequence analysis of the isolated sequences confirmed the cloning of the *A. sojae* pclA gene. Based on the cloned *A. sojae* pclA sequences a gene replacement vector was generated following an approach similar to that described elsewhere in our examples, using the reusable pyrG selection marker described in WO 01/09352.

Figure 14B:
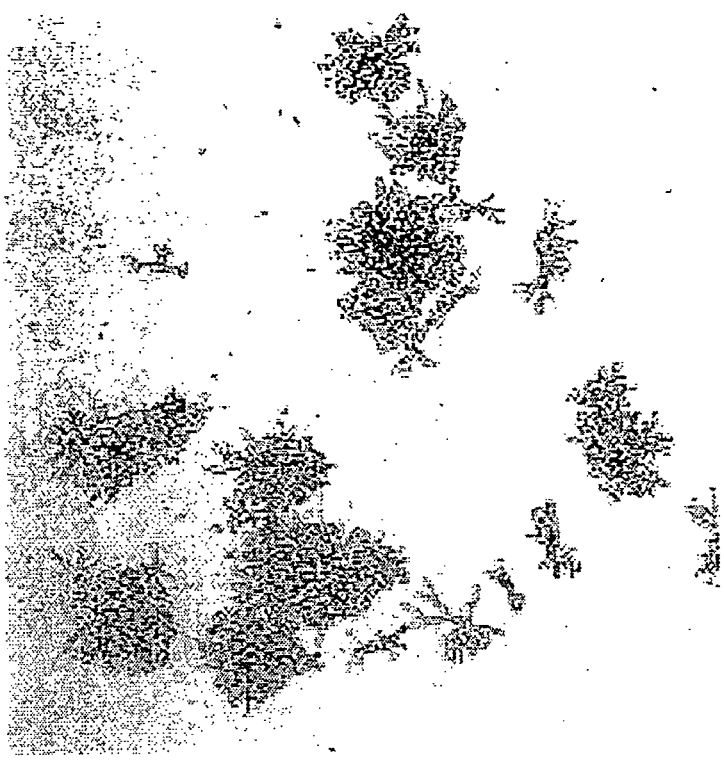
FIG. 14B is a photomicrobraph of an *Aspergillus sojae* pclA mutant.
Figure 14A:
FIG. 14A is a photomicrograph of wildtype *Aspergillus sojae*.

In addition, a gene disruption vector was constructed carrying the pyrG selection marker and 5' and 3' truncated fragment from the *A. sojae* pclA gene. Both the gene replacement and gene disruption vector were used to generate pclA mutants in ATCC 11906 and ATCC 11906 derivatives. Culture experiments with some of the resulting transformants revealed improved morphological characteristics, in particular compact growth morphology and micropellets. (FIGS. 14A and 14B)

(3) Isolation of Alternative *A. sojae* Compact Growth Mutants

Transformation of *A. sojae* ATCC 11906 and derivatives may be carried out with linear DNA fragments carrying a fungal selection marker. If no specific replicating sequences are provided transformants obtained using this procedure carry the introduced DNA integrated into the genome of the host strain. As the introduced selection marker is from heterologous origin (*A. niger*) only heterologous recombination will occur, leading to a collection of transformants carrying the marker DNA at various positions in the genome. This integration is prone to result in disruption of endogenous *A. sojae* sequences, thus resulting in a collection of *A. sojae* mutant strains. This is exemplified by the analysis of a large collection of transformants obtained from *A. sojae* ATCC 11906alpApyrG using a DNA fragment with the *A. niger* pyrG selection marker. In total several thousand transformants were analysed and from these 5-10 showed a morphologically aberrant phenotype. Among these several had a phenotype comparable to the pclA mutants. Similar as described for the cloning of the *A. sojae* pclA gene, the gene corresponding to the mutation could be isolated from the *A. sojae* gene library by complementation of the morphological phenotype. Based on the cloned gene the corresponding gene disruption/deletion mutants can be generated.

(4) Isolation of *Chrysosporium* Compact Growth Mutants.

Using a similar PCR based cloning approach as described for the *A. niger* pclA gene a fragment of the *Chrysosporium* proprotein processing gene, termed pcl1, was cloned from a *Chrysosporium* BLUESTAR™ gene library. A gene fragment carrying the complete genomic gene copy was subcloned from the pBLUESTAR clone. Based on the obtained subclone a gene disruption vector was generated as described for *A. sojae*. Instead of the pyrG marker, for *Chrysosporium* the repeat flanked version of the *A. niger* pyrE gene was used. Gene disruption-transformation of *Chrysosporium* resulted in strains with a compact growth phenotype.

B. Viscosity Determinations

The following operating parameter data ranges have been determined for fungal fermentations using five different fungal organisms. The five fungal organisms compared were strains of *Aspergillus niger*, *Trichoderma longibrachiatum* 18.2KK (formerly *Treesei*), *Trichoderma longibrachiatum* X 252, *Chrysosporium lucknowense* strain UV18-25, and *Aspergillus sojae* pclA. Viscosity of a fungal culture varies during the course of a fermentation, and varies with nutrient concentration. For the measurements reported here, medium containing between 20 and 100 g/l of a carbohydrate carbon source (e.g., lactose, sucrose, xylose, glucose, and the like) is inoculated with fungus, and the culture allowed to proceed through a "growth phase" during which the carbon source is consumed. Shake flask cultures are shaken at 200 rpm, while one-liter fermentation vessels are stirred with an impeller at 500-1000 rpm. Maximal viscosity typically occurs at or close to the end of the growth phase. At this time the culture is switched to a fed batch mode, wherein a carbon source is fed to the culture at a rate such that the concentration of the carbon source does not rise above about 0.5 g/l. A feed rate of between 1 and 3 g/l/hr is typical.

Viscosity was determined on a Brookfield LVF viscometer using the small sample adapter and spindle number 31, operated at 30° C. A fresh sample of fermentation broth (10 ml) was placed in the small sample spindle. The spindle speed was adjusted to give a reading in the range 10-80. After four minutes a reading was taken from the viscometer scale. The reading was multiplied by the factor given below to get the viscosity in centipoise (cP).

| Spindle Speed | Multiplication Factor |
| --- | --- |
| 6 | 50 |
| 12 | 25 |
| 30 | 10 |
| 60 | 5 |

The final viscosity was measured at fermentation end:

| Strain | Final viscosity, cP (mean ± s.d.) |
| --- | --- |
| *T. longibrachiatum* 18.2KK | (297 ± 173) |
| *A. niger* | 1,500-2,000 |
| *T. longibrachiatum* X-252 | ≦60 |
| *C. lucknowense* UV18-25 | ≦10 |
| *A. sojae* pclA | n.d. |

C Transformation of *Chrysosporium*, *Trichoderma* and *Tolypocladium*

Transformation media used were as follows:

Mandels Base:

| | |
| --- | --- |
| KH$_2$PO$_4$ | 2.0 g/l |
| (NH$_4$)$_2$SO$_4$ | 1.4 g/l |
| MgSO$_4$.7H$_2$O | 0.3 g/l |
| CaCl$_2$ | 0.3 g/l |
| Oligoelements | 1.0 ml/l |

MnR

| | |
| --- | --- |
| MnP + sucrose | 130 g/l |
| Yeast extract | 2.5 g/l |
| Glucose | 2.5 g/l |
| Agar | 15 g/l |
| MnR Soft: | MnR with only 7.5 g/l of agar. |

MPC:

| | | |
| --- | --- | --- |
| CaCl$_2$ | 50 mM | pH 5.8 |
| MOPS | 10 mM | |
| PEG | 40% | |

-continued

MnP Medium:

| | |
|---|---|
| Mandels Base with Peptone | 1 g/l |
| MES | 2 g/l |
| Sucrose | 100 g/l |
| Adjust pH to 5 | |

MnP $Ca^{2+}$:

MnP Medium +
$CaCl_2 2H_2O$, 50 mM
Adjust pH to 6.5

Media for Selection and Culture:

GS:

| | |
|---|---|
| Glucose | 10 g/l |
| Biosoyase | 5 g/l [Merieux] |

Mandels Base:

| | |
|---|---|
| Agar | 15 g/l pH should be 6.8 |

PDA:

| | |
|---|---|
| Potato Dextrose Agar (Difco) | 39 g/l pH should be 5.5 |

MPG:

| | |
|---|---|
| Mandels Base with K Phtalate | 5 g/l |
| Glucose | 30 g/l |
| Yeast extract | 5 g/l |

IC1

| | |
|---|---|
| 0.5 g/L | $K_2HPO_4$ pH 7.0 |
| 0.15 g/L | $MgSO_4 7H_2O$ |
| 0.05 g/L | KCl |
| 0.007 g/L | $FeSO_4.7H_2O$ |
| 1 g/L | Yeast extract (ohly KAT) |
| 10 g/L | Peptone or Pharmamedia |
| 10 g/L | lactose |
| 10 g/L | glucose |

The regeneration media (MnR) supplemented with 50 µg/ml phleomycin or 100-150 µg/ml hygromycin is used to select transformants. GS medium, supplemented with 5 µg/ml phleomycin is used to confirm antibiotic resistance.

PDA is a complete medium for fast growth and good sporulation. Liquid media are inoculated with 1/20th of spore suspension (all spores from one 90 mm PDA plate in 5 ml 0.1% Tween). Such cultures are grown at 27° C. in shake flasks (200 rpm).

Two untransformed *Chrysosporium* C1 strains and one *Trichoderma reesei* reference strain were tested on two media (GS pH 6.8, and Pridham agar, PA, pH 6.8). To test the antibiotic resistance level spores were collected from 7 day old PDA plates. Selective plates were incubated at 32° C. and scored after 2, 4 and 5 days. The C-1 strains NG7C-19 and UV 8-25 clearly had a low basal resistance level both to phleomycin and hygromycin, comparable to that for a reference *T. reesei* laboratory strain. This is a clear indication these standard fungal selectable markers can be used in *Chrysosporium* strains. Problems with other standard fungal selectable markers are not expected.

Selection of Sh-ble (phleomycin-resistance) transformed *Chrysosporium* strains was successfully carried out at 50 µg/ml. This was also the selection level used for *T. reesei* thus showing that differential selection can be easily achieved in *Chrysosporium*. The same comments are valid for strains transformed for hygromycin resistance at a level of 150 µg/ml.

The protoplast transformation technique was used on *Chrysosporium* based on the most generally applied fungal transformation technology. All spores from one 90 mm PDA plate were recovered in 8 ml IC1 and transferred into a shake flask of 50 ml IC1 medium for incubation for 15 hours at 35° C. and 200 rpm. After this the culture was centrifuged, the pellet was washed in MnP, brought back into solution in 10 ml MnP and 10 mg/ml Caylase $C_3$ and incubated for 30 minutes at 35° C. with agitation (150 rpm).

The solution was filtered and the filtrate was subjected to centrifugation for 10 minutes at 3500 rpm. The pellet was washed with 10 ml MnP $Ca^{2+}$. This was centrifuged for 10 minutes at 25° C. Then 50 microliters of cold MPC was added. The mixture was kept on ice for 30 minutes whereupon 2.5 ml PMC was added. After 15 minutes at room temperature 500 microliters of the treated protoplasts were mixed to 3 ml of MnR Soft and immediately plated out on a MnR plate containing phleomycin or hygromycin as selection agent. After incubation for five days at 30° C. transformants were analysed (clones become visible after 48 hours). Transformation efficiency was determined using 10 µg of reference plasmid pAN8-1. The results are presented in the following Table C.

TABLE C

Transformation efficiency
(using 10 µg of reference plasmid pAN8-1)

| | T. reesei | NG7C-19 | UV18-25 |
|---|---|---|---|
| Viability | $10^6$/200 µl | $5 \times 10^6$/200 µl | $5 \times 10^6$/200 µl |
| Transformants Per 200 µl | 2500 | $10^4$ | $10^4$ |
| Transformants per $10^6$ viable cells | 2500 | 2000 | 2000 |

The results show that the *Chrysosporium* transformant viability is superior to that of *Trichoderma*. The transformability of the strains is comparable and thus the number of transformants obtained in one experiment lies 4 times higher for *Chrysosporium* than for *T. reesei*. Thus the *Chrysosporium* transformation system not only equals the commonly used *T. reesei* system, but even outperforms it. This improvement can prove especially useful for vectors that are less transformation efficient than pAN8-1.

A number of other transformation and expression plasmids were constructed with homologous *Chrysosporium* protein encoding sequences and also with heterologous protein encoding sequences for use in transformation experiments with *Chrysosporium*. The vector maps are provided in FIGS. 6-11.

The homologous protein to be expressed was selected from the group of cellulases produced by *Chrysosporium* and consisted of endoglucanase 6 which belongs to family 6 (MW 43 kDa) and the heterologous protein was endoglucanase 3 which belongs to family 12 (MW 25 kDa) of *Penicillium*.

pF6g comprises *Chrysosporium* endoglucanase 6 promoter fragment linked to endoglucanase 6 signal sequence in frame with the endoglucanase 6 open reading frame followed by the endoglucanase 6 terminator sequence. Transformant selection is carried out by using cotransformation with a selectable vector.

pUT1150 comprises *Trichoderma reesei* cellobiohydrolase promoter linked to endoglucanase 6 signal sequence in frame with the endoglucanase 6 open reading frame followed by the *T. reesei* cellobiohydrolase terminator sequence. In addition this vector carries a second expression cassette with a selection marker, i.e. the phleomycin resistance gene (Sh-ble gene).

pUT1152 comprises *Aspergillus nidulans* glyceraldehyde-3-phosphate dehydrogenase A promoter linked to endoglucanase 6 signal sequence in frame with the endoglucanase 6 open reading frame followed by the *A. nidulans* anthranilate synthase (trpC) terminator sequence. In addition this vector carries a second expression cassette with a selection marker, i.e. the phleomycin resistance gene (Sh-ble gene).

pUT1155 comprises *A. nidulans* glyceraldehyde-3-phosphate dehydrogenase A promoter linked to *Trichoderma reesei* cellobiohydrolase signal sequence in frame with the carrier protein Sh-ble which in turn is linked in frame to the endoglucanase 6 open reading frame followed by the *A. nidulans* trpC terminator sequence. This vector uses the technology of the carrier protein fused to the protein of interest which is known to very much improve the secretion of the protein of interest.

pUT1160 comprises *Aspergillus nidulans* glyceraldehyde-3-phosphate dehydrogenase A promoter linked to *Trichoderma reesei* cellobiohydrolase signal sequence in frame with the carrier protein Sh-ble which in turn is linked in frame to the endoglucanase 3 open reading frame of *Penicillium* followed by the *A. nidulans* trpC terminator sequence.

pUT1162 comprises *Trichoderma reesei* cellobiohydrolase promoter linked to endoglucanase 3 signal sequence in frame with the endoglucanase 3 open reading frame of *Penicillium* followed by the *T. reesei* cellobiohydrolase terminator sequence. In addition this vector carries a second expression cassette with the phleomycin resistance gene (Sh-ble gene) as a selection marker.

It will be apparent to those skilled in the art that a sample of genomic or cDNA can be readily sheared or digested into protein-encoding fragments, and the fragments ligated into vectors such as those illustrated herein so as to produce a library of expression vectors. It will be further apparent that methods employing co-transfection are applicable, and that autonomously replicating vectors or integrating vectors may be employed to transfect filamentous fungi with such a library of vectors.

TABLE D

Comparative transformations

| Vector | Strain | Transformation | No of transf. |
|---|---|---|---|
| pUT1150 | UV18-25 | selection on phleomycin | 285 |
|  | T. geodes | selection on phleomycin | 144 |
| pUT1152 | UV18-25 | cotransformation pAN8.1 | 398 |
|  | T. geodes | cotransformation pAN8.1 | 45 |
| pF6g | UV18-25 | cotransformation pAN8.1 | 252 |
|  | T. geodes | cotransformation pAN8.1 | 127 |
| pUT1162 | UV18-25 | selection on phleomycin | >400 |
|  | T. geodes | (n.d.) |  |

Table D shows the results of transformation of both *Chrysoporium* UV18-25 and *Tolypocladium geodes*. The transformation protocol used is described below in the section for heterologous transformation.

D. Heterologous and Homologous Expression in *Chrysosporium* Formants

C1 strains (NG7C-19 and/or UV18-25) were tested for their ability to secrete various heterologous proteins: a bacterial protein (*Streptoalloteichus hindustanus* phleomycin-resistance protein, Sh-ble), a fungal protein (*Trichoderma reesei* xylanase II, XYN2) and a human protein (the human lysozyme, HLZ). The details of the process are as follows:

(1) C1 Secretion of *Streptoalloteichus hindustanus* Phleomycin-Resistance Protein (Sh-ble).

C1 strains NG7C-19 and UV18-25 were transformed by the plasmid pUT720 (ref. 1). This vector presents the following fungal expression cassette:

*Aspergillus nidulans* glyceraldehyde-3-phosphate dehydrogenase (gpdA) promoter (ref. 2)

A synthetic *Trichoderma reesei* cellobiohydrolase I (cbh1) signal sequence (refs 1, 3)

*Streptoalloteichus hindustanus* phleomycin-resistance gene Sh-ble (ref. 4)

*Aspergillus nidulans* tryptophan-synthase (trpC) terminator (ref. 5)

Figure 2:
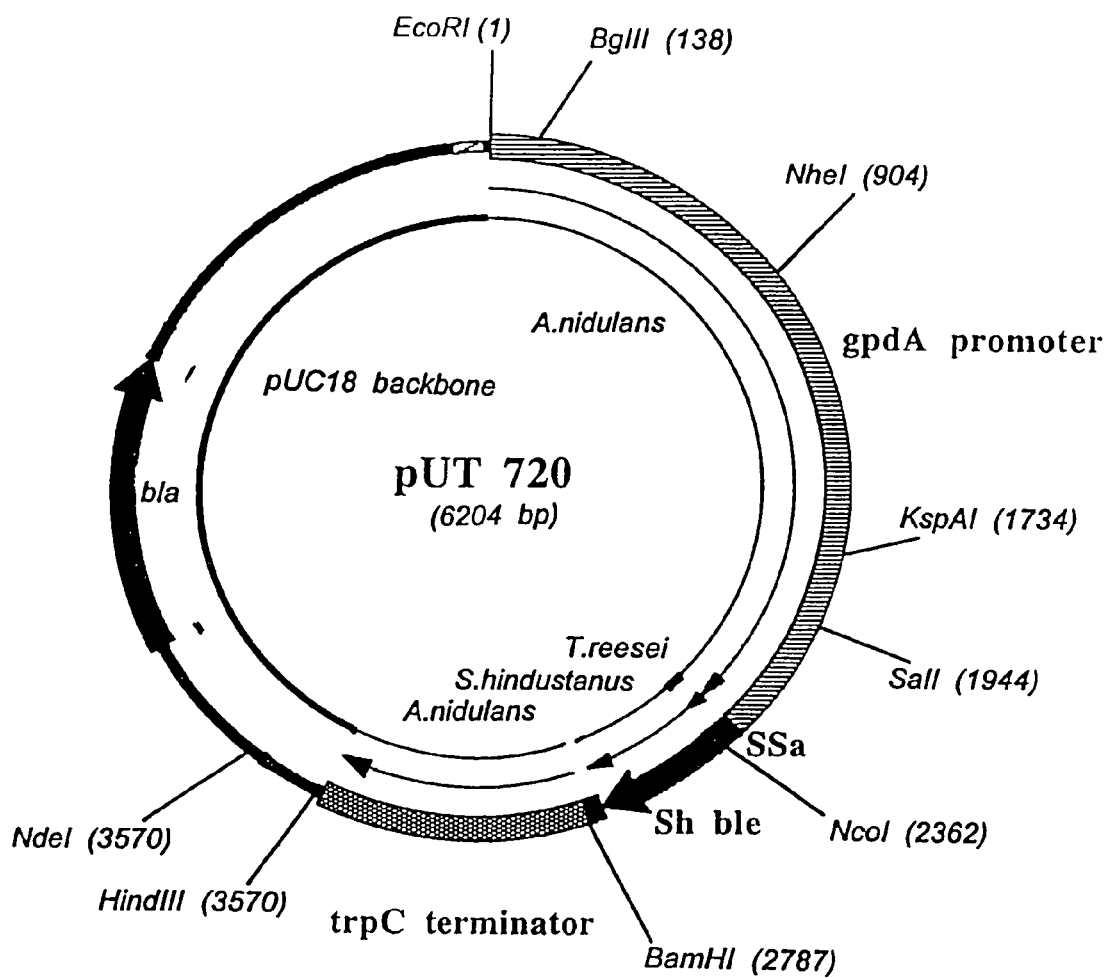
FIG. 2 is a pUT720 map.

The vector also carries the beta-lactamase gene (bla) and *E. coli* replication origin from plasmid pUC18 (Ref 6). The detailed plasmid map is provided in FIG. 2.

C1 protoplasts were transformed according to Durand et al. (ref. 7) adapted to C1: All spores from one 90 mm PDA plate of untransformed C1 strain were recovered in 8 ml IC1 and transferred into a shake flask with 50 ml IC1 medium for incubation 15 hours at 35° C. and 150 rpm. Thereupon, the culture was spun down, the pellet washed in MnP, resolved in 10 ml MnP+10 mg/ml Caylase $C_3$, and incubated 30 min at 35° C. with agitation (150 rpm). The solution was filtered and the filtrate was centrifuged 10 min at 3500 rpm. The pellet was washed with 10 ml MnPCa$^{2+}$. This was spun down 10 min at 3500 rpm and the pellet was taken up into ml MnPCa$^{2+}$. 10 µg of pUT720 DNA were added to 200 µl of protoplast solution and incubated 10 min at room temperature (ca. 20° C.). Then, 50 µl of cold MPC was added. The mixture was kept on ice for 30 min whereupon 2.5 ml PMC was added. After 15 min at room temperature 500 µl of the treated protoplasts were mixed to 3 ml of MnR Soft and immediately plated out on a MnR plate containing phleomycin (50 µg/ml at pH6.5) as selection agent. After 5 days incubation at 30° C., transformants were analysed (clones start to be visible after 48 hours).

The Sh-ble production of C1 transformants (phleomycin-resistant clones) was analysed as follows: Primary transformants were toothpicked to GS+phleomycin (5 µg/ml) plates and grown for 5 days at 32° C. for resistance verification. Each validated resistant clone was subcloned onto GS plates. Two subclones per transformant were used to inoculate PDA plates in order to get spores for liquid culture initiation. The liquid cultures in IC1 were grown 5 days at 27° C. (shaking 200 rpm). Then, the cultures were centrifuged (5000 g, 10 min.) and 500 µl of supernatant were collected. From these samples, the proteins were precipitated with TCA and resuspended in Western Sample Buffer to 4 mg/ml of total proteins (Lowry method, Ref. 8). 10 µl (about 40 µg of total proteins) were loaded on a 12% acrylamide/SDS gel and run (Mini Trans-Blot™ system, BioRad Laboratories). Western blotting was conducted according to BioRad instructions (Schleicher & Schull 0.2 µm membrane) using rabbit anti-Sh-ble antiserum (Societe Cayla, Tolouse FR, Catalog #ANTI-0010) as primary antibody. The results are shown in FIG. 1 and Table E.

TABLE E

Sh-ble estimated production levels in C1

| | Estimated Sh-ble quantity on the Western blot | Estimated Sh-ble concentration in the production media |
|---|---|---|
| Untransformed NG7C-19 | Not detectable | |
| NG7C-19::720 clone 4-1 | 25 ng | 0.25 mg/l |
| NG7C-19::720 clone 5-1 | 25 ng | 0.25 mg/l |
| NG7C-19::720 clone 2-2 | 250 ng | 2.5 mg/l |
| Untransformed UV18-25 | Not detectable | |
| UV18-25::720 clone 1-2 | 500 ng | 5.0 mg/l |
| UV18-25::720 clone 3-1 | 250 ng | 2.5 mg/l |

These data show that:

1) The heterologous transcription/translation signals from pUT720 are functional in *Chrysosporium*.

2) The heterologous signal sequence of pUT720 is functional in *Chrysosporium*.

3) *Chrysosporium* can be used a host for the secretion of heterologous bacterial proteins.

(2) C1 Secretion of Human Lysozyme (HLZ).

C1 strains NG7C-19 and UV18-25 were transformed by the plasmid pUT970G (ref. 9). This vector presents the following fungal expression cassette:

*Aspergillus nidulans* glyceraldehyde-3-phosphate dehydrogenase (gpdA) promoter (ref. 2)

A synthetic *Trichoderma reesei* cellobiohydrolase I (cbh1) signal sequence (refs. 1, 3)

*Streptoalloteichus hindustanus* phleomycin-resistance gene Sh-ble 4 used as carrier protein (ref. 10)

*Aspergillus niger* glucoamylase (glaA2) hinge domain cloned from plasmid pAN56-2 (refs. 11, 12)

A linker peptide (LGERK) (SEQ ID NO: 5) featuring a KEX2-like protease cleavage site (ref. 1)

A synthetic human lysozyme gene (hlz) (ref. 10)

*Aspergillus nidulans* tryptophan-synthase (trpC) terminator (ref. 5).

Figure 3:
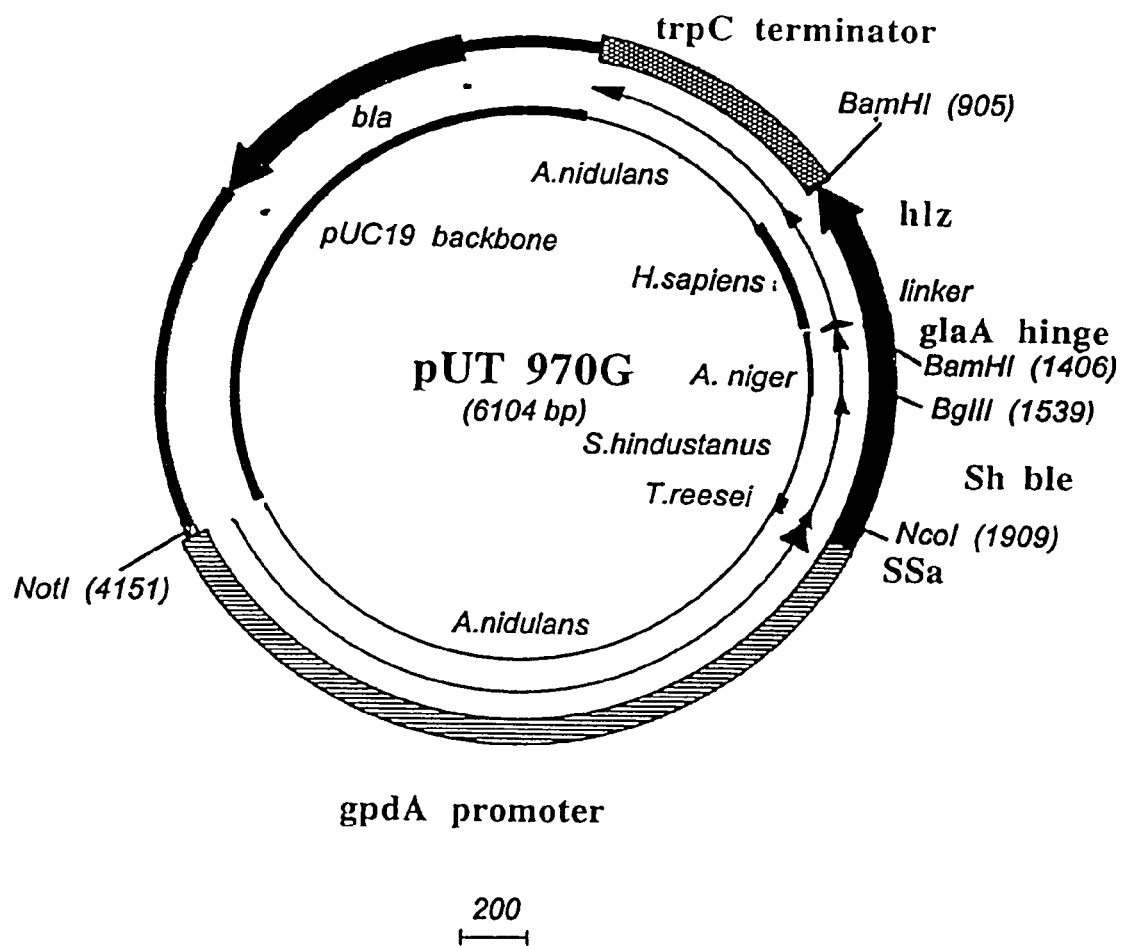
FIG. 3 is a pUT970G map.

The vector also carries the beta-lactamase gene (bla) and *E. coli* replication origin from plasmid pUC18 6. The detailed plasmid map is provided in FIG. 3.

C1 protoplasts were transformed with plasmid pUT970G following the same procedure already described in example 1. The fusion protein (Sh-ble::GAM hinge::HLZ) is functional with respect to the phleomycin-resistance thus allowing easy selection of the C1 transformants. Moreover, the level of phleomycin resistance correlates roughly with the level of hlz expression.

The HLZ production of C1 transformants (phleomycin-resistant clones) was analysed by lysozyme-activity assay as follow: Primary transformants were toothpicked to GS+phleomycin (5 μg/ml) plates (resistance verification) and also on LYSO plates (HLZ activity detection by clearing zone visualisation (refs. 1, 10). Plates were grown for 5 days at 32° C. Each validated clone was subcloned onto LYSO plates. Two subclones per transformant were used to inoculate PDA plates in order to get spores for liquid culture initiation. The liquid cultures in IC1 were grown 5 days at 27° C. (shaking 180 rpm). Then, the cultures were centrifuged (5000 g, 10 min.). From these samples, lysozyme activity was measured according to Mörsky et al. (ref. 13)

TABLE F

Active HLZ production levels in C1

| | Active HLZ concentration in culture media |
|---|---|
| Untransformed NG7C-19 | 0 mg/l |
| NG7C-19::970G clone 4 | 4 mg/l |
| NG7C-19::970G clone 5 | 11 mg/l |
| Untransformed UV18-25 | 0 mg/l |
| UV18-25::970G clone 1 | 8 mg/l |
| UV18-25::970G clone 2 | 4 mg/l |
| UV18-25::970G clone 3 | 2 mg/l |
| UV18-25::970G clone 2 | 2.5 mg/l |

These data show that:

1) Points 1 & 2 from example 1 are confirmed.

2) Sh-ble is functional in *Chrysosporium* as resistance marker.

3) Sh-ble is functional in *Chrysosporium* as carrier protein.

4) The KEX2-like protease cleavage site is functional in *Chrysosporium* (otherwise HLZ would not be active).

5) *Chrysosporium* can be used as host for the secretion of heterologous mammalian proteins.

(3) C1 Secretion of *Trichoderma reesei* Xylanase II (XYN2).

C1 strain UV18-25 was transformed by the plasmids pUT1064 and pUT1065.

pUT1064 presents the two following fungal expression cassettes:

The first cassette allows the selection of phleomycin-resistant transformants:

*Neurospora crassa* cross-pathway control gene 1 (cpc-1) promoter (ref. 14)

*Streptoalloteichus hindustanus* phleomycin-resistance gene Sh-ble (ref. 4)

*Aspergillus nidulans* tryptophan-synthase (trpC) terminator (ref. 5)

The second cassette is the xylanase production cassette:

*T. reesei* strain TR2 cbh1 promoter (ref. 15)

*T reesei* strain TR2 xyn2 gene (including its signal sequence) (ref. 16)

*T reesei* strain TR2 cbh1 terminator (ref. 15)

Figure 4:
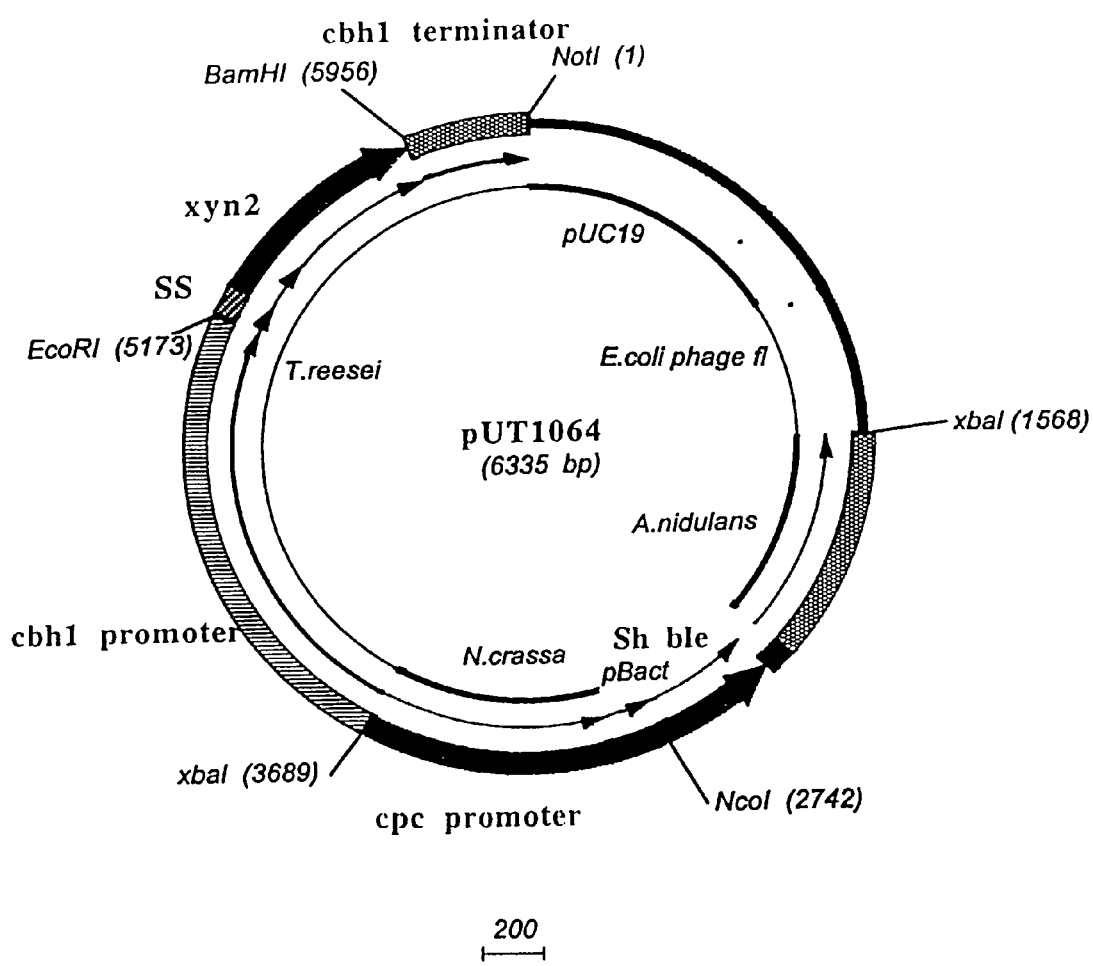
FIG. 4 is a pUT1064 map.

The vector also carries an *E. coli* replication origin from plasmid pUC19 (ref. 6). The detailed map is provided in FIG. 4.

pUT1065 presents the following fungal expression cassette:

*A. nidulans* glyceraldehyde-3-phosphate dehydrogenase (gpdA) promoter (ref. 2)

A synthetic *T. reesei* cellobiohydrolase I (cbh1) signal sequence (refs. 1, 3)

*S. hindustanus* phleomycin-resistance gene Sh-ble 4 used as carrier-protein (ref. 10)

A linker peptide (SGERK) (SEQ ID NO: 6) featuring a KEX2-like protease cleavage site (ref1)

*T. reesei* strain TR2xyn2 gene (without signal sequence) (ref. 16)

*A. nidulans* tryptophan-synthase (trpC) terminator (ref. 5).

Figure 5:
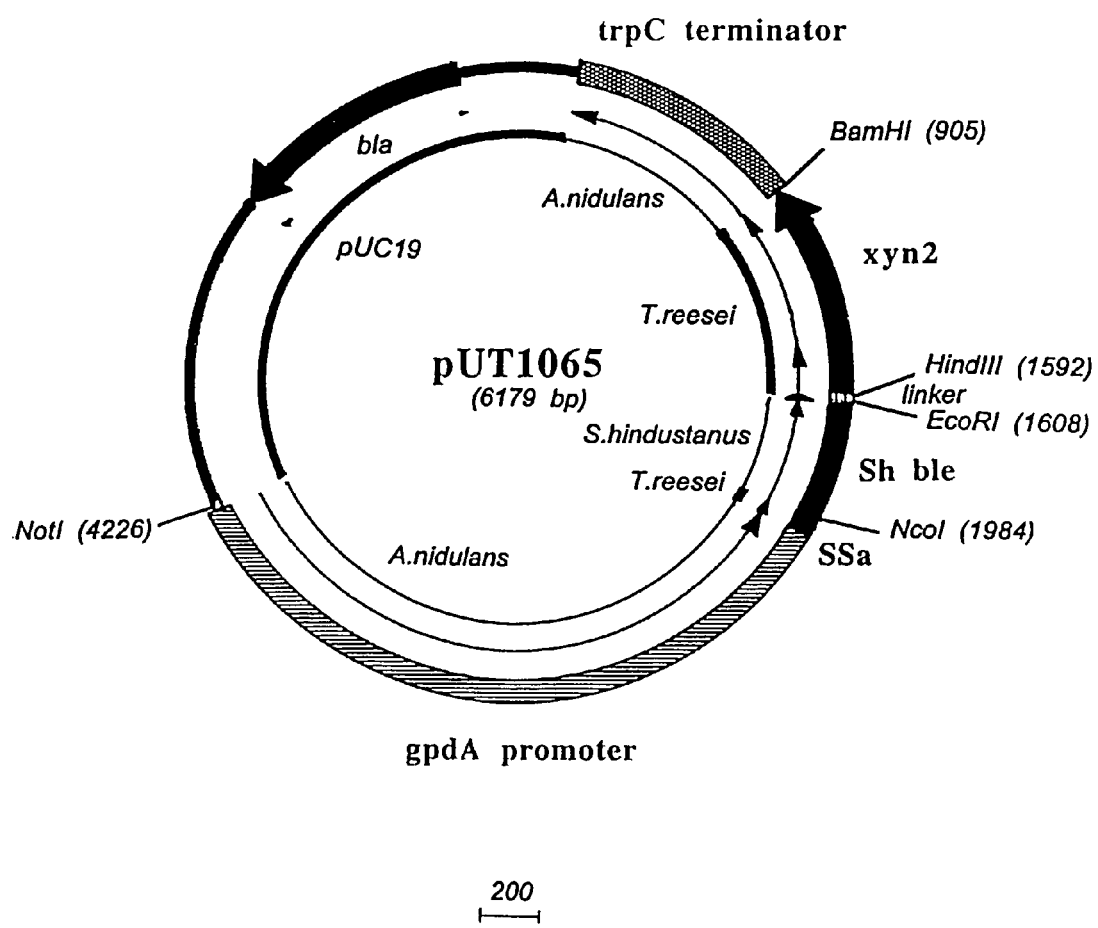
FIG. 5 is a pUT1065 map.
Figure 6:
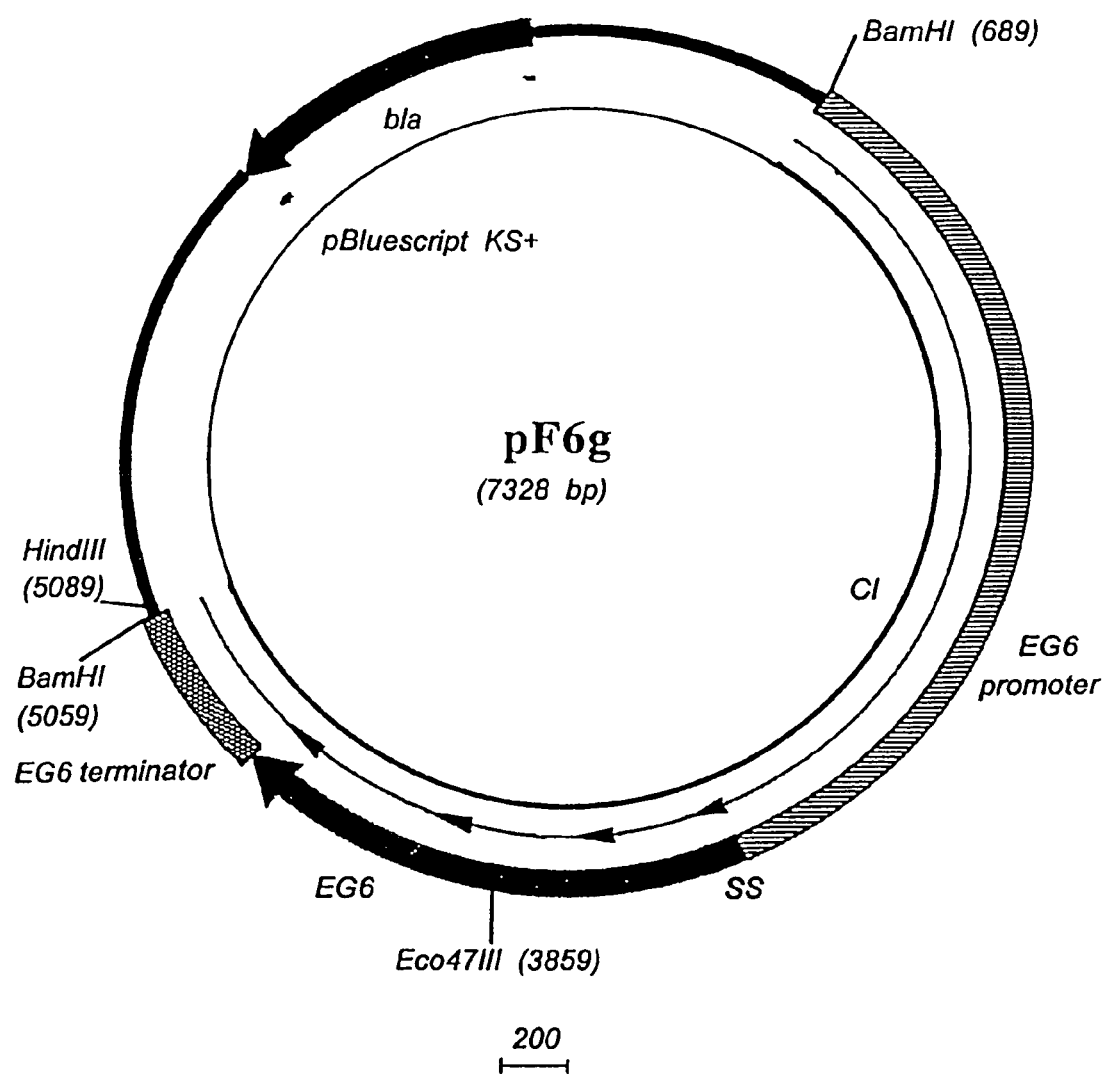
FIG. 6 is a pF6g map.
Figure 7:
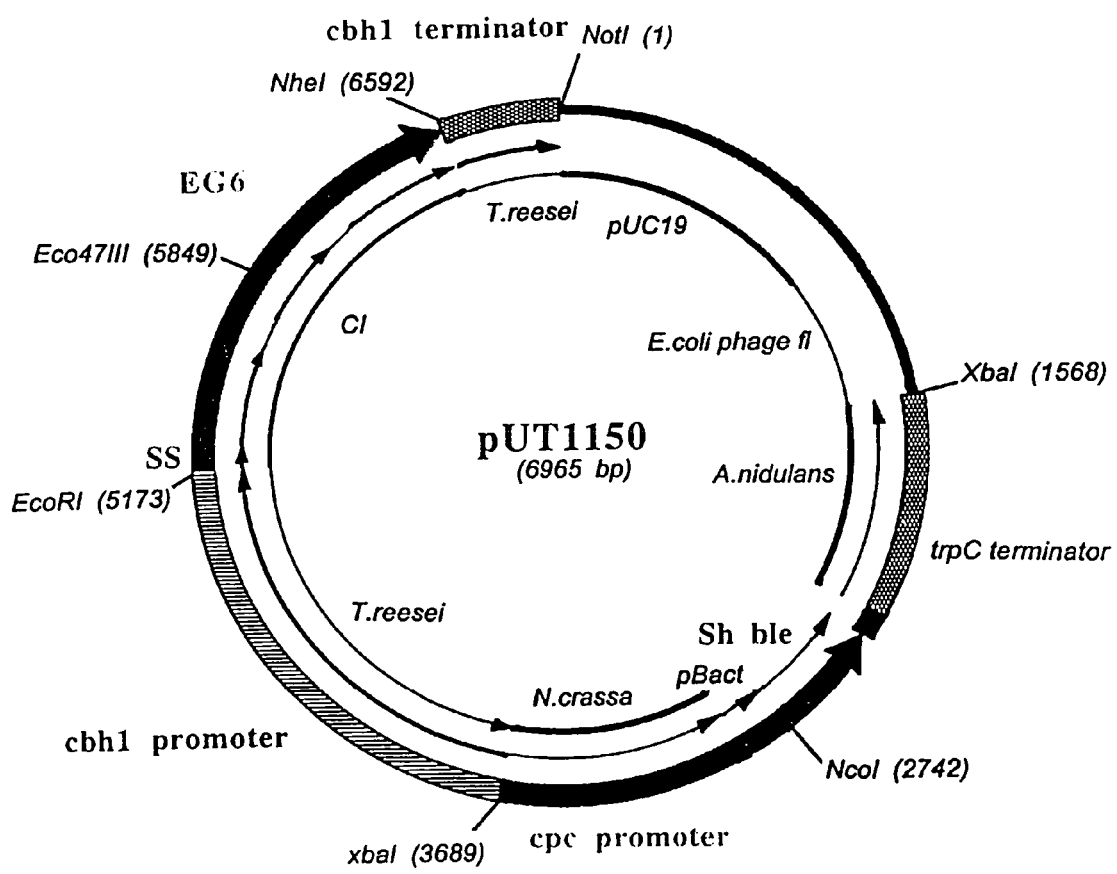
FIG. 7 is a pUT1150 map.
Figure 8:
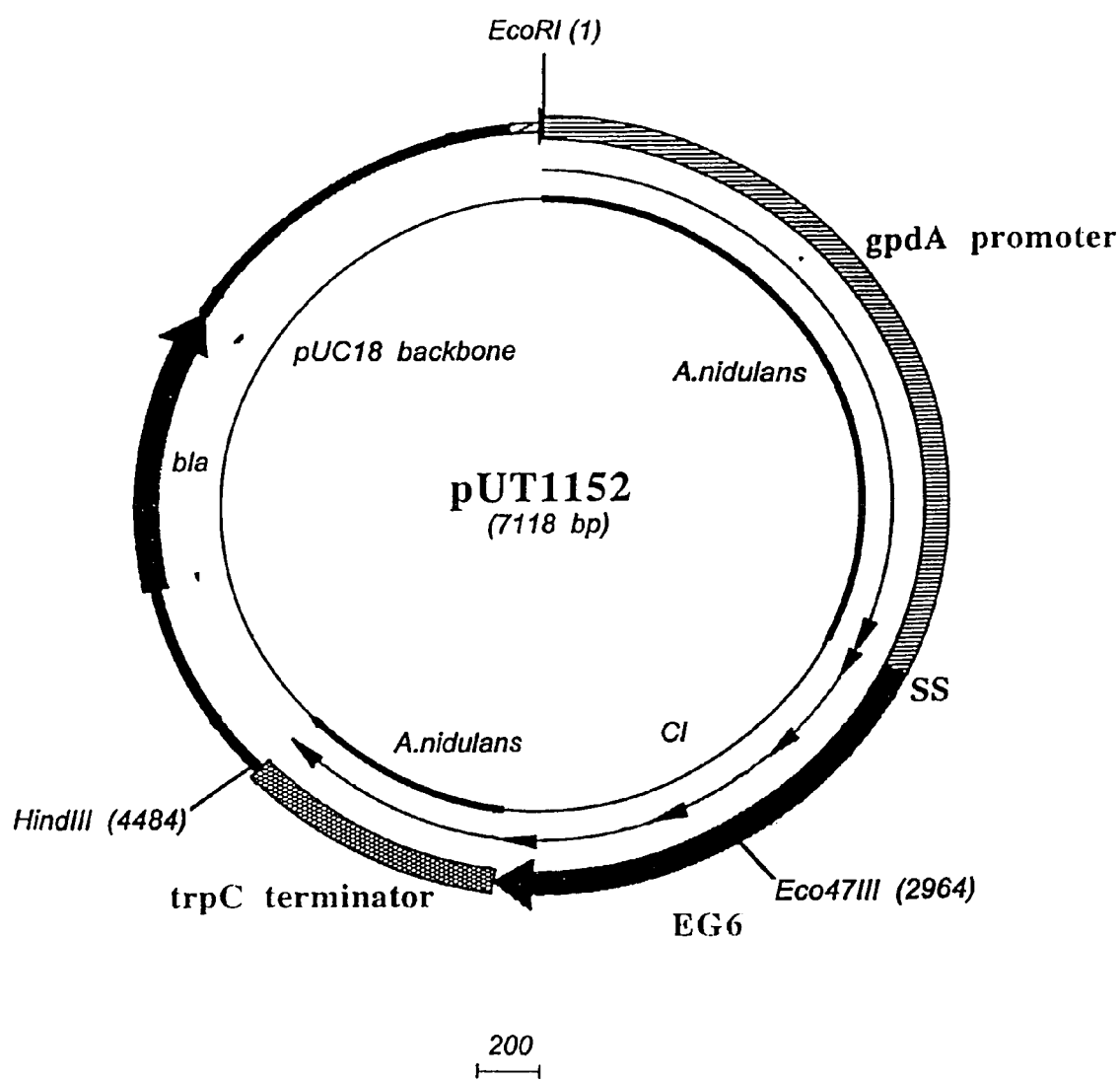
FIG. 8 is a pUT1152 map.
Figure 9:
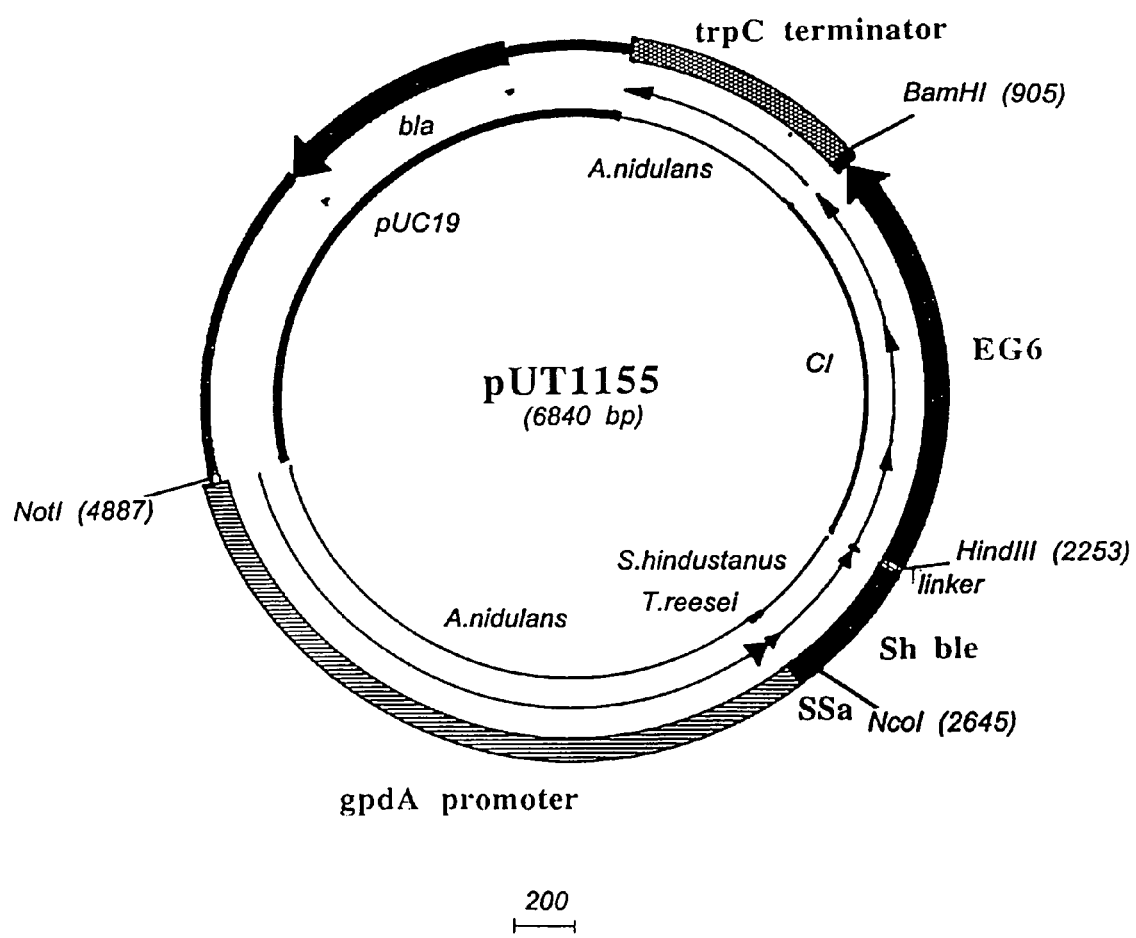
FIG. 9 is a pUT1155 map.
Figure 10:
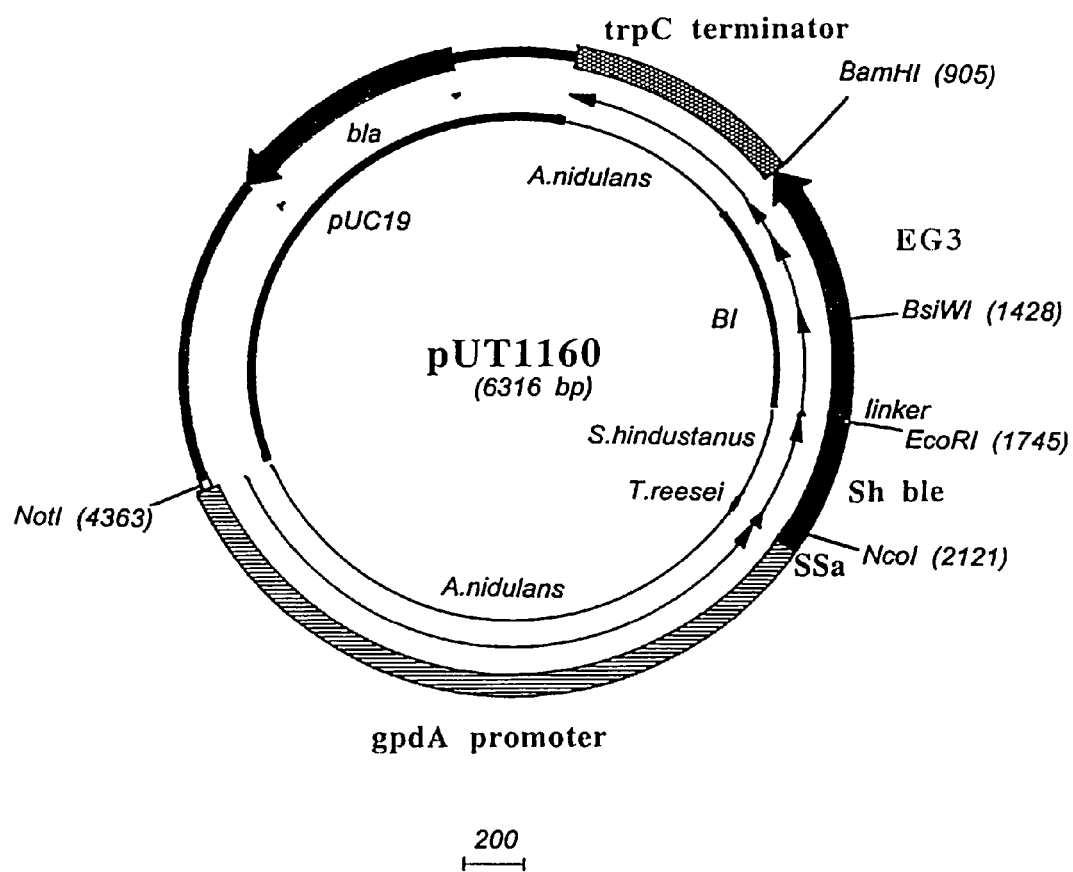
FIG. 10 is a pUT1160 map.
Figure 11:
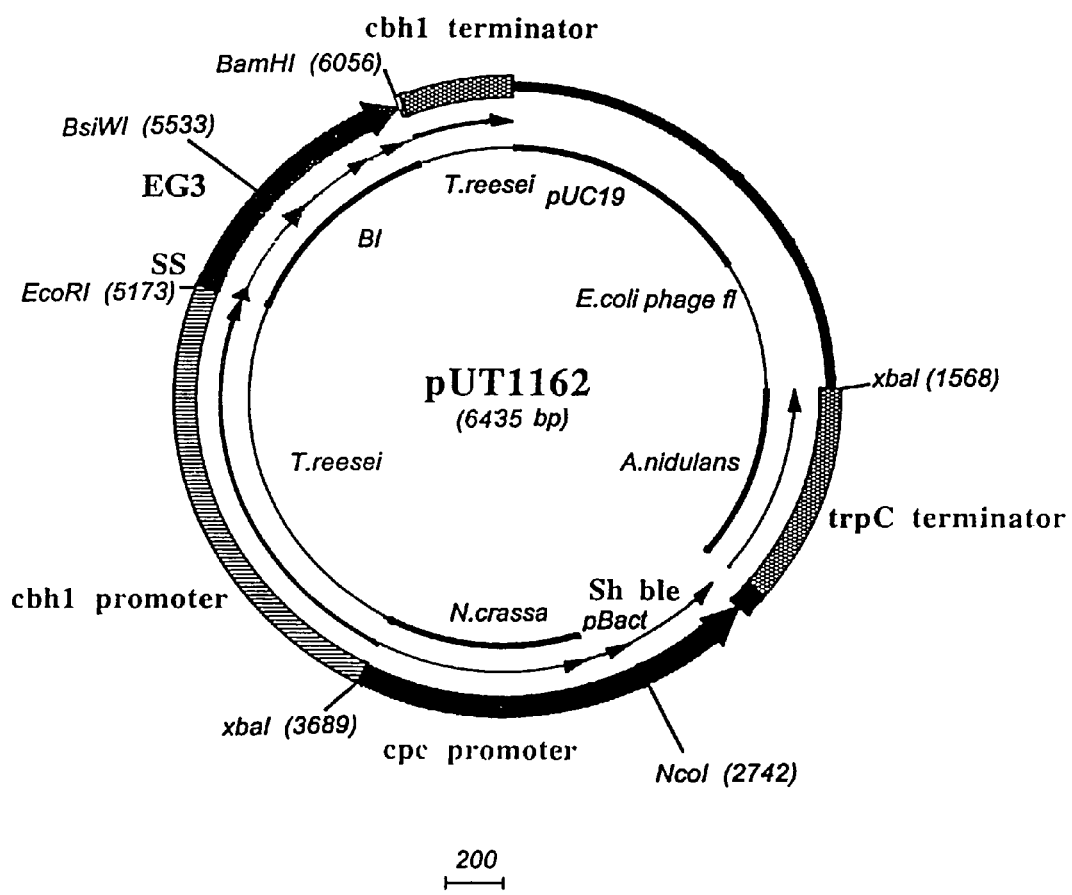
FIG. 11 is a pUT 1162 map.
Figure 12:
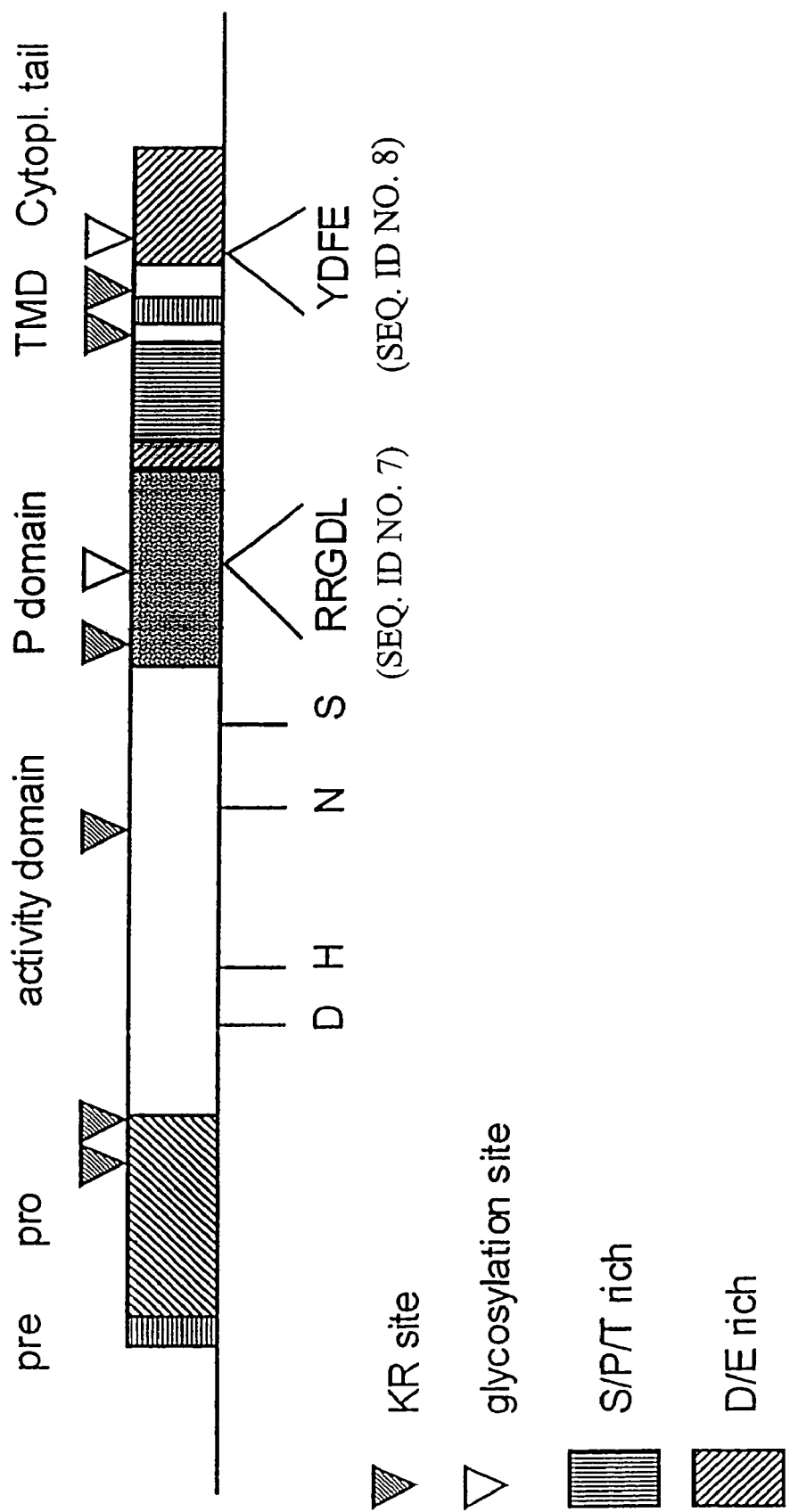
FIG. 12 is the schematic structure of the pclA protein.

The vector also carries the beta-lactamase gene (bla) and an *E. coli* replication origin from plasmid pUC18 (Ref. 6). The plasmid detailed map is provided in FIG. 5.

C1 protoplasts were transformed with plasmid pUT1064 or pUT1065 following the same procedure already described in example 1. The fusion protein in plasmid pUT1065 (Sh-ble::XYN2) is functional with respect to the phleomycin-resistance thus allowing easy selection of the C1 transformants. Moreover, the level of phleomycin resistance correlates roughly with the level of xyn2 expression. In pUT1064, xyn2 was cloned with its own signal sequence.

The xylanase production of C1 transformants (phleomycin-resistant clones) was analysed by xylanase-activity assay as follow: Primary transformants were toothpicked to GS+phleomycin (5 µg/ml) plates (resistance verification) and also on XYLAN plates (Ref. 17), where xylanase activity is detected by observation of a clearing zone. Plates were grown for 5 days at 32° C. Each validated clone was subcloned onto XYLAN plates. Two subclones per transformant were used to inoculate PDA plates in order to get spores for liquid culture inoculation. The liquid cultures in IC1+5 g/l $K^+$ Phtalate were grown 5 days at 27° C. (shaking 180 rpm). Then, the cultures were centrifuged (5000 g, 10 min.). From these samples, xylanase activity was measured by DNS Technique according to Miller et al. (ref. 18)

TABLE G

Active XYN2 production levels in C1 (best producers)

| | Active xylanase II concentration in culture media | Xylanase II specific activity in culture media |
|---|---|---|
| Untransformed UV18-25 | 3.9 U./ml | 3.8 U./mg total prot. |
| UV18-25::1064 clone 7-1 | 4.7 U./ml | 4.7 U./mg total prot. |
| UV18-25::1064 clone 7-2 | 4.4 U./ml | 4.3 U./mg total prot. |
| UV18-25::1065 clone 1-1 | 29.7 U./ml | 25.6 U./mg total prot. |
| UV18-25::1065 clone 1-2 | 30.8 U./ml | 39.4 U./mg total prot. |

These data show that:

1) Points 1 to 4 from example 2 are confirmed.

2) C1 can be used as host for the secretion of heterologous fungal proteins.

(4) Summary

Table H shows the results for the plasmids with which transformation of UV18-25 was carried out. The Table shows expression levels for endoglucanase and cellobiohydrolase using heterologous expression regulating sequences and signal sequences and also with homologous expression regulating sequences and signal sequences. The details of the various plasmids can be derived elsewhere in the description and from the figures. The production occurs at alkaline pH at a temperature of 35° C.

TABLE H

Expression data of transformed UV18-25 strain (% relative to parent UV18-25 strain)

| | Total proteins | CMCase | | β-glucanase | | |
|---|---|---|---|---|---|---|
| Culture | mg/ml | u/ml | u/mg | u/ml | u/mg | pH value |
| UV 18-25 | 100% | 100% | 100% | 100% | 100% | 7.90 |
| 1150-23 | 94% | 105% | 111% | 140% | 149% | 7.90 |
| -30 | 96% | 105% | 110% | 145% | 151% | 8.10 |
| 1152-3 | 94% | 112% | 120% | 147% | 156% | 7.85 |
| -4 | 100% | 105% | 105% | 132% | 132% | 7.90 |
| 1160-2 | 69% | 81% | 118% | 90% | 131% | 7.90 |
| -4 | 73% | 72% | 98% | 83% | 114% | 8.35 |
| -1 | 92% | 95% | 103% | 120% | 130% | 8.45 |

TABLE H-continued

Expression data of transformed UV18-25 strain (% relative to parent UV18-25 strain)

| | Total proteins | CMCase | | β-glucanase | | |
|---|---|---|---|---|---|---|
| Culture | mg/ml | u/ml | u/mg | u/ml | u/mg | pH value |
| 1162-1 | 102% | 105% | 103% | 145% | 142% | 8.20 |
| -11 | 112% | 109% | 98% | 115% | 103% | 8.20 |
| F6g-20 | 104% | 102% | 98% | 130% | 125% | 7.90 |
| -25 | — | — | — | — | — | — |

Culture conditions (shake flask): 88 h, 35° C., 230 rpm

E. Construction of an *Aspergillus sojae* Gene Library (1) Vector Library

Genomic DNA of *A. sojae* was isolated from protoplasts obtained from ATCC 11906 using a previously described protocol (Punt, van den Hondel, *Methods Enzymol.* 1992 216:447-457). After isolation DNA was extracted from the protoplasts using the protocol described by Kolar et al., *Gene* 1988 62:127-34. Subsequently the DNA was partially digested with MboI to result in DNA fragments of an average size of 30-50 kb.

Vector pAOpyrGcosarp1, which was used for the construction of the gene library was constructed by ligation of a 3 kb BamHI-HindIII fragment from pANsCos1 (Osiewacz, *Curr. Genet.* 1994 26:87-90) and a 3.2 kb Acc65I-HindIII fragment from pAO4.2 (De Ruiter-Jacobs et al., *Curr. Genet.* 1989 16:159-63) in Acc65I-BamHI digested pHELP1 (Gems et al., *Gene* 1991 98:61-67). This cosmid vector carries the *A. oryzae* pyrG selection marker and is self-replicating in filamentous fungi.

MboI digested genomic DNA was ligated to BamHI-digested pAOpyrGcosarp1, and the ligation mixture was packaged into phage particles using the Stratagene Supercos1 vector kit (Stratagene Inc., La Jolla Calif.). This resulted in a total of ca. 30,000 individual clones, representing an approximate 30-fold representation of the *A. sojae* genome. Stocks (in 15% glycerol) of pools of the resulting clones were stored at –80° C. for later use.

(2) High-frequency Transformation

An *A. sojae* ATCC 11906 pyrG mutant was selected as a fluoroorotic acid-resistant derivative from ATCC 11906, as described in WO 01/09352. This strain, *A. sojae* ATCC 11906pyrG, was transformed with two vectors carrying the *A. niger* pyrG gene. One vector pAB4-1 (van Hartingsveldt et al, *Mol. Gen. Genet.* 206:71-75 (1987)) carries only the pyrG gene, whereas pAB4-arp1 (Verdoes et al., *Gene* 146:159-165 (1994)) carries the pyrG gene and the *A. nidulans* AMA1 sequence. Transformation of ATCC 11906pyrG results in 5-10 transformants per microgram DNA from pAB4-1, whereas with pAB4-arp1 frequency were at least 10-100 fold higher. Phenotypic analysis of the transformants revealed that the pyrG phenotype of the pAB4-arp1 transformants was maintained only under continuous selection, whereas the pAB4-1 transformants were stable with and without selection for the pyrG phenotype. These results confirm autonomous replication of the introduced plasmid DNA in pAB4-arp1 transformants. Similar results were obtained with alternative fungal transformation vectors carrying the AMA1 sequence or derivatives thereof, e.g. pAOpyrGcosarp1.

(3) Construction of a Fungal Transformant Library

*A. sojae* ATCC11906pyrG or relevant mutants, in particular compact morphology mutants thereof, was transformed with an *A. sojae* gene library based on transformation vector pAOpyrGcosarp1. This vector results in a high frequency of transformants with freely replicating vector copies. Fungal protoplasts were treated as described in Punt and van den Hondel, *Methods Enzymol.* 1992 216:447-457 with DNA from a cosmid library carrying genomic fungal DNA clones from *A. sojae* or *Chrysosporium* and serial dilutions of the transformed protoplasts were plated on selective agar plates to determine the transformation frequency obtained. The remaining protoplasts were regenerated in selective medium for a few hours and stored at 4° C. Based on the results obtained for the transformation frequency (which depending of the experiment will reach values up to several thousand transformants per microgram of cosmid library DNA), limiting dilutions of the regenerated protoplasts were plated in microtiter plates of 96, 248, or alternative well format, resulting in one transformed protoplast per well. Plates were incubated at 35° C. to form fungal biomass. The resulting transformant library is used for further experiments.

A similar strategy was used for the construction of a collection of fungal transformants carrying mutant alleles of *Chrysosporium* CBH1. This strategy can also be used with a library of mutants derived from any other gene of interest, whether generated by mutagenesis, gene shuffling or gene-evolution approaches.

F. Induction of Sporulation in Submerged Fermentation

Many fungi, such as *Aspergillus sojae*, do not show sporulation under submerged fermentation. Here we describe a previously unknown approach to obtain sporulation under these conditions. *A. sojae* ATCC 11906 and in particular compact growth morphology mutants thereof were grown in a synthetic growth medium supplemented with Yeast extract. Under these conditions rapid accumulation of biomass occurs in both static and agitated cultures. However, no sporulation occurs in the culture fluid. A similar growth medium with the addition of 0.6 g/kg EDTA results in considerable yields of spores reaching up to $10^9$ spores per ml culture fluid after incubation of 2-4 days at 35° C.

Synthetic Medium (+/−EDTA):

|  | g/kg medium |
|---|---|
| $KH_2PO_4$ | 2.5 |
| $NH_4Cl$ | 7.2 |
| $MgSO_4.7H_2O$ | 0.7 |
| $CaCl_2.2H_2O$ | 0.2 |
| Yeast Extract | 20 |
| $ZnSO_4.7H_2O$ | 0.015 |
| $CoCl_2.6H_2O$ | 0.005 |
| $CuSO_4.5H_2O$ | 0.016 |
| $FeSO_4.7H_2O$ | 0.040 |
| $H_3BO_4$ | 0.005 |
| KI | 0.003 |
| $MnCl_2.2H_2O$ | 0.012 |
| $Na_2MoO_4.2H_2O$ | 0.003 |
| EDTA | (0.6 or 0.0) |

PH adjusted to 5.5 with $NaOH/H_3PO_4$

G. Transformation Systems for *Chrysosporium* and *Aspergillus*

(1) Cloning of the *A. niger* Orotate p-ribosyl Transferase Gene pyrE

Numerous versatile transformation systems for filamentous fungi are based on the use of uridine-requiring mutant strains. These mutant strains are either deficient in orotidine 5 phosphate decarboxylase (OMPD) or orotate p-ribosyl transferase (OPRT). (T. Goosen et al., *Curr Genet.* 1987, 11:499-503; J. Begueret et al., *Gene.* 1984 32:487-92.) Previously we have isolated the *A. niger* OMPD gene pyrG (W. van Hartingsveldt et al., *Mol. Gen. Genet.* 1987 206:71-5). The cloning of the *A. niger* OPRT gene (pyrE) was carried out by complementation of an *A. niger* FOA-resistant uridine-requiring non-pyrG mutant. For complementation an *A. niger* cosmid library in vector pAOpyrGcosarp1 was used. From the complementing transformants, genomic cosmid clones were isolated, carrying the complementing *A. niger* gene, termed now pyrE. A 5.5 kb SstII fragment carrying the pyrE gene was cloned in pBLUESCRIPT™ (Stratagene) resulting in vector pBLUEpyrE. A 1.6 kb fragment of this vector spanning the pyrE coding region was sequenced to confirm the location of the OPRT gene (See FIG. 15).

(2) Auxotrophic Transformation System for *Chrysosporium lucknowense*

Uridine-requiring *Chrysosporium lucknowense* strains were selected as fluoroorotic acid resistant derivatives from C1 and UV18-25 by methods described in PCT publication WO 01/09352. Selection of fluoro-orotic acid resistant derivatives may result in the isolation of two types of uridine-requiring mutants, i.e. either orotidine 5 phosphate decarboxylase (OMPD) mutants or orotate p-ribosyl transferase (OPRT)mutants (T. Goosen et al., *Curr Genet.* 1987, 11:499-503). To determine the nature of the *Chrysosporium* mutants obtained, transformation experiments were carried out with the available *A. niger* genes pyrG (OMPD; vector pAB4-1, W. van Hartingsveldt et al., *Mol. Gen. Genet.* 1987 206:71-5) and pyrE (pBLUE-pyrE; OPRT). As shown in Table I, only transformation of the mutant strains with the pyrE gene resulted in prototrophic transformants, implying that the *Chrysosporium* strains are OPRT mutants. Following the *Chrysosporium* gene nomenclature we have adopted, the mutants were designated pyr5.

TABLE I

| Gene | Source | Vector[1-4] | UV18FOA$^R$#4 | C1#B |
|---|---|---|---|---|
| OMPD | *Aspergillus niger* | pAB4-1 | − | − |
| (PyrG/pyr4) | *Aspergillus oryzae* | pAO4-2 | − | − |
| | *Neurospora crassa* | pDJB3 | − | − |
| OPRT | *Aspergillus niger* | pBLUEpyrE | + | + |
| (pyrE/pyr5) | | | | |

[1]pAB4-1: W. van Hartingsveldt et al., Mol. Gen. Genet. 1987 206: 71-5.
[2]pAO4-2: Y. de Ruiter-Jacobs et al., Curr. Genet. 1989 16: 159-63.
[3]pDJB3: D. Ballance, G. Turner, Mol. Gen. Genet. 1986 202: 271-5.
[4]pBLUEpyrE: vide supra (3) Construction and Use of Autonomously Replicating Fungal Transformation Vectors.

Based on vector pBLUEpyrE two derivatives were generated carrying sequences providing autonomous replicative characteristics to the vectors when introduced in filamentous fungi. A 5.5 kb HindIII fragment carrying the *Aspergillus nidulans* AMA1 sequences (J. Verdoes et al., *Gene* 1994 146:159-65) was introduced in the unique HindIII site of pBLUEpyrE resulting in pBLUEpyrE-AMA. A 2.1 kb (partial) HindIII fragment carrying human telomeric sequences (A. Aleksenko, L. Ivanova, *Mol. Gen. Genet.* 1998 260:159-64) was introduced in the unique HindIII site of pBLUEpyrE resulting in pBLUEpyrE-TEL. These vectors were introduced into *Aspergillus* and *Chrysosporium* OPRT mutant strains resulting in prototrophic transformants. Several of the obtained transformants showed the ragged phenotype characteristic of transformants carrying freely replicating plasmids (J. Verdoes et al., *Gene* 1994 146:159-65).

(4) Transformation of *Chrysosporium lucknowense*

The protocol is based on a procedure originally used for *Aspergillus* transformation (P. Punt, C. van den Hondel, *Methods in Enzymology* 1992 216:447-457). Rich medium (250 ml) was inoculated with $10^6$ spores/ml of the pyr5 *Chrysosporium* mutant (supra) in a 1L Erlenmeyer flask. The culture was grown for 24-48 hours at 35° C. in an air incubator (300 rpm). The mycelium was filtered through a sterile Miracloth™ filter (Calbiochem) and washed with ca. 100 ml 1700 mosmol NaCl/CaCl$_2$ (0.27 M CaCl$_2$/0.6 M NaCl). The mycelium was weighed and then kept on ice. Caylase™ (Cayla) was added (20 mg per gram mycelium) and 1700 mosmol NaCl/CaCl$_2$ (3.3 ml/g mycelium) and the suspension was incubated in a 33° C. air incubator (100 rpm). The protoplasting was followed under the microscope. After 1-3 hours of incubation, most of the mycelium was digested, leaving mostly protoplasts in the microscopic view of the preparation. The protoplasts were filtered through a sterile Myracloth filter and the filter was washed with 1 volume cold STC1700 (1.2 M sorbitol/10 mM Tris.HCl pH 7.5/50 mM CaCl$_2$/35 mM NaCl). The protoplasts were spun down at 2500 rpm for 10 minutes at 4° C. The pellet was resuspended in STC1700 and centrifuged again. After resuspending the pellet in STC1700, the protoplasts were counted. STC1700 was added to a final concentration of $2\times10^8$ protoplasts per ml.

Vector DNA (pAB4-1 or pBLUE-pyrE, 1-10 µg) was pipetted into the bottom of a sterile tube and 1 µl 1 M ATA (aurintricarbonic acid) and 100 µl protoplasts (ca. $2\times10^7$) were added to the DNA. A minus DNA negative control was included in the experiment. After mixing, the protoplasts were incubated at room temperature for 25 minutes. PEG6000 (60% PEG/50 mM CaCl$_2$/10 mM Tris pH 7.5) was added portionwise as follows: 250 µl, mix, 250 µl, mix, 850 µl and mix. The solution was kept at room temperature for 20 minutes. The tubes were then filled with 8 ml STC1700, mixed and centrifuged at 2500 rpm for 10 minutes at 4 C, and the pellet was suspended in 250 µl STC1700. Aloquots of the sample were used for plating on selective medium. For pyr$^+$ selection, plates were prepared containing 1.5% Daishin agar, 1.2 M sorbitol, 1×AspA with nitrate, 2 mM MgSO$_4$.7H$_2$O, 1× trace elements, 0.1% casaminoacids and 1% glucose. If selected for amdS (and pyr$^+$), the plates contained 1.5% Oxoid agar, 1.2 M sorbitol, 2 mM MgSO$_4$.7H$_2$O, 1× trace elements, 1% glucose, 1×AspA without nitrate, 15 mM CsCl and 10 mM acetamide or acrylamide. The plates were incubated at 30 or 35° C.

The spores and viable protoplasts before and after PEG6000 treatment were counted by plating dilutions in STC 1700 on minimal medium plates with nitrate and with or without sorbitol. 100 µl of $10^-$, $10^{-2}$ and $10^{-3}$ dilutions were plated on plates without sorbitol to count for spores and 100 µl of $10^-$, $10^{-3}$, $10^{-4}$ and $10^{-5}$ dilutions were plated on plates with sorbitol to count the viable protoplasts.

Results of the transformations are shown in Table I.

H. Protein/Biomass Ratios

For *Chrysosporium*, *Trichoderma*, and *Aspergillus* strains producing cellulases or amylases, total dry solids were determined by passing a measured aliquot of the whole broth through a preweighed filter, washing with deionized water, and drying the cake and filter overnight at 60° C. and for one hour at 100° C. After cooling in a dessicator, biomass was determined by subtracting the weight of the filter from the weight of the dry filter plus filter cake and dividing by the volume of broth removed.

For *Trichoderma* and *Aspergillus* strains, the biomass was assumed to be equal to the total dry solids as there was little insoluble material other than biomass at the time measurements were taken. For *Chrysosporium* strains producing cellulase, there was a significant quantity of cellulose in the medium, so biomass was determined as the difference between total dry solids and cellulose. Cellulose was assayed as follows.

Measured aliquots of whole broth were centrifuged to remove solids and the supernatant was discarded. The pellet was resuspended into a volume of 0.1 N NaOH equal to the original broth volume and one tenth volume of 0.5 N NaOH was added. The mixture was incubated for four hours at 65° C. This treatment dissolved everything except the cellulose. The alkaline mixture was cooled and centrifuged, and the supernatant was discarded. The resulting pellet was washed twice by resuspension in deionized water and centrifugation. The washed pellet was resuspended in deionized water, transferred to a preweighed pan and dried as described above. Cellulose concentration was determined dividing the dry weight by the volume of the aliquot assayed.

Protein was determined by the Bradford dye-binding procedure (M. Bradford, 1976, *Anal. Biochem.* 72:248) using an immunoglobulin standard. Protein/biomass ratios for selected expressed proteins in various filamentous fungal strains are presented in Table J.

TABLE J

| Enzyme | Strain | g Protein per g Biomass |
| --- | --- | --- |
| Neutral Cellulase | *Chrysosporium lucknowense* UV18-25 | 8.2 |
| Neutral Cellulase | *Chrysosporium lucknowense* UV26-2 | 6.0 |
| α-Amylase | *Aspergillus oryzae* 108-318 | 0.89 |
| Glucoamylase | *Aspergillus niger* | 0.78 |
| Glucoamylase | *Aspergillus niger* | 1.11 |
| Acid Cellulase | *Trichoderma reesei* A-34 | 0.89 |
| Acid Cellulase | *Trichoderma reesei* A-1391 | 0.65 |
| Xylanase | *Trichoderma reesei* X-252 | 2.4 |

I. Expression and Secretion of Green Fluorescent Protein in *A. sojae* and *C. lucknowense*

As an example of a versatile and easily screenable reporter protein, Green Fluorescent Protein (GFP) from the jellyfish *Aequoria victoria* was expressed in *A. sojae* and *C. lucknowense*. Vectors carrying GFP (A. Santerre Henriksen et al., *Microbiology*. 1999, 145:729-734) and Glucoamylase-GFP fusion genes (pGPDGFP, C. Gordon et al., *Microbiology*. 2000 146:415-26) were modified by replacing the glaA promoter with the constitutively-expressed *A. nidulans* gpdA promoter. The vectors were introduced into *A. sojae* by cotransformation, using either the pyrG or amdS selection marker. Vector pGPDGFP and its derivatives were introduced in *Chrysosporium* by cotransformation using either the pyrE or amdS selection marker. Expression resulted in brightly fluorescent *A. sojae* and *Chrysosporium* transformants, confirming expression of GFP by both vectors. Fluorescence of culture supernatants from transformants expressing Glucoamylase-GFP fusion protein indicated secretion of the fluorescently active fusion protein. Expression of fluorescent protein was also observed in spores (or spore-like propagules) obtained from the various transformants expressing the non-secreted cytoplasmic version of the fluorescent proteins.

J. Transfer of Fungal Growth Units

The wells of a 96-well microtiter plate are loaded with an appropriate medium, either manually with a multi-channel pipet or by means of an automated plate-handling system. A large volume increases the chance of cross-infection, whereas to avoid problems with evaporation the volume should not be too small. If using the COSTAR™ 3799 round-bottom plate, for example, 150 μl is an appropriate volume to work with. Plates are inoculated with spores from plate-grown colonies using toothpicks for transfer. Alternatively, plates can be inoculated by pipetting small aliquots of suspensions of spores, protoplasts or hyphal elements. These suspensions may be derived from isolated spore/protoplast solutions or from microplate grown sporulating cultures. Inoculation can also be carried out from microtiter plates with the use of a pin or a 96-pin tool.

Subsequently plates are incubated at 35° C. To minimize evaporation, lidded plates may be employed, or the plates may be sealed with a membrane that allows exchange of $O_2$, $H_2O$ and $CO_2$ and sticks to the surface of the plate. To further limit evaporation, a controlled-atmosphere incubator may be used.

After three to four days of incubation, the amount of biomass is appropriate for efficient transfer to new microtiter plates containing fresh medium. For preparation of replica plates, a 96-pin tool is used. Daughter plates having different arrangements of the cultures may be prepared by manual or robotic pipetting or pin transfer. To ensure the presence of transferable reproducing elements on the transfer pins, the pin tool is submerged into the microtiter plate culture and shaken for 20 seconds. The pin tool is then carefully removed from the starting plate and a print is made into a new microtiter plate. A similarly efficient transfer procedure can also be achieved by using a multi-channel pipet, transferring about 1 μl of the parent microtiter plate culture. In both cases efficient transfer is achieved due to the presence of the transferable reproductive elements, such as spores, spore-like propagules, protoplasts, or hyphal or mycelial fragments. Protoplasts may be generated in the microplate wells by treatment with cell wall degrading enzymes and then transfer these protoplasts. Protoplast formation in microplates has been described by C. van Zeijl et al., *J Biotechnol*. 1997 59:221-224.

A further improvement of the transfer is obtained by incubating the microtiter plate cultures on a microtiter plate shaker at 35° C. This increases the number of transferable reproductive elements in the cultures. To store the microtiter plate cultures, glycerol is added to a 15% end concentration, and the plates are stored at −80° C. For subsequent transfer experiments plates are defrosted and transfer is carried out as described before.

Efficient transfer with wild-type or commercial strains of *A. niger* and *A. sojae* was not feasible under the conditions used here, as these strains showed vigorous surface growth and aerial sporulation after one day. Aerial sporulation causes massive cross-contamination during transfer, and surface growth covering the wells subsequently precludes a large proportion of known assay methods.

K. Construction of a Fungal Expression Library for Gene Discovery

Based on the fungal expression vector pAN52-1NOT (EMBL accession Z32524) or one of its derivatives, a vector was constructed in which a unique BamHI cloning site is present directly downstream of the constitutively expressed broad fungal host range promoter for the *A. nidulans* gpdA gene (P. Punt et al., *J. Biotechnol*. 1991 17:19-33). This vector was constructed in such a way that genomic DNA fragments carrying a translation start codon (ATG) may be expressed. To provide a selection marker for this vector, a NotI-BamHI fragment from pBLUEpyrE was cloned in the NotI-BglII digested expression vector termed pAN52-BamHI, resulting in vector pAN52-pyrE. *Chrysosporium* genomic DNA fragments in a size range of 3-6 kb were obtained partial Sau3A digestion. After ligation of these fragments into the BamHI-digested expression vector pAN52-pyrE, a number of recombinant clones sufficient to cover the full *Chrysosporium* genome several times was obtained. A number of these clones were pooled to cover at least 5-10 fungal genome equivalents. Plasmid DNA of these pools was prepared and used for transformation of *Chrysosporium* pyr5 or *Aspergillus* pyrE mutants. Transformant collections were generated in a microplate format as described above, and used for further functional/activity screening. Alternatively, an expression library may be constructed using specifically regulated *Chrysosporium* promoters, as described in PCT/NL99/00618.

REFERENCES CITED IN EXAMPLES (The contents of the following, and all patents and references cited hereinabove, are incorporated herein by reference):

1. Calmels T. P., Martin F., Durand H., and Tiraby G. (1991) *Proteolytic events in the processing of secreted proteins in fungi*. J. Biotechnol. 17(1):51-66.

2. Punt P. J., Dingemanse M. A., Jacobs-Meijsing B. J., Pouwels P. H., and van den Hondel C. A. (1988) *Isolation and characterization of the glyceraldehyde-3-phosphate dehydrogenase gene of Aspergillus nidulans*. Gene 69(1):49-57.

3. Shoemaker S., Schweickart V., Ladner M., Gelfand D., Kwok S., Myambo K., and Innis M. (1983) *Molecular cloning of exo-cellobiohydrolase I derived from Trichoderma reesei strain L27*. Bio/Technology October:691-696.

4. Drocourt D., Calmels T., Reynes J. P., Baron M., and Tiraby G. (1990) *Cassettes of the Streptoalloteichus hindustanus ble gene for transformation of lower and higher eukaryotes to phleomycin resistance*. Nucleic Acids Res. 18(13):4009.

5. Mullaney E. J., Hamer J. E., Roberti K. A., Yelton M. M., and Timberlake W. E. (1985) *Primary structure of the trpC gene from Aspergillus nidulans*. Mol. Gen. Genet. 199(1):37-45.

6. Yanisch-Perron C., Vieira J., and Messing J. (1987) *Improved M13 phage cloning vectors and host strains: nucleotide sequences of the M13mp18 and pUC19 vectors*. Gene 33:103-119.

7. Durand H., Baron M., Calmels T., and Tiraby G. (1988) *Classical and molecular genetics applied to Trichoderma reesei for the selection of improved cellulolytic industrial strains*, in Biochemistry and genetics of cellulose degradation, J. P. Aubert, Editor. Academic Press. pp. 135-151.

8. Lowry O. H., Rosebrough N. J., Farr A. L., and Randall R. J. (1951) *Protein measurements with the folin phenol reagent*. J. Biol. Chem 193, 265-275.

9. Parriche M., Bousson J. C., Baron M., and Tiraby G. *Development of heterologous protein secretion systems in filamentous fungi*. in 3rd European Conference on Fungal Genetics. 1996. Münster, Germany.

10. Baron M., Tiraby G., Calmels T., Parriche M., and Durand H. (1992) *Efficient secretion of human lysozyme fused to the Sh-ble phleomycin resistance protein by the fungus Tolypocladium geodes*. J. Biotechnol. 24(3):253-266.

11. Jeenes D. J., Marczinke B., MacKenzie D. A., and Archer D. B. (1993) *A truncated glucoamylase gene fusion for heterologous protein secretion from Aspergillus niger*. FEMS Microbiol. Lett. 107(2-3):267-271.

12. Stone P. J., Makoff A. J., Parish J. H., and Radford A. (1993) *Cloning and sequence-analysis of the glucoamylase gene of neurospora-crassa*. Current Genetics 24(3):205-211.

13. Mörsky P. (1983) *Turbidimetric determination of lysozyme with Micrococcus lysodeikticus cells: Reexamination of reaction conditions.* Analytical Biochem. 128:77-85.

14. Paluh J. L., Orbach M. J., Legerton T. L., and Yanofsky C. (1988) *The cross-pathway control gene of Neurospora crassa, cpc-1, encodes a protein similar to GCN4 of yeast and the DNA-binding domain of the oncogene v-jun-encoded protein.* Proc. Natl. Acad. Sci. USA 85(11):3728-32.

15. Nakari T., Onnela M. L., Ilmen M., Nevalainen K., and Penttilä M. (1994) *Fungal promoters active in the presence of glucose*, International patent application WO 94/04673

16. Torronen A., Mach R. L., Messner R., Gonzalez R., Kalkkinen N., Harkki A., and Kubicek C. P. (1992) *The two major xylanases from Trichoderma reesei: characterization of both enzymes and genes.* Biotechnology 10(11):1461-5.

17. Farkas V. (1985) *Novel media for detection of microbial producers of cellulase and xylanase.* FEMS Microbiol. Letters 28:137-140.

18. Miller G. L. (1959) *Use of dinitrosalicylic acid reagent for determination of reducing sugar.* Anal. Chem. 31:426-428.

19. Punt P. J., Mattem I. E., van den Hondel C. A. M. J. J. (1988) *A vector for Aspergillus transformation conferring phleomycin resistance.* Fungal Genetics Newsletter 35, 25-30.

---

SEQUENCE LISTING

```
<160> NUMBER OF SEQ ID NOS: 8

<210> SEQ ID NO 1
<211> LENGTH: 1578
<212> TYPE: DNA
<213> ORGANISM: Aspergillus niger

<400> SEQUENCE: 1
gggttaatgt gaaggcgtta gtggtaatgt atattaatgg tgagatgggc tttgattggg      60
tttaattgga atctgtatat tttcagatgg agtcaacttt tgaatggcca atatatcctc     120
ggcgataccg tcggagataa gataagaata atcgcacact attcccaaag catactggta     180
catactgcat tcggctagtg cggggtgctt acctcatcca cccgaatgag cccaactttt     240
ttgtctcaat caataattgc atccaaattc ccccgcaact tccccctcca accccgtgtc     300
tataccactc cctccacacc cacacaatca caatggctct ccctgcctac aagaccgcct     360
tcctggagtc tctcgtcggc caacgtgctg actttcggca ccttcaccct gaagtcgggt     420
cgccgtgcgt caccectcca acaccggcat tatcgcaatc ggaagactta ccactgtata     480
cagactcccc ctacttcttc aacgccggca tcttcaacac cgcctctctc ctctccgccc     540
tctccaccat ggcccacacc atcatcacct tcctcgctga gaacccttcc atccccaagc     600
ccgacgtcat gcttcgggta aaaaacccccc tctttcccca atacccccact tccactcaac     660 aacccataaa taactaacaa aaaccccctta aacagccccg catacaaagg catccccctc     720
gcgtgcgcca ccctccttga actcaaccgc atcgaccccg ccacctgggg cagcgtgtcc     780
tacagctaca accgcaaaga agccaaggat cacggcgaag gcggcaacat tgtcggcgcc     840
gctctgaagg gcaagaccgt gcttgtgatc gacgatgtca tcacggccgg taccgccatg     900
cgtgagaccc tcaacctggt cgccaaggag ggcggcaagg tcgtcggatt cactgttgct     960
ctggaccgct tggagaagat gcccggaccc aaggacgaga acggtgtcga ggacgataag    1020
cccagaatga gtgctatggg tcagatccgt aaggagtatg tgtgcccac gacgagtatt    1080 gttactctgg atgatttgat caagttgatg caggcgaagg gcaatgaggc cgatatgaag    1140
cggttggagg agtatagggc taagtatcag gctagtgatt agtcggtttc attgaccgat    1200
tgtttgggtg ggtgtgagag gttaggttag gttgtgggcg taggaatgaa aagctgtata    1260 catagggggcc tgaagaggtg cgtagagacg gtcgtgagat gttttatgtc aaaatcttga    1320
acaaatgaca ccttaaaaaa gaccccttgg tttcagctga attagcccgg aaagatgctc    1380
ggcacgccat gagtctagcc cactcagtgg gcacccgttt cccacatttg aagtggccga    1440
cgcttatttg gctgaggctg tggcctggaa aggcactatg gcgtgctgcg gtacaaggcc    1500
```

```
ggggctggcg tacgaaccac gacgcccgaa gggaactctt cggtcttact actactatgt   1560
ccccagttga cccccga                                                  1578
```

<210> SEQ ID NO 2
<211> LENGTH: 512
<212> TYPE: PRT
<213> ORGANISM: Aspergillus niger

<400> SEQUENCE: 2

```
Gly Leu Met Arg Arg Trp Cys Ile Leu Met Val Arg Trp Ala Leu Ile
  1               5                  10                  15

Gly Phe Asn Trp Asn Leu Tyr Ile Phe Arg Trp Ser Gln Leu Leu Asn
                 20                  25                  30

Gly Gln Tyr Ile Leu Gly Asp Thr Val Gly Asp Lys Ile Arg Ile Ile
             35                  40                  45

Ala His Tyr Ser Gln Ser Ile Leu Val His Thr Ala Phe Gly Cys Gly
         50                  55                  60

Val Leu Thr Ser Ser Thr Arg Met Ser Pro Thr Phe Leu Ser Gln Ser
 65                  70                  75                  80

Ile Ile Ala Ser Lys Phe Pro Arg Asn Phe Pro Leu Gln Pro Arg Val
                 85                  90                  95

Tyr Thr Thr Pro Ser Thr Pro Thr Gln Ser Gln Trp Leu Ser Leu Pro
                100                 105                 110

Thr Arg Pro Pro Ser Trp Ser Leu Ser Ser Ala Asn Val Leu Thr Phe
            115                 120                 125

Gly Thr Phe Thr Leu Lys Ser Gly Arg Arg Ala Ser Pro Leu Gln His
        130                 135                 140

Arg His Tyr Arg Asn Arg Lys Thr Tyr His Cys Ile Gln Thr Pro Pro
145                 150                 155                 160

Thr Ser Ser Thr Pro Ala Ser Ser Thr Pro Leu Ser Ser Pro Pro
                165                 170                 175

Ser Pro Pro Trp Pro Thr Pro Ser Ser Pro Ser Ser Leu Arg Thr Leu
                180                 185                 190

Pro Ser Pro Ser Pro Thr Ser Cys Phe Gly Lys Thr Pro Ser Phe Pro
            195                 200                 205

Asn Thr Pro Leu Pro Leu Asn Asn Pro Ile Thr Asn Lys Asn Pro Leu
        210                 215                 220

Asn Ser Pro Ala Tyr Lys Gly Ile Pro Leu Ala Cys Ala Thr Leu Leu
225                 230                 235                 240

Glu Leu Asn Arg Ile Asp Pro Ala Thr Trp Gly Ser Val Ser Tyr Ser
                245                 250                 255

Tyr Asn Arg Lys Glu Ala Lys Asp His Gly Glu Gly Gly Asn Ile Val
                260                 265                 270

Gly Ala Ala Leu Lys Gly Lys Thr Val Leu Val Ile Asp Asp Val Ile
            275                 280                 285

Thr Ala Gly Thr Ala Met Arg Glu Thr Leu Asn Leu Val Ala Lys Glu
        290                 295                 300

Gly Gly Lys Val Val Gly Phe Thr Val Ala Leu Asp Arg Leu Glu Lys
305                 310                 315                 320

Met Pro Gly Pro Lys Asp Glu Asn Gly Val Glu Asp Lys Pro Arg
                325                 330                 335

Met Ser Ala Met Gly Gln Ile Arg Lys Glu Tyr Gly Val Pro Thr Thr
            340                 345                 350
```

```
Ser Ile Val Thr Leu Asp Asp Leu Ile Lys Leu Met Gln Ala Lys Gly
         355                 360                 365

Asn Glu Ala Asp Met Lys Arg Leu Glu Glu Tyr Arg Ala Lys Tyr Gln
370                 375                 380

Ala Ser Asp Ser Val Ser Leu Thr Asp Cys Leu Gly Gly Cys Glu Arg
385                 390                 395                 400

Leu Gly Val Val Gly Val Gly Met Lys Ser Cys Ile His Arg Gly Leu
                405                 410                 415

Lys Arg Cys Val Glu Thr Val Arg Cys Phe Met Ser Lys Ser Thr
                420                 425                 430

Asn Asp Thr Leu Lys Lys Thr Pro Trp Phe Gln Leu Asn Pro Gly Lys
        435                 440                 445

Met Leu Gly Thr Pro Val Pro Thr Gln Trp Ala Pro Val Ser His Ile
    450                 455                 460

Ser Gly Arg Arg Leu Phe Gly Cys Gly Leu Glu Arg His Tyr Gly
465                 470                 475                 480

Val Leu Arg Tyr Lys Ala Gly Ala Gly Val Arg Thr Thr Pro Glu
                485                 490                 495

Gly Asn Ser Ser Val Leu Leu Leu Leu Cys Pro Gln Leu Thr Pro Arg
            500                 505                 510

<210> SEQ ID NO 3
<211> LENGTH: 495
<212> TYPE: PRT
<213> ORGANISM: Aspergillus niger

<400> SEQUENCE: 3

Gly Cys Glu Gly Val Ser Gly Asn Val Tyr Trp Asp Gly Leu Leu Gly
1               5                   10                  15

Leu Ile Gly Ile Cys Ile Phe Ser Asp Gly Val Asn Phe Met Ala Asn
                20                  25                  30

Ile Ser Ser Ala Ile Pro Ser Glu Ile Arg Glu Ser His Thr Ile Pro
            35                  40                  45

Lys Ala Tyr Trp Tyr Ile Leu His Ser Ala Ser Ala Gly Cys Leu Pro
        50                  55                  60

His Pro Pro Glu Ala Gln Leu Phe Cys Leu Asn Gln Leu His Pro Asn
65                  70                  75                  80

Ser Pro Ala Thr Ser Pro Ser Asn Pro Val Ser Ile Pro Leu Pro Pro
                85                  90                  95

His Pro His Asn His Asn Gly Ser Pro Cys Leu Gln Asp Arg Leu Pro
            100                 105                 110

Gly Val Ser Arg Arg Pro Thr Cys Leu Ser Ala Pro Ser Pro Ser Arg
        115                 120                 125

Val Ala Val Arg His Pro Ser Asn Thr Gly Ile Ile Ala Ile Gly Arg
130                 135                 140

Leu Thr Thr Val Tyr Arg Leu Pro Leu Leu Gln Arg Arg His Leu
145                 150                 155                 160

Gln His Arg Leu Ser Pro Leu Arg Pro Leu His His Gly Pro His His
                165                 170                 175

His His Leu Pro Arg Glu Pro Phe His Pro Gln Ala Arg Arg His Ala
            180                 185                 190

Ser Gly Lys Lys Pro Pro Leu Ser Pro Ile Pro His Phe His Ser Thr
        195                 200                 205

Thr His Lys Leu Thr Lys Thr Pro Thr Ala Pro His Thr Lys Ala Ser
    210                 215                 220
```

-continued

Pro Ser Arg Ala Pro Ser Leu Asn Ser Thr Ala Ser Thr Pro Pro
225                 230                 235                 240

Pro Gly Ala Ala Cys Pro Thr Ala Thr Thr Ala Lys Lys Pro Arg Ile
                245                 250                 255

Thr Ala Lys Ala Ala Thr Leu Ser Ala Pro Leu Arg Ala Arg Pro Cys
            260                 265                 270

Leu Ser Thr Met Ser Ser Arg Pro Val Pro Pro Cys Val Arg Pro Ser
        275                 280                 285

Thr Trp Ser Pro Arg Arg Ala Ala Arg Ser Ser Asp Ser Leu Leu Leu
    290                 295                 300

Trp Thr Ala Trp Arg Arg Cys Pro Asp Pro Arg Thr Arg Thr Val Ser
305                 310                 315                 320

Arg Thr Ile Ser Pro Glu Val Leu Trp Val Arg Ser Val Arg Ser Met
                325                 330                 335

Val Cys Pro Arg Arg Val Leu Leu Leu Trp Met Ile Ser Ser Cys Arg
            340                 345                 350

Arg Arg Ala Met Arg Pro Ile Ser Gly Trp Arg Ser Ile Gly Leu Ser
        355                 360                 365

Ile Arg Leu Val Ile Ser Arg Phe His Pro Ile Val Trp Val Gly Val
    370                 375                 380

Arg Gly Val Arg Leu Trp Ala Glu Lys Ala Val Tyr Ile Gly Ala Arg
385                 390                 395                 400

Gly Ala Arg Arg Ser Asp Val Leu Cys Gln Asn Leu Glu Gln Met Thr
                405                 410                 415

Pro Lys Arg Pro Leu Gly Phe Ser Ile Ser Pro Glu Arg Cys Ser Ala
            420                 425                 430

Arg His Glu Ser Ser Pro Leu Ser Gly His Pro Phe Pro Thr Phe Glu
        435                 440                 445

Val Ala Asp Ala Tyr Leu Ala Glu Ala Val Ala Trp Lys Gly Thr Met
    450                 455                 460

Ala Cys Cys Gly Thr Arg Pro Gly Leu Ala Tyr Glu Pro Arg Arg Pro
465                 470                 475                 480

Lys Gly Thr Leu Arg Ser Tyr Tyr Tyr Val Pro Ser Pro Pro
                485                 490                 495

<210> SEQ ID NO 4
<211> LENGTH: 509
<212> TYPE: PRT
<213> ORGANISM: Aspergillus niger

<400> SEQUENCE: 4

Val Asn Val Lys Ala Leu Val Val Met Tyr Ile Asn Gly Glu Met Gly
1               5                   10                  15

Phe Asp Trp Val Leu Glu Ser Val Tyr Phe Gln Met Glu Ser Thr Phe
            20                  25                  30

Glu Trp Pro Ile Tyr Pro Arg Tyr Arg Arg Arg Asp Lys Asn Asn
        35                  40                  45

Arg Thr Leu Phe Pro Lys His Thr Gly Thr Tyr Cys Ile Arg Leu Val
    50                  55                  60

Arg Gly Ala Tyr Leu Ile His Pro Asn Glu Pro Asn Phe Phe Val Ser
65                  70                  75                  80

Ile Asn Asn Cys Ile Gln Ile Pro Pro Gln Leu Pro Pro Thr Pro
                85                  90                  95

-continued

```
Cys Leu Tyr His Ser Leu His Thr His Thr Ile Thr Met Ala Leu Pro
            100                 105                 110
Ala Tyr Lys Thr Ala Phe Leu Glu Ser Leu Val Gly Gln Arg Ala Asp
        115                 120                 125
Phe Arg His Leu His Pro Glu Val Gly Ser Pro Cys Val Thr Pro Pro
    130                 135                 140
Thr Pro Ala Leu Ser Gln Ser Glu Asp Leu Pro Leu Tyr Thr Asp Ser
145                 150                 155                 160
Pro Tyr Phe Phe Asn Ala Gly Ile Phe Asn Thr Ala Ser Leu Leu Ser
                165                 170                 175
Ala Leu Ser Thr Met Ala His Thr Ile Ile Thr Phe Leu Ala Glu Asn
            180                 185                 190
Pro Ser Ile Pro Lys Pro Asp Val Met Leu Arg Val Lys Asn Pro Leu
        195                 200                 205
Phe Pro Gln Tyr Pro Thr Ser Thr Gln Gln Pro Ile Asn Asn Gln Lys
    210                 215                 220
Pro Pro Lys Gln Pro Arg Ile Gln Arg His Pro Pro Arg Val Arg His
225                 230                 235                 240
Pro Pro Thr Gln Pro His Arg Pro Arg His Leu Gly Gln Arg Val Leu
                245                 250                 255
Gln Leu Gln Pro Gln Arg Ser Gln Gly Ser Arg Arg Arg Arg Gln His
            260                 265                 270
Cys Arg Arg Arg Ser Glu Gly Gln Asp Arg Ala Cys Asp Arg Arg Cys
        275                 280                 285
His His Gly Arg Tyr Arg His Ala Asp Pro Gln Pro Gly Arg Gln Gly
    290                 295                 300
Gly Arg Gln Gly Arg Arg Ile His Cys Cys Ser Gly Pro Leu Gly Glu
305                 310                 315                 320
Asp Ala Arg Thr Gln Gly Arg Glu Arg Cys Arg Gly Arg Ala Gln Asn
                325                 330                 335
Glu Cys Tyr Gly Ser Asp Pro Gly Val Trp Cys Ala His Asp Glu Tyr
            340                 345                 350
Cys Tyr Ser Gly Phe Asp Gln Val Asp Ala Gly Glu Gly Gln Gly Arg
        355                 360                 365
Tyr Glu Ala Val Gly Gly Val Gly Val Ser Gly Leu Val Gly Phe Ile
    370                 375                 380
Asp Arg Leu Phe Gly Trp Val Glu Val Arg Leu Gly Cys Gly Arg Arg
385                 390                 395                 400
Asn Glu Lys Leu Tyr Thr Gly Pro Glu Glu Val Arg Arg Asp Gly Arg
                405                 410                 415
Glu Met Phe Tyr Val Lys Ile Leu Asn Lys His Leu Lys Lys Asp Pro
            420                 425                 430
Leu Val Ser Ala Glu Leu Ala Arg Lys Asp Ala Arg His Ala Met Ser
        435                 440                 445
Leu Ala His Ser Val Gly Thr Arg Phe Pro His Leu Lys Trp Pro Thr
    450                 455                 460
Leu Ile Trp Leu Arg Leu Trp Pro Gly Lys Ala Leu Trp Arg Ala Ala
465                 470                 475                 480
Val Gln Gly Arg Gly Trp Arg Thr Asn His Asp Ala Arg Arg Glu Leu
                485                 490                 495
Phe Gly Leu Thr Thr Thr Met Ser Pro Val Asp Pro Pro
            500                 505
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide sequence

<400> SEQUENCE: 5

Leu Gly Glu Arg Lys
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide sequence

<400> SEQUENCE: 6

Ser Gly Glu Arg Lys
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Gly Asp Leu
 1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Asp Phe Glu
 1
```

The invention claimed is:

1. A method, comprising the steps of:

(a) stably transforming a plurality of low viscosity filamentous fungi of less than about 200 cP, wherein the fungi are of a genus selected from the group consisting of: *Aspergillus, Trichoderma, Chrysosporium, Neurospora, Rhizomucor, Hansenula, Humicola, Mucor, Tolypocladium, Fusarium, Penicillium, Talaromyces, Emericella*, and *Hypocrea*, said fungi having a phenotype characterized by growth in suspension and by the production of transferable reproductive elements in suspension with a library of vectors which comprises a plurality of different vectors, each different vector comprising a different mutant protein-encoding nucleic acid sequence so as to introduce into each of a plurality of individual fungi at least one heterologous protein-encoding nucleic acid sequence;

(b) culturing the transformed filamentous fungi under conditions conducive to the formation of transferable reproductive elements;

(c) separating from one another a plurality of transferable reproductive elements;

(d) culturing into monoclonal cultures or clonal colonies the individual transferable reproductive elements, under conditions conducive to expression of the heterologous proteins encoded by the heterologous protein-encoding nucleic acid sequences;

(e) screening each individual clonal culture or clonal colony for an expressed protein having the activity or property of interest;

(f) isolating one or more individual clonal cultures or clonal colonies that express a protein exhibiting the activity or property of interest;

(g) mutating the DNA from the isolated individual clonal cultures or clonal colonies that encodes the protein exhibiting the activity or property of interest;

(h) preparing a library of vectors which comprise the mutated DNA sequences obtained in step (i); and (i) repeating steps (a) through (e), until the property or activity of interest is optimized.

2. The method of claim 1, further comprising between steps (f) and (g) the steps of: culturing one or more of the individual clonal cultures or clonal colonies isolated in step (f); isolating the expressed protein exhibiting the activity or property of interest; and evaluating the isolated protein for the property of interest.

3. The method of claim 1, wherein the screening step is carried out by high- throughput screening.

4. The method of claim 2, wherein the screening step is carried out by high- throughput screening.

5. The method of claim 1 wherein the fungus is of a genus selected from the group consisting of *Aspergillus, Fusarium, Chrysosporium,* and *Trichoderma*.

6. The method of claim 5, wherein the fungus is *Chrysosporium* strain UV18-25 having accession number VKM F-3631 D.

7. A method for obtaining a protein having an activity or property of interest, comprising optimizing the activity or property of interest by the method of claim 1, culturing an individual clonal culture or clonal colony isolated in the final step (f), and isolating the expressed protein from the culture.

* * * * *